US011484568B2

(12) United States Patent
Van Aroian et al.

(10) Patent No.: US 11,484,568 B2
(45) Date of Patent: Nov. 1, 2022

(54) ANTHELMINTIC COMPOSITIONS AND METHODS

(71) Applicant: UNIVERSITY OF MASSACHUSETTS, Boston, MA (US)

(72) Inventors: Raffi Van Aroian, Worcester, MA (US); Gary R. Ostroff, Worcester, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 21 days.

(21) Appl. No.: 16/067,109

(22) PCT Filed: Jan. 13, 2017

(86) PCT No.: PCT/US2017/013436
§ 371 (c)(1),
(2) Date: Jun. 28, 2018

(87) PCT Pub. No.: WO2017/123946
PCT Pub. Date: Jul. 20, 2017

(65) Prior Publication Data

US 2019/0015474 A1 Jan. 17, 2019

Related U.S. Application Data

(60) Provisional application No. 62/279,597, filed on Jan. 15, 2016.

(51) Int. Cl.
| | |
|---|---|
| *A61K 38/16* | (2006.01) |
| *A61P 33/10* | (2006.01) |
| *A61P 31/04* | (2006.01) |
| *A61K 9/00* | (2006.01) |
| *A61K 9/19* | (2006.01) |
| *C12N 15/70* | (2006.01) |
| *C12N 15/75* | (2006.01) |

(52) U.S. Cl.
CPC .......... *A61K 38/164* (2013.01); *A61K 9/0053* (2013.01); *A61K 9/19* (2013.01); *A61P 31/04* (2018.01); *A61P 33/10* (2018.01); *C12N 15/70* (2013.01); *C12N 15/75* (2013.01); *Y02A 50/30* (2018.01)

(58) Field of Classification Search
CPC ...... A61K 38/164; A61K 9/0053; A61K 9/19; A61P 33/10; A61P 31/04; C12N 15/70; C12N 15/75
See application file for complete search history.

(56) References Cited

U.S. PATENT DOCUMENTS 5,591,433 A 1/1997 Gabriel et al.
8,809,268 B2 * 8/2014 Aroian .................... A61P 33/10 514/4.6
2001/0010932 A1 8/2001 Schnepf et al.
2010/0024075 A1 1/2010 Aroian et al.
2011/0263489 A1 10/2011 Aroian et al.
2017/0348362 A1 * 12/2017 Aroian ................. A61K 35/744
2020/0188452 A1 * 6/2020 Aroian ................ A61K 35/741

FOREIGN PATENT DOCUMENTS

WO WO 2007062064 A2 5/2007
WO WO 2017123946 A1 7/2017

OTHER PUBLICATIONS

Is BT safe for human to Eat? Publication 2018, p. 1-3. Entomological Society of America (ESA).*
International Search Report of PCT/US2017/013436 dated May 24, 2017, 4 pp.
Durmaz et al., (Dec. 18, 2015), "Intracellular and Extracellular Expression of Bacillus thuringiensis Crystal Protein Cry5B in Lactococcus lactis for Use as an Anthelminthic", Applied and Environmental Microbiology, vol. 82, No. 4, pp. 1286-1294.
Wei J-Z et al., (Mar. 4, 2003), "Bacillus Thuringiensis Crystal Proteins That Target Nematodes", Proceedings National Academy of Sciences PNAS, National Academy of Sciences, US, vol. 100, No. 5, pp. 2760-2765.
Bethony J, Brooker S, Albonico M, Geiger SM, Loukas A, Diemert D, Hotez PJ. 2006. Soil-transmitted helminth infections: ascariasis, trichuriasis, and hookworm. Lancet 367:1521-1532.
Hall A, Hewitt G, Tuffrey V, de Silva N. 2008. A review and metaanalysis of the impact of intestinal worms on child growth and nutrition. Matern. Child Nutr. 4(Suppl 1):118-236.
Knopp S, Steinmann P, Keiser J, Utzinger J. 2012. Nematode infections: soil-transmitted helminths and trichinella. Infect. Dis. Clin. North Am. 26:341-358.
Tchuem Tchuente LA. 2011. Control of soil-transmitted helminths in sub-Saharan Africa: diagnosis, drug efficacy concerns and challenges. Acta Trop. 120(Suppl 1):S4-S11.
Hotez PJ. 2008. Forgotten people, forgotten diseases: the neglected tropical diseases and their impact on global health and development. ASM Press, Washington, DC.

(Continued)

*Primary Examiner* — Iqbal H Chowdhury
(74) *Attorney, Agent, or Firm* — Lathrop GPM LLP; James H. Velema; Judith L. Stone-Hulslander

(57) ABSTRACT

Compositions and methods for treating or reducing the severity or likelihood of occurrence of a parasitic worm or helminth infection in a subject are described. The methods include administering to the subject a therapeutically effective amount of a killed or inactivated recombinant bacterium expressing a crystal protein such as a *Bacillus thuringiensis* crystal protein (Cry) in the cytosol of the bacterium. The crystal proteins may be full length, truncated, variant, or sub-variant Cry proteins. Examples of crystal proteins include Cry5B, Cry21, Cry14A, Cry6A, and Cry13A. The recombinant bacteria may be treated with an anti-microbial agent before or during administration to a subject.

12 Claims, 40 Drawing Sheets

Specification includes a Sequence Listing.

(56) References Cited

OTHER PUBLICATIONS

Keiser J, Utzinger J. 2010. The drugs we have and the drugs we need against major helminth infections. Adv. Parasitol. 73:197-230.

Humphries D, Mosites E, Otchere J, Twum WA, Woo L, Jones-Sanpei H, Harrison LM, Bungiro RD, Benham-Pyle B, Bimi L, Edoh D, Bosompem K, Wilson M, Cappello M. 2011. Epidemiology of hookworm infection in Kintampo North Municipality, Ghana: patterns of malaria coinfection, anemia, and albendazole treatment failure. Am. J. Trop. Med. Hyg. 84:792-800.

Soukhathammavong PA, Sayasone S, Phongluxa K, Xayaseng V, Utzinger J, Vounatsou P, Hatz C, Akkhavong K, Keiser J, Odermatt P. 2012. Low efficacy of single-dose albendazole and mebendazole against hookworm and effect on concomitant helminth infection in Lao PDR. PLoS Negl. Trop. Dis. 6:e1417. doi:10.1371/journal.pntd. 0001417.

Stothard JR, Rollinson D, Imison E, Khamis IS. 2009. A spot-check of the efficacies of albendazole or levamisole, against soil-transmitted helminthiases in young Ungujan children, reveals low frequencies of cure. Ann. Trop. Med. Parasitol. 103:357-360.

Geary TG, Woo K, McCarthy JS, Mackenzie CD, Horton J, Prichard RK, de Silva NR, Olliaro PL, Lazdins-Helds JK, Engels DA, Bundy DA. 2010. Unresolved issues in anthelmintic pharmacology for helminthiases of humans. Int. J. Parasitol. 40:1-13.

Holden-Dye L, Walker RJ. 2007. Anthelmintic drugs. WormBook2007: 1-13.

Cappello M, Bungiro RD, Harrison LM, Bischof LJ, Griffitts JS, Barrows BD, Aroian RV. 2006. A purified Bacillus thuringiensis crystal protein with therapeutic activity against the hookworm parasite Ancylostoma ceylanicum. Proc. Natl. Acad. Sci. U. S. A. 103:15154-15159.

Hu Y. et al. (2010) "Bacillus thuringiensis Cry5B protein is highly efficacious as a single-dose therapy against an intestinal roundworm infection in mice," PLoS Negl. Trop. Dis. 4(3):e614, 7 pages.

Hu Y, Zhan B, Keegan B, Yiu YY, Miller MM, Jones K, Aroian RV. 2012. Mechanistic and single-dose in vivo therapeutic studies of Cry5B anthelmintic action against hookworms. PLoS Negl. Trop. Dis. 6:e1900. doi:10.1371/journal.pntd.0001900.

Cutting SM. 2011. Bacillus probiotics. Food Microbiol. 28:214-220.

Casula G, Cutting SM. 2002. Bacillus probiotics: spore germination in the gastrointestinal tract. Appl. Environ. Microbiol. 68:2344-2352.

Duc LH, Hong HA, Barbosa TM, Henriques AO, Cutting SM. 2004. Characterization of Bacillus probiotics available for human use. Appl. Environ. Microbiol. 70:2161-2171.

Hoa NT, Baccigalupi L, Huxham A, Smertenko A, Van PH, Ammendola S, Ricca E, Cutting AS. 2000. Characterization of *Bacillus* species used for oral bacteriotherapy and bacterioprophylaxis of gastrointestinal disorders. Appl. Environ. Microbiol. 66:5241-5247.

Hoa TT, Duc LH, Isticato R, Baccigalupi L, Ricca E, Van PH, Cutting SM. 2001. Fate and dissemination of Bacillus subtilis spores in a murine model. Appl. Environ. Microbiol. 67:3819-3823.

Hong HA, Huang JM, Khaneja R, Hiep LV, Urdaci MC, Cutting SM. 2008. The safety of Bacillus subtilis and Bacillus indicus as food probiotics. J. Appl. Microbiol. 105:510-520.

D'Arienzo R, Maurano F, Mazzarella G, Luongo D, Stefanile R, Ricca E, Rossi M. 2006. Bacillus subtilis spores reduce susceptibility to Citrobacter rodentium-mediated enteropathy in a mouse model. Res. Microbiol. 157: 891-897.

Duc LH, Hong HA, Fairweather N, Ricca E, Cutting SM. 2003. Bacterial spores as vaccine vehicles. Infect. Immun. 71:2810-2818.

Hoang TH, Hong HA, Clark GC, Titball RW, Cutting SM. 2008. Recombinant Bacillus subtilis expressing the Clostridium perfringens alpha toxoid is a candidate orally delivered vaccine against necrotic enteritis. Infect. Immun. 76:5257-5265.

La Ragione RM, Casula G, Cutting SM, Woodward MJ. 2001. Bacillus subtilis spores competitively exclude *Escherichia coli* O78:K80 in poultry. Vet. Microbiol. 79:133-142.

La Ragione RM, Woodward MJ. 2003. Competitive exclusion by Bacillus subtilis spores of *Salmonella enterica* serotype Enteritidis and Clostridium perfringens in young chickens. Vet. Microbiol. 94:245-256.

Permpoonpattana P, Hong HA, Phetcharaburanin J, Huang JM, Cook J, Fairweather NF, Cutting SM. 2011. Immunization with Bacillus spores expressing toxin A peptide repeats protects against infection with Clostridium difficile strains producing toxins A and B. Infect. Immun. 79: 2295-2302.

Song M, Hong HA, Huang JM, Colenutt C, Khang DD, Nguyen TV, Park SM, Shim BS, Song HH, Cheon IS, Jang JE, Choi JA, Choi YK, Stadler K, Cutting SM. 2012. Killed Bacillus subtilis spores as a mucosal adjuvant for an H5N1 vaccine. Vaccine 30:3266-3277.

Conlan JV, Khamlome B, Vongxay K, Elliot A, Pallant L, Sripa B, Blacksell SD, Fenwick S, Thompson RC. 2012. Soil-transmitted helminthiasis in Laos: a community-wide cross-sectional study of humans and dogs in a mass drug administration environment. Am. J. Trop. Med. Hyg. 86:624-634.

Marroquin LD, Elyassnia D, Griffitts JS, Feitelson JS, Aroian RV. 2000. Bacillus thuringiensis (Bt) toxin susceptibility and isolation of resistance mutants in the nematode Caenorhabditis elegans. Genetics 155:1693-1699.

Dubnau D, Davidoff-Abelson R. 1971. Fate of transforming DNA following uptake by competent Bacillus subtilis. I. Formation and properties of the donor-recipient complex. J. Mol. Biol. 56:209-221.

Sierro N, Makita Y, de Hoon M, Nakai K. 2008. DBTBS: a database of transcriptional regulation in Bacillus subtilis containing upstream intergenic conservation information. Nucleic Acids Res. 36:D93-D96.

Shevchenko A, Wilm M, Vorm O, Mann M. 1996. Mass spectrometric sequencing of proteins from silver-stained polyacrylamide gels. Anal. Chem. 68:850-858.

National Research Council. 1996. Guide for the care and use of laboratory animals. National Academies Press, Washington, DC.

Hu Y, Xiao SH, Aroian RV. 2009. The new anthelmintic tribendimidine is an L-type (levamisole and pyrantel) nicotinic acetylcholine receptor agonist. PLoS Negl. Trop. Dis. 3:e499. doi:10.1371/journal.pntd.0000499.

Hu Y, Platzer EG, Bellier A, Aroian RV. 2010. "Discovery of a highly synergistic anthelmintic combination that shows mutual hypersusceptibility," Proc. Natl. Acad. Sci. U. S. A. 107:5955-5960.

Lereclus D, Arantes O, Chaufaux J, Lecadet M. 1989. Transformation and expression of a cloned delta-endotoxin gene in Bacillus thuringiensis. FEMS Microbiol. Lett. 51:211-217.

Yang Y, Qi Y, Huang Y. 1996. Cloning and expression of full-length delta-endotoxin cryIA(c) gene in three kinds of prokaryotic systems using shuttle vector pHT3101. Wei Sheng Wu Xue Bao 36:173-180.

Youngman P, Perkins JB, Losick R. 1984. Construction of a cloning site near one end of Tn917 into which foreign DNA may be inserted without affecting transposition in Bacillus subtilis or expression of the transposonborne erm gene. Plasmid 12:1-9.

Cannon RJC. 1996. Bacillus thuringiensis use in agriculture: a molecular perspective. Biol. Rep. 71:561-636.

Hu Y, Aroian RV. 2012. Promise of Bacillus thuringiensis crystal proteins as anthelmintics, p. 267-281. In Caffrey CR (ed), Parasitic helminths: targets, screens, drugs, and vaccines. Wiley-VCH Verlag Gmh & Co, KGaA, Weinheim, Germany.

Bischof LJ, Huffman DL, Aroian RV. 2006. Assays for toxicity studies in C. elegans with Bt crystal proteins. Methods Mol. Biol. 351:139-154.

Kho MF, Bellier A, Balasubramani V, Hu Y, Hsu W, Nielsen-LeRoux C, McGillivray SM, Nizet V, Aroian RV. 2011. The pore-forming protein Cry5B elicits the pathogenicity of *Bacillus* sp. against Caenorhabditis elegans. PLoS One 6:e29122. doi:10.1371/journal.pone.0029122.

Baum JA, Malvar T. 1995. Regulation of insecticidal crystal protein production in Bacillus thuringiensis. Mol. Microbiol. 18:1-12.

Buasri W, Panbangred W. 2012. Large crystal toxin formation in chromosomally engineered *Bacillus thuringiensis* subsp. aizawai due to sigmaE accumulation. Appl. Environ. Microbiol. 78:1682-1691.

(56) References Cited

OTHER PUBLICATIONS

Brans A, Filee P, Chevigne A, Claessens A, Joris B. 2004. New integrative method to generate Bacillus subtilis recombinant strains free of selection markers. Appl. Environ. Microbiol. 70:7241-7250.

Tritten L, Nwosu U, Vargas M, Keiser J. 2012. In vitro and in vivo efficacy of tribendimidine and its metabolites alone and in combination against the hookworms Heligmosomoides bakeri and Ancylostoma ceylanicum. Acta Trop. 122:101-107.

Tritten L, Silbereisen A, Keiser J. 2011. In vitro and in vivo efficacy of monepantel (AAD 1566) against laboratory models of human intestinal nematode infections. PLoS Negl. Trop. Dis. 5:e1457. doi: 10.1371/journal.pntd.0001457.

Griffitts JS, Aroian RV. 2005. Many roads to resistance: how invertebrates adapt to Bt toxins. Bioessays 27:614-624.

Griffitts JS, Haslam SM, Yang T, Garczynski SF, Mulloy B, Morris H, Cremer PS, Dell A, Adang MJ, Aroian RV. 2005. Glycolipids as receptors for Bacillus thuringiensis crystal toxin. Science 307:922-925.

Los FC, Kao CY, Smitham J, McDonald KL, Ha C, Peixoto CA, Aroian RV. 2011. RAB-5- and RAB-11-dependent vesicle-trafficking pathways are required for plasma membrane repair after attack by bacterial poreforming toxin. Cell Host Microbe 9:147-157.

Wang F, Liu Y, Zhang F, Chai L, Ruan L, Peng D, Sun M. 2012. Improvement of crystal solubility and increasing toxicity against Caenorhabditis elegans by asparagine substitution in block 3 of Bacillus thuringiensis crystal protein Cry5Ba. Appl. Environ. Microbiol. 78:7197-7204.

El-Bendary MA. 2006. Bacillus thuringiensis and Bacillus sphaericus biopesticides production. J. Basic Microbiol. 46:158-170.

Schallmey M, Singh A, Ward OP. 2004. Developments in the use of *Bacillus* species for industrial production. Can. J. Microbiol. 50:1-17.

Fujiwara RT, Geiger SM, Bethony J, Mendez S. 2006. Comparative immunology of human and animal models of hookworm infection. Parasite Immunol., 28:285-293.

Stepek G, Lowe AE, Buttle DJ, Duce IR, Behnke JM. 2007. Anthelmintic action of plant cysteine proteinases against the rodent stomach nematode, Protospirura muricola, in vitro and in vivo. Parasitology, 134:103-112.

Hu Y, Ellis BL, Yiu YY, Miller MM, Urban JF, Shi LZ, Aroian RV. 2013. An extensive comparison of the effect of anthelmintic classes on diverse nematodes. PLoS One, 8(7):e70702, 12 pages.

Lee AC, Epe C, Simpson KW, Bowman DD. 2011. Utility of capsule endoscopy for evaluating anthelmintic efficacy in fully conscious dogs. Int. J. Parasitol., 41:1377-1383.

Lee AC, Epe C, Bowman DD. 2015. Determination of anthelmintic efficacy against Toxocara canis in dogs by use of capsule endoscopy. Vet. Parasitol., 212:227-231.

Agaisse H, Lereclus D. 1994. Structural and functional analysis of the promoter region involved in full expression of the cryIIIA toxin gene of Bacillus thuringiensis. Mol. Microbiol., 13(1):97-107.

Boontawan A, Stuckey DC. 2005. Mass transfer of terpenes through a silicone rubber membrane in a liquid-liquid contacting system. Biotechnol. Prog.

Krings U, Berger RG. 1998. Biotechnological production of Øavours and fragrances. Appl. Microbiol. Biotechnol.

Chan AC, Ager D, Thompson IP. 2013. Resolving the mechanism of bacterial inhibition by plant secondary metabolites employing a combination of whole-cell biosensor. J. Microbiol. Methods.

Agaisse H, Lereclus D. 1994. Expression in Bacillus subtilis of the Bacillus thuringiensis cryIIIA toxin gene is not dependent on a sporulation-specific sigma factor and is increased in a spo0A mutant. J. Bacteriol., 176(15):4734-4741.

Urban et al. (2013) "Bacillus thuringiensis-derived Cry5B has potent anthelmintic activity against Ascaris suum," PLoS Negl. Trop. Dis., 7(6):e2263, 7 pages.

Roh JY, Choi JY, Li MS, Jin BR, Je YH. 2007. Bacillus thuringiensis as a specific, safe, and effective tool for insect pest control. J. Microbiol. Biotechnol, 17(4):547-559.

Hu Y, Miller MM, Derman AI, Ellis BL, Monnerat RG, Pogliano J, Aroian RV. 2013. Bacillus subtilis strain engineered for treatment of soil-transmitted helminth diseases. Appl. Environ. Microbiol., 79(18):5527-5532.

Silvaggi, J., et al. Unmasking novel sporulation genes in Bacillus subtillus. J Bacteriol. 186, 8089-8095, 2004.

Sandman, K., et al. Genetic Analysis of Bacillus subtilis spo Mutations Generated by Tn917-Mediated Insertional Mutagenesis. Genetics. 117, 603-617, 1987.

Malvar and Baum, Tn5401 Disruption of the spoOF Gene, Identified by Direct Chromosomal Sequencing, Results in CryIIIA Overproduction in Bacillus thuringiensis. J Bacteriol. 176, 4750-4753, 1994.

Lereclus D. et al. (1995) "Overproduction of Encapsulation Insecticidal Crystal Proteins in a Bacillus thuringiensis spo0A Mutant," Bio/Technology, 13:67-71.

Brooker et al. (2008) "Hookworm-Related Anaemia among Pregnant Women: A Systematic Review," PLoS Negl. Trop. Dis., 2(9): e291, 9 pages.

Xiaohu Shao et al. (2009) "Surface display of heterologous proteins in Bacillus thuringiensis using a peptidoglycan hydrolase anchor," Microbial Cell Factories, 8:48, 17 pages.

Keiser, J. and Utzinger, J. (2008) "Efficacy of Current Drugs Against Soil-Transmitted Helminth Infections," JAMA, 299(16):1937-1948.

Mohamadzadeh M. et al. (2009) "Dendritic cell targeting of Bacillus anthracis protective antigen expressed by Lactobacillus acidophilus protects mice from lethal challenge," PNAS, 106(11):4331-4336.

Betz F. S. et al. (2000) "Safety and Advantages of Bacillus thuringiensis—Protected Plants to Control Insect Pests," Regulatory Toxicology and Pharmacology, 32:152-173.

Xiang-Qian Li et al. (2008) "Expression of Cry5B protein from Bacillus thuringiensis in plant roots confers resistance to root-knot nematode," Biological Control, 47:97-102.

Griffits et al. (2001) "Bt Toxin Resistance from Loss of a Putative Carbohydrate-Modifying Enzyme," Science, 293:860-864.

Crickmore, N. et al. (1998) "Revision of the Nomenclature for the Bacillus thuringiensis Pesticidal Crystal Proteins," Microbiology and Molecular Biology Reviews, 62(3):807-813.

Schnepf, E. et al. (1998) "Bacillus thuringiensis and Its Pesticidal Crystal Proteins," Microbiology and Molecular Biology Reviews, 62(3):775-806.

Rudd A. de Maagd et al. (2001) "How Bacillus thuringiensis has evolved specific toxins to colonize the insect world," Trends in Genetics, 17(4):193-199.

Trang Thi Phuong Phan et al. (2006) "Novel plasmid-based expression vectors for intra- and extracellular production of recombinant proteins in Bacillus subtilis," Protein Expression and Purification, 46:189-195.

Sayaka Ashikaga et al. (2000) "Natural Genetic Competence in Bacillus subtilis Natto OK2," J. of Bacter., 182(9):2411-2415.

Romero D. et al. (2006) "Transformation of undomesticated strains of Bacillus subtilis by protoplast electroporation," J. of Microl. Methods, 66:556-559.

Moran, M. et al.. (2009) "Neglected Disease Research & Development: New Times, New Trends," G-Finder, 106 pages.

Ge et al. (1990) "Hyperexpression of a Bacillus thuringiensis delta-endotoxin gene in *Escherichia coli*: properties of the product," Gene, 93:49-54.

Peng et al. (2003) "A Delta-endotoxin encoded in Pseudomas fluorescens displays a high degree of insectidal activity," Appl. Microbiol. Biotechnol., 63:300-306.

Battcock, FAO Agricultural Services Bulletin No. 134, 1998.

Bermudez-Humaran et al., "Lactococci and lactobacillin as mucosal delivery vectors for therapeutic proteins and DNA vaccines", Microbial cell fractories, pp. 1-10 (2011).

Beveridge, Cellular Responses of Bacillus subtilis and *Escherichia coli* to the Gram Stain, Journal of Bacteriology 1983, 156: 846-858, 1983.

Coelho et al., "Probiotic therapy: a promising strategy for the control of canine hookworm", Journal of Parasitology research, doi.org/10.1155/2013/430413. (2013).

(56) References Cited

OTHER PUBLICATIONS

Ferrer-Miralles, "Bacterial cell factories for recombinant protein production; expanding the catalogue", Microbial Cell Factories 2013, 12:113.

Iatsenko, "Molecular Mechanisms of Caenorhabditis elegans—Bacillus Interactions", Dissertations, der Eberhard Karls Universität Tübingen, Jun. 23, 2014.

\* cited by examiner

Cry5Ba1

| | | | | | | |
|---|---|---|---|---|---|---|
| 1 | MATINELYPV | PYNVLAHPIK | EVDDPYSWSN | LLKGIQEGWE | EWGKTGQKKL | FEDHLTIAWN |
| 61 | LYKTGKLDYE | ALTKASISLI | GFIPGAEAAV | PFINMEVDFV | WPKLFGANTE | GKDQQLFNAI |
| 121 | MDAVNKMVDN | KFLSYNLSTL | NKTIEGIQGN | LGLFQNAIQV | AICQGSTPER | VNFDQNCTPC |
| 181 | NPNQPCKDDL | DRVASRFDTA | NSQFTQHLPE | FKNPWSDENS | TQEFKRTSVE | LTLPMYTTVA |
| 141 | TLHLLLYEGY | IEFMTKWNFH | NEQYLNNLKV | ELQQLIHSYS | ETVRTSFLQF | LPTLNNRSKS |
| 301 | SVNAYNRYVR | NMTVNCLDIA | ATWPTFDTHN | YHQGGKLDLT | RIILSDTAGP | IEEYTTGDKT |
| 361 | SGPEHSNITP | NNILDTPSPT | YQHSFVSVDS | IVYSRKELQQ | LDIATYSTNN | SNNCHPYGLR |
| 421 | LSYTDGSRYD | YGDNQPDFTT | SNNNYCHNSY | TAPITLVNAR | HLYNAKGSLQ | NVESLVVSTV |
| 481 | NGGSGSCICD | AWINYLRPPQ | TAKNESFPDQ | KDNVLYPITE | TVNKGTGGNL | GVISAYVPME |
| 541 | LVPENVIGDV | NADTKLPLTQ | LKGFPFEKYG | SEYNNRGISL | VREWINGNNA | VKLSNSQSVG |
| 601 | IQITNQTEQK | YEIRCRYASK | GDNNVYFNVD | LSENPFRNSI | SFGSTESSVV | GVQGENGKYI |
| 661 | LKSITTVEIP | AGSFYVHITN | QGSSDLFLDR | IEFVPKIQFQ | FCDNNNLHCD | CNNPVDTDCT |
| 721 | FCCVCTSLTD | CDCNNPRGLD | CTLCCQVENQ | LPSFVTLTDL | QNITTQVNAL | VASSEHDTLA |
| 781 | TDVSDYEIEE | VVLKVDALSG | EVFGKEKKAL | RKLVNHTKRL | SKARNLLIGG | NFDNLDAWYR |
| 841 | GRNVVNVSDH | ELFKSDHYLL | PPPTLYSSYM | FQKVEESKLK | ANTRYSVSGF | IAHAEDLEIV |
| 901 | VSEYGQEVKK | VVQVPYGEAF | PLTSRGAICC | PPRSTSNGKP | ADPHEFSYSI | DVGTLDVEAN |
| 961 | PGIELGLRIV | ERTGMARYSN | LEIREDPPLK | KNELRNVQRA | ARNWRSAYDQ | ERAEVTALIQ |
| 1021 | PVLNQINALY | ENEDWNGAIR | SGVSYHDLEA | IVLPTLPKLN | HWFMSDMLGE | QGSILAQFQE |
| 1081 | ALDRAYTQLE | ESTILHNGHF | TTDAANWTIE | GDAHHAILED | GRRVLRLPDW | SSSVSQTIEI |
| 1141 | ENFDPDKEYQ | LVFHAQGEGT | VSLQHGEEGE | YVETHPHKSA | NFTTSHRQGL | TFETNKVTVE |
| 1201 | ITSEDGEFLV | DHIALVEAPL | PTDDQSSDGN | TFSNTNSNTS | MNNNQ | |

Fig. 2

Cry13Aa1

| | | | | | | |
|---|---|---|---|---|---|---|
| 1 | MTCQLQAQPL | IPYNVLAGYP | TSNTGSPIGN | AGNQFDQFEQ | TVKELKEAWE | AFQKNGSFSL |
| 61 | AALEKGFDAA | IGGGSFDYLG | LVQAGLGLVG | TLGAAIPGVS | VAVPLISMLV | GVFWPKGTNN |
| 121 | QENLITVIDK | EVQRILDEKL | SDQLIKKINA | DLNAFTDLVT | RLEEVIIDAT | FENHKPVLQV |
| 181 | SKSNYMKVDS | AYFSTGGILT | LGMSDFLTDT | YSKLTFPLYV | LGATMKLSAY | HSYIQFGNTW |
| 241 | LNKVYDLSSD | EGKTMSQALA | RAKQHMRQDI | AFYTSQALNM | FTGNLPSLSS | NKYAINDYNV |
| 301 | YTRAMVLNGL | DIVATWPTLY | PDDYSSQIKL | EKTRVIFSDM | VGQSESRDGS | VTIKNIFDNT |
| 361 | DSHQHGSIGL | NSISYFPDEL | QKAQLRMYDY | NHKPYCTDCF | CWPYGVILNY | NKNTFRYGDN |
| 421 | DPGLSGDVQL | PAPMSVVNAQ | TQTAQYTDGE | NINTDTGRSW | LCTLRGYCTT | NCFPGRGCYN |
| 481 | NSTGYGESCN | QSLPGQKIHA | LYPFTQTNVL | GQSGKLGLLA | SHIPYDLSPN | NTIGDKDTDS |
| 541 | TNIVAKGIPV | EKGYASSGQK | VEIIREWING | ANVVQLSPGQ | SWGMDFTNST | GGQYMVRCRY |
| 601 | ASTNDTPIFF | NLVYDGGSNP | IYNQMTFPAT | KETPAHDSVD | NEILGIKGIN | GNYSLMNVKD |
| 661 | SVELPSGKFH | VFFTNNGSSA | IYLDRLEFVP | LDQPAAPTQS | TQPINYPITS | RLPHRSGEPP |
| 721 | AIIWEKSGNV | RGNQLTISAQ | GVPENSQIYL | SVGGDRQILD | RSNGFKLVNY | SPTYSFTNIQ |
| 781 | ASSSNLVDIT | SGTITGQVQV | SNL | | | |

*Fig. 3*

Cry14Aa1

| | | | | | | |
|---|---|---|---|---|---|---|
| 1 | MDCNLQSQQN | IPYNVLAIPV | SNVNALVDTA | GDLKKAWEEF | QKTGSFSLTA | LQQGFSASQG |
| 61 | GAFNYLTLLQ | SGISLAGSFV | PGGTFVAPIV | NMVIGWLWPH | ENKTADTENL | IKLIDEEIQK |
| 121 | QLNKALLDQD | RNNWTSFLES | IFDTSATVSN | ADIDAQWSGT | VDTTNRQQKT | PTTSDYLNVV |
| 181 | GKFDSADSSI | ITNENQIMNG | NFDVAAAPYF | VDGATLRLSL | YQSYIKFCNS | WIDAVGFSTN |
| 141 | DANTQKANLA | RTKLTMRSTI | NEYTQRVMKV | FKDSKNMPTI | GTNKFSVDAY | NVYVKGMTLN |
| 301 | VLDMVAIWSS | LYPNDYTSQT | AIEQTRVTFS | NMVGQEEGTD | GTLKIYNTFD | SLSYQHSLIP |
| 361 | NNNVNLISYY | TDELQNLELA | VYTPKGGSGY | AYPYGFILNY | ANSNYKYGDN | DPTGKPLNKQ |
| 421 | DGPIQQINAA | TQNSKYLDGE | TINGIGASLP | GYCTTGSSAT | EQPFSCTGTA | NSYKASCNPS |
| 481 | DTNQKINALY | AFTQTNVKGS | TGKLGVLASL | VPYDLNPKNV | FGELDSDTNN | VILKGIPAEK |
| 541 | GYFPNNARPT | VVKEWINGAS | AVPFYSGNTL | FMTATNLTAT | QYKIRIRYAN | PNSDTQISVL |
| 601 | ITQNGSQISN | SNLTLYSTTD | SSMSSNLPQN | VYVTGENGNY | TLLDLYSTTN | VLSTGDITLK |
| 661 | LTGGNQKIFI | DRIEFIPTMP | VPAPTNNTNN | NNGDNGNNNP | PHHGCAIAGT | QQLCSGPPKF |
| 721 | EQVSDLEKIT | TQVYMLFKSS | SYEELAIKVS | SYQINQVALK | VMALSDEKFC | EEKRLLRKLV |
| 781 | NKANQLLEAR | NLLVGGNFET | TQNWVLGTNA | YDNYDSFLFN | GNYLSLQPAS | GFFTSYAYQK |
| 841 | IDESTLKPYT | RYKVSGFIGQ | SNQVELIISR | YGKEIDKILN | VPYAGPLPIT | ADASITCCAP |
| 901 | EIDQCDGGQS | DSHFFNYSID | VGALHPELNP | GDEIGLKIVQ | SNGYISISNL | EIIEERPLTE |
| 961 | MEIQAVNRKD | QKWKRELLLE | CASVSELLQP | IDNQIDSLFK | DANWYNDILP | HVTYQTLKNI |
| 1021 | IVPDLPKLKH | WFIDHLPGEY | HEIEQKMKEA | LKHAFTQLDE | KNLIHNGHFA | TNLIDWQVEG |
| 1081 | DAFMKVLENN | ALALQLSNWD | SSVSQSIDIL | EFDEDKAYKL | RVYAQGSGTI | QFGNCEDEAI |
| 1141 | QFNTNSFVYK | EKIIYFDSPS | INLHIQSEGS | EFVVSSIDLV | ELSDDE | |

Fig. 4

Cry14Aa1

MTNPTILYPSYHNVLAHPIRLDSFFDPFVETFKDLKGAWEEFGKTGYMDPLKQHLQIAWD
TSQNGTVDYLALTKASISLIGLIPGADAVVPFINMFVDFIFPKLFGRGSQQNAQAQFFEL
IIEKVKELVDEDFRNFTLNNLLNYLDGMQTALSHFQNDVQIAICQGEQPGLMLDQTPTAC
TPTTDHLISVRESFKDARTTIETALPHFKNPNLSTNDNTPDFNSDTVLLTLPMYTTGATL
NLILHQGYIQFAERWKSVNYDESFINQTKVDLQRRIQDYSTTVSTTFEKFKPTLNPSNKE
SVNKYNRYVRSMTLQSLDIAATWPTLDNVNYPSNVDIQLDQTRLVFSDVAGPWEGNDNIT
SNIIDVLTPINTGIGFQESSDLRKFTYPRIELQSMQFHGQYVNSKSVEHCYSDGLKLNYK
NKTITAGVSNIDESNQNNKHNYGPVINSPITDINVNSQNSQYLDLNSVMVNGGQKVTGCS
PLSSNGNSNNAALPNQKINVIYSVQSNDKPEKHADTYRKWGYMSSHIPYDLVPENVIGDI
DPDTKQPSLLLKGFPAEKGYGDSIAYVSEPLNGANAVKLTSYQVLQMEVTNQTTQKYRIR
IRYATGGDTAASIWFHIIGPSGNDLTNEGHNFSSVSSRNKMFVQGNNGKYVLNILTDSIE
LPSGQQTILIQNTNSQDLFLDRIEFISLPSTSTPTSTNFVEPESLEKIINQVNQLFSSSS
QTELAHTVSDYKIDQVLKVNALSDDVFGVEKKALRKLVNQAKQLSKARNVLVGGNFEKG
HEWALSREATMVANHELFKGDHLLLPPPTLYPSYAYQKIDESKLKSNTRYTVSGFIAQSE
HLEVVSRYGKEVHDMLDIPYEEALPISSDESPNCCKPAACQCSSCDGSQSDSHFFSYSI
DVGSLQSDVNLGIEFGLRIAKPNGFAKISNLEIKEDRPLTEKEIKKVQRKEQKWKKAFNQ
EQAEVATTLQPTLDQINALYQNEDWNGSVHPASDYQHLSAVVPTLPKQRHWFMEGREGE
HVVLTQQFQQALDRAFQQIEEQNLTHNGNLANGLTDWTVTGDAQLTIFDEDPVLELAHWD
ASISQTIEIMDFEGRHRIQTACTWKRQRNSYRSTWRKRLETMTFNTTSFTTQEQTFYFEG
DTVDVHVQSENNTFLIDSVELIEIIEE

*Fig. 5A*

Cry21Aa2
(98% identical to Cry21Aa1)

MTNPTILYPSYHNVLAHPIRLDSFFDPFVETFKDLKSAWEEFGKTGYMDPLKQHLQIAWD
TSQNGTVDYLALTKASISLIGLIPGADAVVPFINMFVDFIFPKLFGRGSQQNAQAQFFEL
IIEKVKELVDEDFRNFTLNNLLNYLDGMQTALSHFQNDVQIAICQGEQPGLMLDQTPTAC
TPTTDHLISVRESFKDARTTIETALPHFKNPNLSTNDNTPDFNSDTVLLTLPMYTTAATL
NLILHQGYIQFAERWKSVNYDESFINQTKVDLQRRIQDYSTTVSTTFEKFKPTLNPSNKE
SVNKYNRYVRSMTLQSLDIAATWPTLDNVNYPSNVDIQLDQTRLVFSDVAGPWEGNDNIT
SNIIDVLTPINTGIGFQESSDLRKFTYPRIELQSMQFHGQYVNSKSVEHCYSDGLKLNYK
NKTITAGVSNIDESNQNNKHNYGPVINSPITDINVNSQNSQYLDLNSVMVNGGQKVAGCS
PLSSNGNSNNAALPNQKINVIYSVQSNDKPEKHADTYRKWGYMSSHIPYDLVPENVIGDI
DPDTKQPSLLLKGFPAEKGYGDSIAYVSEPLNGANAVKLTSYQVLKMEVTNQTTQKYRIR
IRYATGGDTAASIWFHIIGPSGNDLTNEGHNFSSVSSRNKMFVQGNNGKYVLNILTDSIE
LPSGQQTILIQNTNSQDLFLDRIEFISLPSTSTPTSTNFVEPESLEKIINQVNQLFSSSS
QTELAHTVSDYKIDQVVLKVNALSDDVFGVEKKALRKLVNQAKQLSKARNVLVGGNFEKG
HEWALSREATMVANHELFKGDHLLLPPPTLYPSYAYQKIDESKLKSNTRYTVSGFIAQSE
HLEVVVSRYGKEVHDMLDIPYEEALPISSDESPNCCKPAACQCSSCDGSQSDSHFFSYSI
DVGSLQSDVNLGIEFGLRIAKPNGFAKISNLEIKEDRPLTEKEIKKVQRKEQKWKKAFNQ
EQAEVATTLQPTLDQINALYQNEDWNGSVHPHVTYQHLSAVVVPTLPKQRHWFMEDREGE
HVVLTQQFQQALDRAFQQIEEQNLIHNGNFANGLTDWTVTGDAQLSIFDEDPVLELAHWD
ASISQTIEIMDFEEDTEYKLRVRGKGKGTVTVQHGEEELETMTFNSTSFTTQEQTFYFEG
DTVDVHVQSENNTFLIDSVELIEIIEE

*Fig. 5B*

MIIDSKTTLPRHSLIHTIKLNSNKKYGPGDMTNGNQFIISKQEWATIGAYIQTGLGLPVNEQQLRTHVNL
SQDISIPSDFSQLYDVYCSDKTSAEWWNKNLYPLIIKSANDIASYGFKVAGDPSIKKDGYFKKLQDELDN
IVDNNSDDDAIAKAIKDFKARCGILIKEAKQYEEAAKNIVTSLDQFLHGDQKKLEGVINIQKRLKEVQTA
LNQAHGESSPAHKELLEKVKNLKTTLERTIKAEQDLEKKVEYSFLLGPLLGFVVYEILENTAVQHIKNQI
DEIKEQLDSAQHDLDRDVKIIGMLNSINTDIDNLYSQGEAIKVFQKLQGIWATIGAQIENLRTTSLQEV
QDSDDADEIQIELEDASDAWLVVAQEARDFTLNAYSTNSRQNLPINVISDSCNCSTTNMTSNQYSNPTTN
MTSNQYMISHEYTSLPNNFMLSRNSNLEYKCPENNFMIYWYNNSDWYNNSDWYNN

SEQUENCE LISTING

```
<160> NUMBER OF SEQ ID NOS: 31

<210> SEQ ID NO 1
<211> LENGTH: 1245
<212> TYPE: PRT
<213> ORGANISM: Bacillus thuringiensis
<220> FEATURE:
<221> NAME/KEY: source
<223> OTHER INFORMATION: /note="Bacillus thuringiensis pesticidal
      crystal (Cry)"

<400> SEQUENCE: 1

Met Ala Thr Ile Asn Glu Leu Tyr Pro Val Pro Tyr Asn Val Leu Ala
1               5                   10                  15

His Pro Ile Lys Glu Val Asp Asp Pro Tyr Ser Trp Ser Asn Leu Leu
            20                  25                  30

Lys Gly Ile Gln Glu Gly Trp Glu Glu Trp Gly Lys Thr Gly Gln Lys
        35                  40                  45

Lys Leu Phe Glu Asp His Leu Thr Ile Ala Trp Asn Leu Tyr Lys Thr
    50                  55                  60

Gly Lys Leu Asp Tyr Phe Ala Leu Thr Lys Ala Ser Ile Ser Leu Ile
65                  70                  75                  80

Gly Phe Ile Pro Gly Ala Glu Ala Ala Val Pro Phe Ile Asn Met Phe
                85                  90                  95
```

-continued

```
Val Asp Phe Val Trp Pro Lys Leu Phe Gly Ala Asn Thr Glu Gly Lys
            100                 105                 110

Asp Gln Gln Leu Phe Asn Ala Ile Met Asp Ala Val Asn Lys Met Val
            115                 120                 125

Asp Asn Lys Phe Leu Ser Tyr Asn Leu Ser Thr Leu Asn Lys Thr Ile
            130                 135                 140

Glu Gly Leu Gln Gly Asn Leu Gly Leu Phe Gln Asn Ala Ile Gln Val
145                 150                 155                 160

Ala Ile Cys Gln Gly Ser Thr Pro Glu Arg Val Asn Phe Asp Gln Asn
                165                 170                 175

Cys Thr Pro Cys Asn Pro Asn Gln Pro Cys Lys Asp Asp Leu Asp Arg
            180                 185                 190

Val Ala Ser Arg Phe Asp Thr Ala Asn Ser Gln Phe Thr Gln His Leu
                195                 200                 205

Pro Glu Phe Lys Asn Pro Trp Ser Asp Glu Asn Ser Thr Gln Glu Phe
            210                 215                 220

Lys Arg Thr Ser Val Glu Leu Thr Leu Pro Met Tyr Thr Thr Val Ala
225                 230                 235                 240

Thr Leu His Leu Leu Leu Tyr Glu Gly Tyr Ile Glu Phe Met Thr Lys
                245                 250                 255

Trp Asn Phe His Asn Glu Gln Tyr Leu Asn Asn Leu Lys Val Glu Leu
            260                 265                 270

Gln Gln Leu Ile His Ser Tyr Ser Glu Thr Val Arg Thr Ser Phe Leu
            275                 280                 285

Gln Phe Leu Pro Thr Leu Asn Asn Arg Ser Lys Ser Ser Val Asn Ala
            290                 295                 300

Tyr Asn Arg Tyr Val Arg Asn Met Thr Val Asn Cys Leu Asp Ile Ala
305                 310                 315                 320

Ala Thr Trp Pro Thr Phe Asp Thr His Asn Tyr His Gln Gly Gly Lys
                325                 330                 335

Leu Asp Leu Thr Arg Ile Ile Leu Ser Asp Thr Ala Gly Pro Ile Glu
            340                 345                 350

Glu Tyr Thr Thr Gly Asp Lys Thr Ser Gly Pro Glu His Ser Asn Ile
            355                 360                 365

Thr Pro Asn Asn Ile Leu Asp Thr Pro Ser Pro Thr Tyr Gln His Ser
            370                 375                 380

Phe Val Ser Val Asp Ser Ile Val Tyr Ser Arg Lys Glu Leu Gln Gln
385                 390                 395                 400

Leu Asp Ile Ala Thr Tyr Ser Thr Asn Asn Ser Asn Asn Cys His Pro
                405                 410                 415

Tyr Gly Leu Arg Leu Ser Tyr Thr Asp Gly Ser Arg Tyr Asp Tyr Gly
            420                 425                 430

Asp Asn Gln Pro Asp Phe Thr Thr Ser Asn Asn Asn Tyr Cys His Asn
            435                 440                 445

Ser Tyr Thr Ala Pro Ile Thr Leu Val Asn Ala Arg His Leu Tyr Asn
            450                 455                 460

Ala Lys Gly Ser Leu Gln Asn Val Glu Ser Leu Val Val Ser Thr Val
465                 470                 475                 480

Asn Gly Gly Ser Gly Ser Cys Ile Cys Asp Ala Trp Ile Asn Tyr Leu
                485                 490                 495

Arg Pro Pro Gln Thr Ser Lys Asn Glu Ser Arg Pro Asp Gln Lys Ile
            500                 505                 510
```

-continued

```
Asn Val Leu Tyr Pro Ile Thr Glu Thr Val Asn Lys Gly Thr Gly
            515                 520                 525
Asn Leu Gly Val Ile Ser Ala Tyr Val Pro Met Glu Leu Val Pro Glu
530                 535                 540
Asn Val Ile Gly Asp Val Asn Ala Asp Thr Lys Leu Pro Leu Thr Gln
545                 550                 555                 560
Leu Lys Gly Phe Pro Phe Glu Lys Tyr Gly Glu Tyr Asn Asn Arg
                565                 570                 575
Gly Ile Ser Leu Val Arg Glu Trp Ile Asn Gly Asn Asn Ala Val Lys
                580                 585                 590
Leu Ser Asn Ser Gln Ser Val Gly Ile Gln Ile Thr Asn Gln Thr Lys
            595                 600                 605
Gln Lys Tyr Glu Ile Arg Cys Arg Tyr Ala Ser Lys Gly Asp Asn Asn
            610                 615                 620
Val Tyr Phe Asn Val Asp Leu Ser Glu Asn Pro Phe Arg Asn Ser Ile
625                 630                 635                 640
Ser Phe Gly Ser Thr Glu Ser Ser Val Val Gly Val Gln Gly Glu Asn
                645                 650                 655
Gly Lys Tyr Ile Leu Lys Ser Ile Thr Thr Val Glu Ile Pro Ala Gly
                660                 665                 670
Ser Phe Tyr Val His Ile Thr Asn Gln Gly Ser Ser Asp Leu Phe Leu
                675                 680                 685
Asp Arg Ile Glu Phe Val Pro Lys Ile Gln Phe Gln Phe Cys Asp Asn
            690                 695                 700
Asn Asn Leu His Cys Asp Cys Asn Asn Pro Val Asp Thr Asp Cys Thr
705                 710                 715                 720
Phe Cys Cys Val Cys Thr Ser Leu Thr Asp Cys Asp Cys Asn Asn Pro
                725                 730                 735
Arg Gly Leu Asp Cys Thr Leu Cys Cys Gln Val Glu Asn Gln Leu Pro
                740                 745                 750
Ser Phe Val Thr Leu Thr Asp Leu Gln Asn Ile Thr Thr Gln Val Asn
                755                 760                 765
Ala Leu Val Ala Ser Ser Glu His Asp Thr Leu Ala Thr Asp Val Ser
            770                 775                 780
Asp Tyr Glu Ile Glu Glu Val Val Leu Lys Val Asp Ala Leu Ser Gly
785                 790                 795                 800
Glu Val Phe Gly Lys Glu Lys Lys Ala Leu Arg Lys Leu Val Asn His
                805                 810                 815
Thr Lys Arg Leu Ser Lys Ala Arg Asn Leu Leu Ile Gly Gly Asn Phe
                820                 825                 830
Asp Asn Leu Asp Ala Trp Tyr Arg Gly Arg Asn Val Val Asn Val Ser
                835                 840                 845
Asp His Glu Leu Phe Lys Ser Asp His Val Leu Leu Pro Pro Thr
            850                 855                 860
Leu Tyr Ser Ser Tyr Met Phe Gln Lys Val Glu Glu Ser Lys Leu Lys
865                 870                 875                 880
Ala Asn Thr Arg Tyr Thr Val Ser Gly Phe Ile Ala His Ala Glu Asp
                885                 890                 895
Leu Glu Ile Val Val Ser Arg Tyr Gly Gln Glu Val Lys Lys Val Val
                900                 905                 910
Gln Val Pro Tyr Gly Glu Ala Phe Pro Leu Thr Ser Arg Gly Ala Ile
            915                 920                 925
Cys Cys Pro Pro Arg Ser Thr Ser Asn Gly Lys Pro Ala Asp Pro His
```

```
                    930                 935                 940
        Phe Phe Ser Tyr Ser Ile Asp Val Gly Thr Leu Asp Val Glu Ala Asn
        945                 950                 955                 960

Pro Gly Ile Glu Leu Gly Leu Arg Ile Val Glu Arg Thr Gly Met Ala
                            965                 970                 975

Arg Val Ser Asn Leu Glu Ile Arg Glu Asp Arg Pro Leu Lys Lys Asn
                        980                 985                 990

Glu Leu Arg Asn Val Gln Arg Ala Ala Arg Asn Trp Arg Thr Ala Tyr
                    995                 1000                1005

Asp Gln Glu Arg Ala Glu Val Thr Ala Leu Ile Gln Pro Val Leu
                1010                1015                1020

Asn Gln Ile Asn Ala Leu Tyr Glu Asn Glu Asp Trp Asn Gly Ala
                1025                1030                1035

Ile Arg Ser Gly Val Ser Tyr His Asp Leu Glu Ala Ile Val Leu
                1040                1045                1050

Pro Thr Leu Pro Lys Leu Asn His Trp Phe Met Ser Asp Met Leu
                1055                1060                1065

Gly Glu Gln Gly Ser Ile Leu Ala Gln Phe Gln Glu Ala Leu Asp
                1070                1075                1080

Arg Ala Tyr Thr Gln Leu Glu Glu Ser Thr Ile Leu His Asn Gly
                1085                1090                1095

His Phe Thr Thr Asp Ala Ala Asn Trp Thr Ile Glu Gly Asp Ala
                1100                1105                1110

His His Ala Ile Leu Glu Asp Gly Arg Arg Val Leu Arg Leu Pro
                1115                1120                1125

Asp Trp Ser Ser Ser Val Ser Gln Thr Ile Glu Ile Glu Asn Phe
                1130                1135                1140

Asp Pro Asp Lys Glu Tyr Gln Leu Val Phe His Ala Gln Gly Glu
                1145                1150                1155

Gly Thr Val Ser Leu Gln His Gly Glu Glu Gly Glu Tyr Val Glu
                1160                1165                1170

Thr His Pro His Lys Ser Ala Asn Phe Thr Thr Ser His Arg Gln
                1175                1180                1185

Gly Val Thr Phe Glu Thr Asn Lys Val Thr Val Glu Ile Thr Ser
                1190                1195                1200

Glu Asp Gly Glu Phe Leu Val Asp His Ile Ala Leu Val Glu Ala
                1205                1210                1215

Pro Leu Pro Thr Asp Asp Gln Ser Ser Asp Gly Asn Thr Thr Ser
                1220                1225                1230

Asn Thr Asn Ser Asn Thr Ser Met Asn Asn Gln
                1235                1240                1245

<210> SEQ ID NO 2
<211> LENGTH: 803
<212> TYPE: PRT
<213> ORGANISM: Bacillus thuringiensis
<220> FEATURE:
<221> NAME/KEY: source
<223> OTHER INFORMATION: /note="Bacillus thuringiensis pesticidal
      crystal"

<400> SEQUENCE: 2

Met Thr Cys Gln Leu Gln Ala Gln Pro Leu Ile Pro Tyr Asn Val Leu
1               5                   10                  15

Ala Gly Val Pro Thr Ser Asn Thr Gly Ser Pro Ile Gly Asn Ala Gly
            20                  25                  30
```

```
Asn Gln Phe Asp Gln Phe Glu Gln Thr Val Lys Glu Leu Lys Glu Ala
        35                  40                  45

Trp Glu Ala Phe Gln Lys Asn Gly Ser Phe Ser Leu Ala Ala Leu Glu
    50                  55                  60

Lys Gly Phe Asp Ala Ala Ile Gly Gly Ser Phe Asp Tyr Leu Gly
65                  70                  75                  80

Leu Val Gln Ala Gly Leu Gly Leu Val Gly Thr Leu Gly Ala Ala Ile
                85                  90                  95

Pro Gly Val Ser Val Ala Val Pro Leu Ile Ser Met Leu Val Gly Val
                100                 105                 110

Phe Trp Pro Lys Gly Thr Asn Asn Gln Glu Asn Leu Ile Thr Val Ile
            115                 120                 125

Asp Lys Glu Val Gln Arg Ile Leu Asp Glu Lys Leu Ser Asp Gln Leu
        130                 135                 140

Ile Lys Lys Leu Asn Ala Asp Leu Asn Ala Phe Thr Asp Leu Val Thr
145                 150                 155                 160

Arg Leu Glu Glu Val Ile Ile Asp Ala Thr Phe Glu Asn His Lys Pro
                165                 170                 175

Val Leu Gln Val Ser Lys Ser Asn Tyr Met Lys Val Asp Ser Ala Tyr
                180                 185                 190

Phe Ser Thr Gly Gly Ile Leu Thr Leu Gly Met Ser Asp Phe Leu Thr
            195                 200                 205

Asp Thr Tyr Ser Lys Leu Thr Phe Pro Leu Tyr Val Leu Gly Ala Thr
        210                 215                 220

Met Lys Leu Ser Ala Tyr His Ser Tyr Ile Gln Phe Gly Asn Thr Trp
225                 230                 235                 240

Leu Asn Lys Val Tyr Asp Leu Ser Ser Asp Glu Gly Lys Thr Met Ser
                245                 250                 255

Gln Ala Leu Ala Arg Ala Lys Gln His Met Arg Gln Asp Ile Ala Phe
            260                 265                 270

Tyr Thr Ser Gln Ala Leu Asn Met Phe Thr Gly Asn Leu Pro Ser Leu
        275                 280                 285

Ser Ser Asn Lys Tyr Ala Ile Asn Asp Tyr Asn Val Tyr Thr Arg Ala
290                 295                 300

Met Val Leu Asn Gly Leu Asp Ile Val Ala Thr Trp Pro Thr Leu Tyr
305                 310                 315                 320

Pro Asp Asp Tyr Ser Ser Gln Ile Lys Leu Glu Lys Thr Arg Val Ile
                325                 330                 335

Phe Ser Asp Met Val Gly Gln Ser Glu Ser Arg Asp Gly Ser Val Thr
            340                 345                 350

Ile Lys Asn Ile Phe Asp Asn Thr Asp Ser His Gln His Gly Ser Ile
        355                 360                 365

Gly Leu Asn Ser Ile Ser Tyr Phe Pro Asp Glu Leu Gln Lys Ala Gln
370                 375                 380

Leu Arg Met Tyr Asp Tyr Asn His Lys Pro Tyr Cys Thr Asp Cys Phe
385                 390                 395                 400

Cys Trp Pro Tyr Gly Val Ile Leu Asn Tyr Asn Lys Asn Thr Phe Arg
                405                 410                 415

Tyr Gly Asp Asn Asp Pro Gly Leu Ser Gly Asp Val Gln Leu Pro Ala
            420                 425                 430

Pro Met Ser Val Val Asn Ala Gln Thr Gln Thr Ala Gln Tyr Thr Asp
        435                 440                 445
```

Gly Glu Asn Ile Trp Thr Asp Thr Gly Arg Ser Trp Leu Cys Thr Leu
            450                 455                 460

Arg Gly Tyr Cys Thr Thr Asn Cys Phe Pro Gly Arg Gly Cys Tyr Asn
465                 470                 475                 480

Asn Ser Thr Gly Tyr Gly Glu Ser Cys Asn Gln Ser Leu Pro Gly Gln
            485                 490                 495

Lys Ile His Ala Leu Tyr Pro Phe Thr Gln Thr Asn Val Leu Gly Gln
            500                 505                 510

Ser Gly Lys Leu Gly Leu Leu Ala Ser His Ile Pro Tyr Asp Leu Ser
            515                 520                 525

Pro Asn Asn Thr Ile Gly Asp Lys Asp Thr Ser Thr Asn Ile Val
530                 535                 540

Ala Lys Gly Ile Pro Val Glu Lys Gly Tyr Ala Ser Gly Gln Lys
545                 550                 555                 560

Val Glu Ile Ile Arg Glu Trp Ile Asn Gly Ala Asn Val Val Gln Leu
            565                 570                 575

Ser Pro Gly Gln Ser Trp Gly Met Asp Phe Thr Asn Ser Thr Gly Gly
            580                 585                 590

Gln Tyr Met Val Arg Cys Arg Tyr Ala Ser Thr Asn Asp Thr Pro Ile
            595                 600                 605

Phe Phe Asn Leu Val Tyr Asp Gly Gly Ser Asn Pro Ile Tyr Asn Gln
610                 615                 620

Met Thr Phe Pro Ala Thr Lys Glu Thr Pro Ala His Asp Ser Val Asp
625                 630                 635                 640

Asn Lys Ile Leu Gly Ile Lys Gly Ile Asn Gly Asn Tyr Ser Leu Met
            645                 650                 655

Asn Val Lys Asp Ser Val Glu Leu Pro Ser Gly Lys Phe His Val Phe
            660                 665                 670

Phe Thr Asn Asn Gly Ser Ser Ala Ile Tyr Leu Asp Arg Leu Glu Phe
            675                 680                 685

Val Pro Leu Asp Gln Pro Ala Ala Pro Thr Gln Ser Thr Gln Pro Ile
            690                 695                 700

Asn Tyr Pro Ile Thr Ser Arg Leu Pro His Arg Ser Gly Glu Pro Pro
705                 710                 715                 720

Ala Ile Ile Trp Glu Lys Ser Gly Asn Val Arg Gly Asn Gln Leu Thr
            725                 730                 735

Ile Ser Ala Gln Gly Val Pro Glu Asn Ser Gln Ile Tyr Leu Ser Val
            740                 745                 750

Gly Gly Asp Arg Gln Ile Leu Asp Arg Ser Asn Gly Phe Lys Leu Val
            755                 760                 765

Asn Tyr Ser Pro Thr Tyr Ser Phe Thr Asn Ile Gln Ala Ser Ser Ser
770                 775                 780

Asn Leu Val Asp Ile Thr Ser Gly Thr Ile Thr Gly Gln Val Gln Val
785                 790                 795                 800

Ser Asn Leu

<210> SEQ ID NO 3
<211> LENGTH: 1186
<212> TYPE: PRT
<213> ORGANISM: Bacillus thuringiensis
<220> FEATURE:
<221> NAME/KEY: source
<223> OTHER INFORMATION: /note="Bacillus thuringiensis pesticidal crystal"

<400> SEQUENCE: 3

-continued

```
Met Asp Cys Asn Leu Gln Ser Gln Gln Asn Ile Pro Tyr Asn Val Leu
1               5                   10                  15

Ala Ile Pro Val Ser Asn Val Asn Ala Leu Val Asp Thr Ala Gly Asp
            20                  25                  30

Leu Lys Lys Ala Trp Glu Glu Phe Gln Lys Thr Gly Ser Phe Ser Leu
        35                  40                  45

Thr Ala Leu Gln Gln Gly Phe Ser Ala Ser Gln Gly Gly Ala Phe Asn
    50                  55                  60

Tyr Leu Thr Leu Leu Gln Ser Gly Ile Ser Leu Ala Gly Ser Phe Val
65              70                  75                  80

Pro Gly Gly Thr Phe Val Ala Pro Ile Val Asn Met Val Ile Gly Trp
                85                  90                  95

Leu Trp Pro His Lys Asn Lys Thr Ala Asp Thr Glu Asn Leu Ile Lys
            100                 105                 110

Leu Ile Asp Glu Glu Ile Gln Lys Gln Leu Asn Lys Ala Leu Leu Asp
        115                 120                 125

Gln Asp Arg Asn Asn Trp Thr Ser Phe Leu Glu Ser Ile Phe Asp Thr
    130                 135                 140

Ser Ala Thr Val Ser Asn Ala Ile Ile Asp Ala Gln Trp Ser Gly Thr
145                 150                 155                 160

Val Asp Thr Thr Asn Arg Gln Gln Lys Thr Pro Thr Thr Ser Asp Tyr
                165                 170                 175

Leu Asn Val Val Gly Lys Phe Asp Ser Ala Asp Ser Ser Ile Ile Thr
            180                 185                 190

Asn Glu Asn Gln Ile Met Asn Gly Asn Phe Asp Val Ala Ala Ala Pro
        195                 200                 205

Tyr Phe Val Ile Gly Ala Thr Leu Arg Leu Ser Leu Tyr Gln Ser Tyr
    210                 215                 220

Ile Lys Phe Cys Asn Ser Trp Ile Asp Ala Val Gly Phe Ser Thr Asn
225                 230                 235                 240

Asp Ala Asn Thr Gln Lys Ala Asn Leu Ala Arg Thr Lys Leu Thr Met
                245                 250                 255

Arg Thr Thr Ile Asn Glu Tyr Thr Gln Arg Val Met Lys Val Phe Lys
            260                 265                 270

Asp Ser Lys Asn Met Pro Thr Ile Gly Thr Asn Lys Phe Ser Val Asp
        275                 280                 285

Ala Tyr Asn Val Tyr Val Lys Gly Met Thr Leu Asn Val Leu Asp Met
    290                 295                 300

Val Ala Ile Trp Ser Ser Leu Tyr Pro Asn Asp Tyr Thr Ser Gln Thr
305                 310                 315                 320

Ala Ile Glu Gln Thr Arg Val Thr Phe Ser Asn Met Val Gly Gln Glu
                325                 330                 335

Glu Gly Thr Asp Gly Thr Leu Lys Ile Tyr Asn Thr Phe Asp Ser Leu
            340                 345                 350

Ser Tyr Gln His Ser Leu Ile Pro Asn Asn Val Asn Leu Ile Ser
        355                 360                 365

Tyr Tyr Thr Asp Glu Leu Gln Asn Leu Glu Leu Ala Val Tyr Thr Pro
    370                 375                 380

Lys Gly Gly Ser Gly Tyr Ala Tyr Pro Tyr Gly Phe Ile Leu Asn Tyr
385                 390                 395                 400

Ala Asn Ser Asn Tyr Lys Tyr Gly Asp Asn Asp Pro Thr Gly Lys Pro
                405                 410                 415
```

```
Leu Asn Lys Gln Asp Gly Pro Ile Gln Gln Ile Asn Ala Ala Thr Gln
            420                 425                 430

Asn Ser Lys Tyr Leu Asp Gly Glu Thr Ile Asn Gly Ile Gly Ala Ser
            435                 440                 445

Leu Pro Gly Tyr Cys Thr Thr Gly Cys Ser Ala Thr Glu Gln Pro Phe
450                 455                 460

Ser Cys Thr Ser Thr Ala Asn Ser Tyr Lys Ala Ser Cys Asn Pro Ser
465                 470                 475                 480

Asp Thr Asn Gln Lys Ile Asn Ala Leu Tyr Ala Phe Thr Gln Thr Asn
            485                 490                 495

Val Lys Gly Ser Thr Gly Lys Leu Gly Val Leu Ala Ser Leu Val Pro
        500                 505                 510

Tyr Asp Leu Asn Pro Lys Asn Val Phe Gly Glu Leu Asp Ser Asp Thr
        515                 520                 525

Asn Asn Val Ile Leu Lys Gly Ile Pro Ala Glu Lys Gly Tyr Phe Pro
    530                 535                 540

Asn Asn Ala Arg Pro Thr Val Val Lys Glu Trp Ile Asn Gly Ala Ser
545                 550                 555                 560

Ala Val Pro Phe Tyr Ser Gly Asn Thr Leu Phe Met Thr Ala Thr Asn
                565                 570                 575

Leu Thr Ala Thr Gln Tyr Lys Ile Arg Ile Arg Tyr Ala Asn Pro Asn
            580                 585                 590

Ser Asp Thr Gln Ile Gly Val Leu Ile Thr Gln Asn Gly Ser Gln Ile
        595                 600                 605

Ser Asn Ser Asn Leu Thr Leu Tyr Ser Thr Thr Asp Ser Ser Met Ser
    610                 615                 620

Ser Asn Leu Pro Gln Asn Val Tyr Val Thr Gly Glu Asn Gly Asn Tyr
625                 630                 635                 640

Thr Leu Leu Asp Leu Tyr Ser Thr Thr Asn Val Leu Ser Thr Gly Asp
                645                 650                 655

Ile Thr Leu Lys Leu Thr Gly Gly Asn Gln Lys Ile Phe Ile Asp Arg
            660                 665                 670

Ile Glu Phe Ile Pro Thr Met Pro Val Pro Ala Pro Thr Asn Asn Thr
        675                 680                 685

Asn Asn Asn Asn Gly Asp Asn Gly Asn Asn Asn Pro Pro His His Gly
    690                 695                 700

Cys Ala Ile Ala Gly Thr Gln Gln Leu Cys Ser Gly Pro Pro Lys Phe
705                 710                 715                 720

Glu Gln Val Ser Asp Leu Glu Lys Ile Thr Thr Gln Val Tyr Met Leu
                725                 730                 735

Phe Lys Ser Ser Tyr Glu Glu Leu Ala Leu Lys Val Ser Ser Tyr
            740                 745                 750

Gln Ile Asn Gln Val Ala Leu Lys Val Met Ala Leu Ser Asp Glu Lys
            755                 760                 765

Phe Cys Glu Glu Lys Arg Leu Leu Arg Lys Leu Val Asn Lys Ala Asn
770                 775                 780

Gln Leu Leu Glu Ala Arg Asn Leu Leu Val Gly Gly Asn Phe Glu Thr
785                 790                 795                 800

Thr Gln Asn Trp Val Leu Gly Thr Asn Ala Tyr Ile Asn Tyr Asp Ser
                805                 810                 815

Phe Leu Phe Asn Gly Asn Tyr Leu Ser Leu Gln Pro Ala Ser Gly Phe
            820                 825                 830

Phe Thr Ser Tyr Ala Tyr Gln Lys Ile Asp Glu Ser Thr Leu Lys Pro
```

```
                835                 840                 845
Tyr Thr Arg Tyr Lys Val Ser Gly Phe Ile Gly Gln Ser Asn Gln Val
    850                 855                 860
Glu Leu Ile Ile Ser Arg Tyr Gly Lys Glu Ile Asp Lys Ile Leu Asn
865                 870                 875                 880
Val Pro Tyr Ala Gly Pro Leu Pro Ile Thr Ala Asp Ala Ser Ile Thr
                885                 890                 895
Cys Cys Ala Pro Glu Ile Asp Gln Cys Asp Gly Gly Gln Ser Asp Ser
            900                 905                 910
His Phe Phe Asn Tyr Ser Ile Asp Val Gly Ala Leu His Pro Glu Leu
        915                 920                 925
Asn Pro Gly Ile Glu Ile Gly Leu Lys Ile Val Gln Ser Asn Gly Tyr
    930                 935                 940
Ile Thr Ile Ser Asn Leu Glu Ile Ile Glu Glu Arg Pro Leu Thr Glu
945                 950                 955                 960
Met Glu Ile Gln Ala Val Asn Arg Lys Asp Gln Lys Trp Lys Arg Glu
                965                 970                 975
Lys Leu Leu Glu Cys Ala Ser Val Ser Glu Leu Leu Gln Pro Ile Ile
            980                 985                 990
Asn Gln Ile Asp Ser Leu Phe Lys  Asp Ala Asn Trp Tyr  Asn Asp Ile
        995                 1000                1005
Leu Pro His Val Thr Tyr Gln  Thr Leu Lys Asn Ile  Ile Val Pro
    1010                1015                1020
Asp Leu Pro Lys Leu Lys His  Trp Phe Ile Asp His  Leu Pro Gly
    1025                1030                1035
Glu Tyr His Glu Ile Glu Gln  Lys Met Lys Glu Ala  Leu Lys His
    1040                1045                1050
Ala Phe Thr Gln Leu Asp Glu  Lys Asn Leu Ile His  Asn Gly His
    1055                1060                1065
Phe Ala Thr Asn Leu Ile Asp  Trp Gln Val Glu Gly  Asp Ala Arg
    1070                1075                1080
Met Lys Val Leu Glu Asn Asn  Ala Leu Ala Leu Gln  Leu Ser Asn
    1085                1090                1095
Trp Asp Ser Ser Val Ser Gln  Ser Ile Asp Ile Leu  Glu Phe Asp
    1100                1105                1110
Glu Asp Lys Ala Tyr Lys Leu  Arg Val Tyr Ala Gln  Gly Ser Gly
    1115                1120                1125
Thr Ile Gln Phe Gly Asn Cys  Glu Asp Glu Ala Ile  Gln Phe Asn
    1130                1135                1140
Thr Asn Ser Phe Val Tyr Lys  Glu Lys Ile Ile Tyr  Phe Asp Thr
    1145                1150                1155
Pro Ser Ile Asn Leu His Ile  Gln Ser Glu Gly Ser  Glu Phe Val
    1160                1165                1170
Val Ser Ser Ile Asp Leu Val  Glu Leu Ser Asp Glu
    1175                1180                1185

<210> SEQ ID NO 4
<211> LENGTH: 1167
<212> TYPE: PRT
<213> ORGANISM: Bacillus thuringiensis
<220> FEATURE:
<221> NAME/KEY: source
<223> OTHER INFORMATION: /note="Bacillus thuringiensis pesticidal
      crystal"

<400> SEQUENCE: 4
```

```
Met Thr Asn Pro Thr Ile Leu Tyr Pro Ser Tyr His Asn Val Leu Ala
 1               5                  10                  15

His Pro Ile Arg Leu Asp Ser Phe Phe Asp Pro Phe Val Glu Thr Phe
             20                  25                  30

Lys Asp Leu Lys Gly Ala Trp Glu Glu Phe Gly Lys Thr Gly Tyr Met
             35                  40                  45

Asp Pro Leu Lys Gln His Leu Gln Ile Ala Trp Asp Thr Ser Gln Asn
 50                  55                  60

Gly Thr Val Asp Tyr Leu Ala Leu Thr Lys Ala Ser Ile Ser Leu Ile
 65                  70                  75                  80

Gly Leu Ile Pro Gly Ala Asp Ala Val Pro Phe Ile Asn Met Phe
             85                  90                  95

Val Asp Phe Ile Phe Pro Lys Leu Phe Gly Arg Gly Ser Gln Gln Asn
             100                 105                 110

Ala Gln Ala Gln Phe Phe Glu Leu Ile Ile Glu Lys Val Lys Glu Leu
         115                 120                 125

Val Asp Glu Asp Phe Arg Asn Phe Thr Leu Asn Asn Leu Leu Asn Tyr
         130                 135                 140

Leu Asp Gly Met Gln Thr Ala Leu Ser His Phe Gln Asn Asp Val Gln
145                 150                 155                 160

Ile Ala Ile Cys Gln Gly Glu Gln Pro Gly Leu Met Leu Asp Gln Thr
                 165                 170                 175

Pro Thr Ala Cys Thr Pro Thr Asp His Leu Ile Ser Val Arg Glu
                 180                 185                 190

Ser Phe Lys Asp Ala Arg Thr Thr Ile Glu Thr Ala Leu Pro His Phe
         195                 200                 205

Lys Asn Pro Met Leu Ser Thr Asn Asp Asn Thr Pro Asp Phe Asn Ser
         210                 215                 220

Asp Thr Val Leu Leu Thr Leu Pro Met Tyr Thr Thr Gly Ala Thr Leu
225                 230                 235                 240

Asn Leu Ile Leu His Gln Gly Tyr Ile Gln Phe Ala Glu Arg Trp Lys
                 245                 250                 255

Ser Val Asn Tyr Asp Glu Ser Phe Ile Asn Gln Thr Lys Val Asp Leu
                 260                 265                 270

Gln Arg Arg Ile Gln Asp Tyr Ser Thr Thr Val Ser Thr Thr Phe Glu
             275                 280                 285

Lys Phe Lys Pro Thr Leu Asn Pro Ser Asn Lys Glu Ser Val Asn Lys
         290                 295                 300

Tyr Asn Arg Tyr Val Arg Ser Met Thr Leu Gln Ser Leu Asp Ile Ala
305                 310                 315                 320

Ala Thr Trp Pro Thr Leu Asp Asn Val Asn Tyr Pro Ser Asn Val Asp
                 325                 330                 335

Ile Gln Leu Asp Gln Thr Arg Leu Val Phe Ser Asp Val Ala Gly Pro
             340                 345                 350

Trp Glu Gly Asn Asp Asn Ile Thr Ser Asn Ile Ile Asp Val Leu Thr
                 355                 360                 365

Pro Ile Asn Thr Gly Ile Gly Phe Gln Glu Ser Ser Asp Leu Arg Lys
         370                 375                 380

Phe Thr Tyr Pro Arg Ile Glu Leu Gln Ser Met Gln Phe His Gly Gln
385                 390                 395                 400

Tyr Val Asn Ser Lys Ser Val Glu His Cys Tyr Ser Asp Gly Leu Lys
                 405                 410                 415
```

```
Leu Asn Tyr Lys Asn Lys Thr Ile Thr Ala Gly Val Ser Asn Ile Asp
                420                 425                 430

Glu Ser Asn Gln Asn Asn Lys His Asn Tyr Gly Pro Val Ile Asn Ser
                435                 440                 445

Pro Ile Thr Asp Ile Asn Val Asn Ser Gln Asn Ser Gln Tyr Leu Asp
            450                 455                 460

Leu Asn Ser Val Met Val Asn Gly Gly Gln Lys Val Thr Gly Cys Ser
465                 470                 475                 480

Pro Leu Ser Ser Asn Gly Asn Ser Asn Ala Ala Leu Pro Asn Gln
                485                 490                 495

Lys Ile Asn Val Ile Tyr Ser Val Gln Ser Asn Asp Lys Pro Glu Lys
            500                 505                 510

His Ala Asp Thr Tyr Arg Lys Trp Gly Tyr Met Ser Ser His Ile Pro
            515                 520                 525

Tyr Asp Leu Val Pro Glu Asn Val Ile Gly Asp Ile Asp Pro Asp Thr
            530                 535                 540

Lys Gln Pro Ser Leu Leu Leu Lys Gly Phe Pro Ala Glu Lys Gly Tyr
545                 550                 555                 560

Gly Asp Ser Ile Ala Tyr Val Ser Glu Pro Leu Asn Gly Ala Asn Ala
                565                 570                 575

Val Lys Leu Thr Ser Tyr Gln Val Leu Gln Met Glu Val Thr Asn Gln
                580                 585                 590

Thr Thr Gln Lys Tyr Arg Ile Arg Ile Arg Tyr Ala Thr Gly Gly Asp
            595                 600                 605

Thr Ala Ala Ser Ile Trp Phe His Ile Ile Gly Pro Ser Gly Asn Asp
            610                 615                 620

Leu Thr Asn Glu Gly His Asn Phe Ser Val Ser Ser Arg Asn Lys
625                 630                 635                 640

Met Phe Val Gln Gly Asn Asn Gly Lys Tyr Val Leu Asn Ile Leu Thr
                645                 650                 655

Asp Ser Ile Glu Leu Pro Ser Gly Gln Gln Thr Ile Leu Ile Gln Asn
            660                 665                 670

Thr Asn Ser Gln Asp Leu Phe Leu Asp Arg Ile Glu Phe Ile Ser Leu
            675                 680                 685

Pro Ser Thr Ser Thr Pro Thr Ser Thr Asn Phe Val Glu Pro Glu Ser
690                 695                 700

Leu Glu Lys Ile Ile Asn Gln Val Asn Gln Leu Phe Ser Ser Ser Ser
705                 710                 715                 720

Gln Thr Glu Leu Ala His Thr Val Ser Asp Tyr Lys Ile Asp Gln Val
            725                 730                 735

Val Leu Lys Val Asn Ala Leu Ser Asp Asp Val Phe Gly Val Glu Lys
            740                 745                 750

Lys Ala Leu Arg Lys Leu Val Asn Gln Ala Lys Gln Leu Ser Lys Ala
            755                 760                 765

Arg Asn Val Leu Val Gly Gly Asn Phe Glu Lys Gly His Glu Trp Ala
770                 775                 780

Leu Ser Arg Glu Ala Thr Met Val Ala Asn His Glu Leu Phe Lys Gly
785                 790                 795                 800

Asp His Leu Leu Leu Pro Pro Thr Leu Tyr Pro Ser Tyr Ala Tyr
                805                 810                 815

Gln Lys Ile Asp Glu Ser Lys Leu Lys Ser Asn Thr Arg Tyr Thr Val
            820                 825                 830

Ser Gly Phe Ile Ala Gln Ser Glu His Leu Glu Val Val Ser Arg
```

```
                835                 840                 845
Tyr Gly Lys Glu Val His Asp Met Leu Asp Ile Pro Tyr Glu Glu Ala
    850                 855                 860
Leu Pro Ile Ser Ser Asp Glu Ser Pro Asn Cys Cys Lys Pro Ala Ala
865                 870                 875                 880
Cys Gln Cys Ser Ser Cys Asp Gly Ser Gln Ser Asp Ser His Phe Phe
                885                 890                 895
Ser Tyr Ser Ile Asp Val Gly Ser Leu Gln Ser Asp Val Asn Leu Gly
            900                 905                 910
Ile Glu Phe Gly Leu Arg Ile Ala Lys Pro Asn Gly Phe Ala Lys Ile
        915                 920                 925
Ser Asn Leu Glu Ile Lys Glu Asp Arg Pro Leu Thr Glu Lys Glu Ile
    930                 935                 940
Lys Lys Val Gln Arg Lys Glu Gln Lys Trp Lys Lys Ala Phe Asn Gln
945                 950                 955                 960
Glu Gln Ala Glu Val Ala Thr Thr Leu Gln Pro Thr Leu Asp Gln Ile
                965                 970                 975
Asn Ala Leu Tyr Gln Asn Glu Asp Trp Asn Gly Ser Val His Pro Ala
            980                 985                 990
Ser Asp Tyr Gln His Leu Ser Ala Val Val Val Pro Thr Leu Pro Lys
        995                 1000                1005
Gln Arg His Trp Phe Met Glu Gly Arg Glu Gly Glu His Val Val
    1010                1015                1020
Leu Thr Gln Gln Phe Gln Gln Ala Leu Asp Arg Ala Phe Gln Gln
    1025                1030                1035
Ile Glu Glu Gln Asn Leu Ile His Asn Gly Asn Leu Ala Asn Gly
    1040                1045                1050
Leu Thr Asp Trp Thr Val Thr Gly Asp Ala Gln Leu Thr Ile Phe
    1055                1060                1065
Asp Glu Asp Pro Val Leu Glu Leu Ala His Trp Asp Ala Ser Ile
    1070                1075                1080
Ser Gln Thr Ile Glu Ile Met Asp Phe Glu Gly Arg His Arg Ile
    1085                1090                1095
Gln Thr Ala Cys Thr Trp Lys Arg Gln Arg Asn Ser Tyr Arg Ser
    1100                1105                1110
Thr Trp Arg Lys Arg Leu Glu Thr Met Thr Phe Asn Thr Thr Ser
    1115                1120                1125
Phe Thr Thr Gln Glu Gln Thr Phe Tyr Phe Glu Gly Asp Thr Val
    1130                1135                1140
Asp Val His Val Gln Ser Glu Asn Asn Thr Phe Leu Ile Asp Ser
    1145                1150                1155
Val Glu Leu Ile Glu Ile Ile Glu Glu
    1160                1165

<210> SEQ ID NO 5
<211> LENGTH: 1167
<212> TYPE: PRT
<213> ORGANISM: Bacillus thuringiensis
<220> FEATURE:
<221> NAME/KEY: source
<223> OTHER INFORMATION: /note="Bacillus thuringiensis pesticidal
      crystal"

<400> SEQUENCE: 5

Met Thr Asn Pro Thr Ile Leu Tyr Pro Ser Tyr His Asn Val Leu Ala
1               5                   10                  15
```

```
His Pro Ile Arg Leu Asp Ser Phe Phe Asp Pro Phe Val Glu Thr Phe
             20                  25                  30
Lys Asp Leu Lys Gly Ala Trp Glu Glu Phe Gly Lys Thr Gly Tyr Met
         35                  40                  45
Asp Pro Leu Lys Gln His Leu Gln Ile Ala Trp Asp Thr Ser Gln Asn
 50                  55                  60
Gly Thr Val Asp Tyr Leu Ala Leu Thr Lys Ala Ser Ile Ser Leu Ile
 65                  70                  75                  80
Gly Leu Ile Pro Gly Ala Asp Ala Val Val Pro Phe Ile Asn Met Phe
                 85                  90                  95
Val Asp Phe Ile Phe Pro Lys Leu Phe Gly Arg Gly Ser Gln Gln Asn
            100                 105                 110
Ala Gln Ala Gln Phe Phe Glu Leu Ile Ile Glu Lys Val Lys Glu Leu
        115                 120                 125
Val Asp Glu Asp Phe Arg Asn Phe Thr Leu Asn Asn Leu Leu Asn Tyr
130                 135                 140
Leu Asp Gly Met Gln Thr Ala Leu Ser His Phe Gln Asn Asp Val Gln
145                 150                 155                 160
Ile Ala Ile Cys Gln Gly Glu Gln Pro Gly Leu Met Leu Asp Gln Thr
                165                 170                 175
Pro Thr Ala Cys Thr Pro Thr Thr Asp His Leu Ile Ser Val Arg Glu
            180                 185                 190
Ser Phe Lys Asp Ala Arg Thr Thr Ile Glu Thr Ala Leu Pro His Phe
        195                 200                 205
Lys Asn Pro Met Leu Ser Thr Asn Asp Asn Thr Pro Asp Phe Asn Ser
210                 215                 220
Asp Thr Val Leu Leu Thr Leu Pro Met Tyr Thr Thr Ala Ala Thr Leu
225                 230                 235                 240
Asn Leu Ile Leu His Gln Gly Tyr Ile Gln Phe Ala Glu Arg Trp Lys
                245                 250                 255
Ser Val Asn Tyr Asp Glu Ser Phe Ile Asn Gln Thr Lys Val Asp Leu
            260                 265                 270
Gln Arg Arg Ile Gln Asp Tyr Ser Thr Thr Val Ser Thr Thr Phe Glu
        275                 280                 285
Lys Phe Lys Pro Thr Leu Asn Pro Ser Asn Lys Glu Ser Val Asn Lys
290                 295                 300
Tyr Asn Arg Tyr Val Arg Ser Met Thr Leu Gln Ser Leu Asp Ile Ala
305                 310                 315                 320
Ala Thr Trp Pro Thr Leu Asp Asn Val Asn Tyr Pro Ser Asn Val Asp
                325                 330                 335
Ile Gln Leu Asp Gln Thr Arg Leu Val Phe Ser Asp Val Ala Gly Pro
            340                 345                 350
Trp Glu Gly Asn Asp Asn Ile Thr Ser Asn Ile Ile Asp Val Leu Thr
        355                 360                 365
Pro Ile Asn Thr Gly Ile Gly Phe Gln Glu Ser Ser Asp Leu Arg Lys
370                 375                 380
Phe Thr Tyr Pro Arg Ile Glu Leu Gln Ser Met Gln Phe His Gly Gln
385                 390                 395                 400
Tyr Val Asn Ser Lys Ser Val Glu His Cys Tyr Ser Asp Gly Leu Lys
                405                 410                 415
Leu Asn Tyr Lys Asn Lys Thr Ile Thr Ala Gly Val Ser Asn Ile Asp
            420                 425                 430
```

```
Glu Ser Asn Gln Asn Asn Lys His Asn Tyr Gly Pro Val Ile Asn Ser
            435                 440                 445

Pro Ile Thr Asp Ile Asn Val Asn Ser Gln Asn Ser Gln Tyr Leu Asp
450                 455                 460

Leu Asn Ser Val Met Val Asn Gly Gly Gln Lys Val Ala Gly Cys Ser
465                 470                 475                 480

Pro Leu Ser Ser Asn Gly Asn Ser Asn Ala Ala Leu Pro Asn Gln
                485                 490                 495

Lys Ile Asn Val Ile Tyr Ser Val Gln Ser Asn Asp Lys Pro Glu Lys
                500                 505                 510

His Ala Asp Thr Tyr Arg Lys Trp Gly Tyr Met Ser Ser His Ile Pro
            515                 520                 525

Tyr Asp Leu Val Pro Glu Asn Val Ile Gly Asp Ile Asp Pro Asp Thr
            530                 535                 540

Lys Gln Pro Ser Leu Leu Leu Lys Gly Phe Pro Ala Glu Lys Gly Tyr
545                 550                 555                 560

Gly Asp Ser Ile Ala Tyr Val Ser Glu Pro Leu Asn Gly Ala Asn Ala
                565                 570                 575

Val Lys Leu Thr Ser Tyr Gln Val Leu Lys Met Glu Val Thr Asn Gln
            580                 585                 590

Thr Thr Gln Lys Tyr Arg Ile Arg Ile Arg Tyr Ala Thr Gly Gly Asp
            595                 600                 605

Thr Ala Ala Ser Ile Trp Phe His Ile Ile Gly Pro Ser Gly Asn Asp
610                 615                 620

Leu Thr Asn Glu Gly His Asn Phe Ser Ser Val Ser Ser Arg Asn Lys
625                 630                 635                 640

Met Phe Val Gln Gly Asn Asn Gly Lys Tyr Val Leu Asn Ile Leu Thr
                645                 650                 655

Asp Ser Ile Glu Leu Pro Ser Gly Gln Gln Thr Ile Leu Ile Gln Asn
                660                 665                 670

Thr Asn Ser Gln Asp Leu Phe Leu Asp Arg Ile Glu Phe Ile Ser Leu
            675                 680                 685

Pro Ser Thr Ser Thr Pro Thr Ser Thr Asn Phe Val Glu Pro Glu Ser
690                 695                 700

Leu Glu Lys Ile Ile Asn Gln Val Asn Gln Leu Phe Ser Ser Ser Ser
705                 710                 715                 720

Gln Thr Glu Leu Ala His Thr Val Ser Asp Tyr Lys Ile Asp Gln Val
                725                 730                 735

Val Leu Lys Val Asn Ala Leu Ser Asp Asp Val Phe Gly Val Glu Lys
            740                 745                 750

Lys Ala Leu Arg Lys Leu Val Asn Gln Ala Lys Gln Leu Ser Lys Ala
            755                 760                 765

Arg Asn Val Leu Val Gly Gly Asn Phe Glu Lys Gly His Glu Trp Ala
770                 775                 780

Leu Ser Arg Glu Ala Thr Met Val Ala Asn His Glu Leu Phe Lys Gly
785                 790                 795                 800

Asp His Leu Leu Leu Pro Pro Thr Leu Tyr Pro Ser Tyr Ala Tyr
                805                 810                 815

Gln Lys Ile Asp Glu Ser Lys Leu Lys Ser Asn Thr Arg Tyr Thr Val
            820                 825                 830

Ser Gly Phe Ile Ala Gln Ser Glu His Leu Glu Val Val Ser Arg
            835                 840                 845

Tyr Gly Lys Glu Val His Asp Met Leu Asp Ile Pro Tyr Glu Glu Ala
```

```
Leu Pro Ile Ser Ser Asp Glu Ser Pro Asn Cys Cys Lys Pro Ala Ala
865                 870                 875                 880

Cys Gln Cys Ser Ser Cys Asp Gly Ser Gln Ser Asp Ser His Phe Phe
            885                 890                 895

Ser Tyr Ser Ile Asp Val Gly Ser Leu Gln Ser Asp Val Asn Leu Gly
        900                 905                 910

Ile Glu Phe Gly Leu Arg Ile Ala Lys Pro Asn Gly Phe Ala Lys Ile
    915                 920                 925

Ser Asn Leu Glu Ile Lys Glu Asp Arg Pro Leu Thr Glu Lys Glu Ile
930                 935                 940

Lys Lys Val Gln Arg Lys Glu Gln Lys Trp Lys Lys Ala Phe Asn Gln
945                 950                 955                 960

Glu Gln Ala Glu Val Ala Thr Thr Leu Gln Pro Thr Leu Asp Gln Ile
                965                 970                 975

Asn Ala Leu Tyr Gln Asn Glu Asp Trp Asn Gly Ser Val His Pro His
            980                 985                 990

Val Thr Tyr Gln His Leu Ser Ala Val Val Val Pro Thr Leu Pro Lys
        995                 1000                1005

Gln Arg His Trp Phe Met Glu Asp Arg Glu Gly Glu His Val Val
    1010                1015                1020

Leu Thr Gln Gln Phe Gln Gln Ala Leu Asp Arg Ala Phe Gln Gln
    1025                1030                1035

Ile Glu Glu Gln Asn Leu Ile His Asn Gly Asn Phe Ala Asn Gly
    1040                1045                1050

Leu Thr Asp Trp Thr Val Thr Gly Asp Ala Gln Leu Thr Ile Phe
    1055                1060                1065

Asp Glu Asp Pro Val Leu Glu Leu Ala His Trp Asp Ala Ser Ile
    1070                1075                1080

Ser Gln Thr Ile Glu Ile Met Asp Phe Glu Glu Asp Thr Glu Tyr
    1085                1090                1095

Lys Leu Arg Val Arg Gly Lys Gly Lys Gly Thr Val Thr Val Gln
    1100                1105                1110

His Gly Glu Glu Glu Leu Glu Thr Met Thr Phe Asn Thr Thr Ser
    1115                1120                1125

Phe Thr Thr Gln Glu Gln Thr Phe Tyr Phe Glu Gly Asp Thr Val
    1130                1135                1140

Asp Val His Val Gln Ser Glu Asn Asn Thr Phe Leu Ile Asp Ser
    1145                1150                1155

Val Glu Leu Ile Glu Ile Glu Glu
    1160                1165

<210> SEQ ID NO 6
<211> LENGTH: 475
<212> TYPE: PRT
<213> ORGANISM: Bacillus thuringiensis
<220> FEATURE:
<221> NAME/KEY: source
<223> OTHER INFORMATION: /note="Bacillus thuringiensis pesticidal
      crystal"

<400> SEQUENCE: 6

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30
```

```
Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
                100                 105                 110

Ala Ser Tyr Gly Phe Lys Val Ala Gly Asp Pro Ser Ile Lys Lys Asp
            115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
                180                 185                 190

Lys Leu Glu Gly Val Ile Asn Ile Gln Lys Arg Leu Lys Glu Val Gln
            195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
                260                 265                 270

Val Gln His Ile Lys Asn Gln Ile Asp Glu Ile Lys Lys Gln Leu Asp
    275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
    355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Gln Tyr Met Ile Ser His Glu Tyr
            420                 425                 430

Thr Ser Leu Pro Asn Asn Phe Met Leu Ser Arg Asn Ser Asn Leu Glu
            435                 440                 445
```

-continued

```
Tyr Lys Cys Pro Glu Asn Asn Phe Met Ile Tyr Trp Tyr Asn Asn Ser
    450                 455                 460
Asp Trp Tyr Asn Asn Ser Asp Trp Tyr Asn Asn
465                 470                 475

<210> SEQ ID NO 7
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Block 5 Conserved Group for protein
      Cry1A"

<400> SEQUENCE: 7

Val Tyr Ile Asp Arg Ile Glu Phe Val Pro
1               5                   10

<210> SEQ ID NO 8
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Block 5 Conserved Group for protein
      Cry3A"

<400> SEQUENCE: 8

Val Tyr Ile Asp Lys Ile Glu Phe Ile Pro
1               5                   10

<210> SEQ ID NO 9
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Block 5 Conserved Group for protein
      Cry4A"

<400> SEQUENCE: 9

Val Leu Ile Asp Lys Ile Glu Phe Leu Pro
1               5                   10

<210> SEQ ID NO 10
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Block 5 Conserved Group for protein
      Cry5A"

<400> SEQUENCE: 10
```
Val Phe Leu Asp Arg Ile Glu Phe Ile Pro
1 5 10

<210> SEQ ID NO 11
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="Block 5 Conserved Group for protein Cry5B"

<400> SEQUENCE: 11

Leu Phe Leu Asp Arg Ile Glu Phe Val Pro
1 5 10

<210> SEQ ID NO 12
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="Block 5 Conserved Group for protein Cry7A"

<400> SEQUENCE: 12

Phe Tyr Val Asp Ser Ile Glu Phe Ile Pro
1 5 10

<210> SEQ ID NO 13
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="Block 5 Conserved Group for protein Cry8A"

<400> SEQUENCE: 13

Val Tyr Ile Asp Arg Ile Glu Phe Ile Pro
1 5 10

<210> SEQ ID NO 14
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="Block 5 Conserved Group for protein Cry9A"

<400> SEQUENCE: 14

Val Tyr Val Asp Arg Ile Glu Phe Ile Pro
1 5 10

```
<210> SEQ ID NO 15
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Block 5 Conserved Group for protein
      Cry10A"

<400> SEQUENCE: 15

Ile Tyr Ile Asp Lys Ile Glu Phe Ile Pro
1               5                   10

<210> SEQ ID NO 16
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Block 5 Conserved Group for protein
      Cry12A"

<400> SEQUENCE: 16

Met Val Leu Asp Arg Ile Glu Phe Val Pro
1               5                   10

<210> SEQ ID NO 17
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Block 5 Conserved Group for protein
      Cry13A"

<400> SEQUENCE: 17

Ile Tyr Leu Asp Arg Leu Glu Phe Val Pro
1               5                   10

<210> SEQ ID NO 18
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Block 5 Conserved Group for protein
      Cry14A"

<400> SEQUENCE: 18

Ile Phe Ile Asp Arg Ile Glu Phe Ile Pro
1               5                   10

<210> SEQ ID NO 19
<211> LENGTH: 10
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Block 5 Conserved Group for protein
      Cry19A"

<400> SEQUENCE: 19

Leu Ile Leu Asp Lys Ile Glu Phe Leu Pro
1               5                   10

<210> SEQ ID NO 20
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Block 5 Conserved Group for protein
      Cry20A"

<400> SEQUENCE: 20

Phe Val Leu Asp Lys Ile Glu Leu Ile Pro
1               5                   10

<210> SEQ ID NO 21
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Block 5 Conserved Group for protein
      Cry21A"

<400> SEQUENCE: 21

Leu Phe Leu Asp Arg Ile Glu Phe Ile Ser
1               5                   10

<210> SEQ ID NO 22
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus sequence"

<400> SEQUENCE: 22

Ile Ile Asp Lys Ile Glu Phe Ile Pro
1               5

<210> SEQ ID NO 23
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide motif"
```

<400> SEQUENCE: 23

Asp Arg Ile Glu Phe
1               5

<210> SEQ ID NO 24
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide motif"

<400> SEQUENCE: 24

Asp Arg Leu Glu Phe
1               5

<210> SEQ ID NO 25
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="original signal peptidase cleavage site"

<400> SEQUENCE: 25

Asp Thr Asn Ser Asp
1               5

<210> SEQ ID NO 26
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic forward primer"

<400> SEQUENCE: 26
cgttcaaaat catccgtaaa tg                                           22

<210> SEQ ID NO 27
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic reverse primer"

<400> SEQUENCE: 27
aaatgcatga accacttcca c                                            21

<210> SEQ ID NO 28
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic forward primer"

<400> SEQUENCE: 28
tggcaacaat taatgagttg tatccag                                      27

-continued

```
<210> SEQ ID NO 29
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic reverse primer"

<400> SEQUENCE: 29
ctgccttgac aaatggctac t                                             21

<210> SEQ ID NO 30
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic forward primer"

<400> SEQUENCE: 30
caccccaggc tttacacttt a                                             21

<210> SEQ ID NO 31
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic reverse primer"

<400> SEQUENCE: 31
aggcgattaa gttgggtaac g                                             21
```

ANTHELMINTIC COMPOSITIONS AND METHODS

RELATED APPLICATIONS

This application is a 35 U.S.C. § 371 filing of International Patent Application No. PCT/US2017/013436, filed Jan. 13, 2017, which claims the benefit of priority to U.S. Provisional Patent Application No. 62/279,597, filed Jan. 15, 2016. The entire content of these applications are incorporated herein by reference for all purposes.

BACKGROUND

Soil-transmitted helminthes (STHs) that parasitize the GI tract of humans infect 2.3 billion of the poorest peoples and >400,000,000 of the poorest children worldwide. (Hall, A., et al. *Matern Child Nutr* 4 Suppl 1, 118-236 (2008)) Infected children can exhibit growth stunting, retarded cognitive development, lethargy, malnutrition, increased school absenteeism, and vulnerability to secondary infections. (Bethony, J. et al. *Lancet* 367, 1521-32 (2006); Hotez, P. J. Forgotten people, Forgotten diseases. (2008)) Pregnant women who are infected are at increased risk for low birth-weight babies and for maternal and infant mortality. (Brooker et al., *PLoS Negl Trop Dis* 2, e291 (2008)). Infected individuals have lower energy, lower productivity, and immune defects that result in increased virulence of HIV/AIDS and a higher likelihood of contracting malaria and tuberculosis (Stothard et al., *Ann Trop Med Parasitol* 103, 357-60 (2009); Moran, M. et al., G-finder Report (2009)); STHs thus trap large populations of the developing world in poverty. The common link of STH transmission is poor sanitation, which requires a massive investment in infrastructure and public health.

Conventional chemotherapy approved by the World Health Organization for STH infections in humans involves treatment with benzimidazoles (e.g., albendazole, mebendazole) or nicontinic acetylcholine receptor (nAChR) agonists (pyrantel, levamisole). (Keiser and Utzinger, *JAMA* 299, 1937-48 (2008)). These compounds, however, lack full efficacy against most human STH parasites. Reports in humans of resistance to both classes of drugs are increasing (e.g., Tanzania, 2010 (Stothard et al., *Ann Trop Med Parasitol* 103, 357-60 (2009)), potentially rendering ineffective current strategies for controlling STH infections. A notable challenge in this field is that the infected populations are among the poorest in the world, and economic incentives to develop new drugs are low (~$700,000/year is spent to develop new drugs against human STHs (Moran, M. et al. G-finder Report (2009)). The poverty of infected populations demands that STH therapeutics be safe, effective, and also inexpensive; highly stable even in the absence of a cold chain; transportable through distribution routes to infected populations; and amenable to culturally acceptable delivery systems.

Crystal (Cry) proteins made by the soil bacterium *Bacillus thuringiensis* (Bt) may be candidate agents that provide safe and effective treatment of STHs. Cry proteins have been in use for 60+ years as safe, natural, organic insecticides for control of crop pests, mosquitoes, and black flies. (Roh, J. Y., et al. J MICROBIOL BIOTECHNOL 17, 547-59 (2007)). They are also effective against nematodes. (Wei, J. Z. et al. PROC NATL ACAD SCI 100, 2760-5 (2003)). Cry proteins are non-toxic to vertebrates and are EPA approved for expression in transgenic food (e.g., corn, potato). (Mohamadzadeh et al. PNAS 106, 4331-6 (2009); Betz F. S., et al. REGUL TOXICOL PHARMACOL 32, 156-73 (2000)). They are stable and cheap to mass-produce. Activity of Cry proteins against nematode plant parasites and against helminthes has been described, e.g., in WO2007/062064; US2010/0024075; WO2010/053517; and US2011/0263489; see also, e.g., Li, X.-Q. et al., 2008 *Biol. Control* 47:97-102, which describes activity of a Cry5B protein truncated at amino acid residue 698 against *C. elegans* and plant parasitic nematodes.

Two Cry proteins, Cry5B and Cry21A, are highly potent anthelmintics in vivo. (See Cappello, M. et al. PROC NATL ACAD SCI USA 103, 15154-9 (2006); Hu, Y., et al. PLoS NEGL TROP DIS 4, e614 (2010); and Hu, Y., et al. PROC NATL ACAD SCI USA 107, 5955-60 (2010)). Cry5B is effective against three intestinal nematodes, *Ancylostoma ceylanicum* hookworms in hamsters, *Heligmosomoides bakeri* in mice, and *Ascaris suum* parasites in pigs, and is 3×-60,0000× more potent than known chemical anthelmintics in a single dose. (See Cappello, M. et al. PROC NATL ACAD SCI 103, 15154-9 (2006); Hu, Y., et al. *PLoS NEGL TROP DIS* 4, e614 (2010); Hu, Y., et al. *PLoS NEGL TROP DIS* 6(11), e1900 (2012); and Urban, J., et al *PLoS NEGL TROP DIS* 7(6), e2263 (2013)). Importantly, screens for Cry-resistance mutations in the nematode *Caenorhabditis elegans* indicate that nematodes are 3-20× less likely to develop resistance to Cry proteins than to benzimidazoles or nAChR agoinsts. (Hu, Y., et al. PROC NATL ACAD SCI 107, 5955-60 (2010)). Furthermore, Cry5B is able to overcome benzimidazoles and nAChR agonist resistance in nematodes (Hu, Y., et al. PROC NATL ACAD SCI 107, 5955-60 (2010)).

Despite the established anthelmintic biological activity of Cry proteins, significant challenges remain with respect to effective delivery of intact, biologically active Cry proteins into the gastrointestinal (GI) tract for treating STHs. These proteins typically have molecular weights of ~135 kDa in their protoxin (unprocessed) forms and ~70 kDa in their active (processed) forms, creating technical difficulties for delivery to the GI lumen via known routes of administration, including problems arising from degradation, poor absorption, clearance mechanisms and other impediments. Moreover, the cost and scalability of Cry protein expression and purification limits its application as a practical STH therapy in the developing world where treatments must be available at a very low costs (less than $1/dose) and in very large quantities to treat a large and poor patient population.

A cheap, simple, and scalable way to deliver Cry proteins is to express it in *B. thuringiensis*, which is ideally suited to express very high levels of Cry protein and which is already fermented cheaply on a massive scale for environmental release. However, *B. thuringiensisis* is very closely related to the human pathogen *Bacillus cereus* and contains many of the enterotoxin genes that causes food poisoning in humans Feeding people large quantities of fully active *B. thuringiensis* therefore has pathogenic potential. Accordingly, there remains an urgent need in the art for for new approaches to delivering protein therapeutics such as anthelmintic proteins to the GI tract.

SUMMARY

The instant disclosure improves upon the art by providing antihelminthic compositions that are both safe and effective for oral delivery. In particular, the instant disclosure is based on the surprising discovery that a non-sporulating bacterium expressing a nematicidal protein (e.g., a heterologous *B. thuringiensis* crystal protein) can be inactivated or killed to reduce or eliminate its toxicity when orally administered to a human subject but without altering the anti-helminthic activity of the nematicidal protein. Notably, the anti-nematicidal efficacy of the killed bacterial product against a particular parasitic worm or helminth is superior to that of purified nematicidal protein.

In exemplary embodiments, the inactive or killed bacterium is genetically engineered such that nematicidal protein is made and trapped in the cytosol of the bacterium. The protein may be retained in the cytosol or released, e.g., if the bacterium is broken open following digestion. The non-sporulating bacterium can be a sporulation-defective variant of a Gram positive bacterium, such as a *Bacillus* sp., including *B. thuringiensis*. For example, the bacterium can be a sporulation mutant, such as a spo0A- mutant. Alternatively, non-sporulating baceterium can be a Gram-negative bacterium (e.g., *E.coli* or *P. fluorescens*).

In certain aspects, the instant disclosure provides an orally-available pharmaceutical composition comprising a killed or inactivated and non-sporulating bacterium that is genetically engineered to express a nematicidal protein. In certain embodiments, the killed or inactivated bacterium is genetically engineered to have a genetic mutation that results in a defect in sporulation such that the nematicidal protein is expressed and trapped in the cytosol of the bacterium. In one embodiment, the nematicidal protein is under control of a promoter that is actively and/or highly expressed prior to the sporulation phase of a bacterium, e.g., during the vegetative growth or stationary phase. In certain embodiments, the promoter is heterologous (i.e., a non-sporulation specific promoter). In one embodiment, the promoter is a Cry3A, GerA, GNAT, or TadA promoter. In one embodiment, the nematicidal protein is a cytoplasmic Cry crystal protein. In one embodiment, the cytoplasmic Cry protein is selected from the group consisting of Cry5B, Cry5C, Cry5D, Cry6A, Cry13A, Cry14A, Cry21A, Cry21B, and Cry55A. In one embodiment, the inactivated bacterium is *Bacillus* sp. In one embodiment, the inactivated bacterium is *Bacillus thuringiensis* (Bt).

In one embodiment, the genetic mutation resulting in a defect of sporulation is the deletion or inactivation of one or more genes selected from the group consisting of: kinA, kinB, spo0A, spo0B, spo0E, spo0F, spo0J, spo0M spoIIB, spoIID, spoIIE, spoIIF, spoIIG, spoIIL, spoIIM, spoIIIA, spoIIIB, spoIIIE, spoIVA, spoIVC, spoIVD, spoVG, spoVK, spoVL, spoVM, spoVN, spoVP, spoVQ, spoVID, σH, σF, σE, σG, and σK. In one embodiment, the genetic mutation resulting in a defect of sporulation is the deletion or inactivation of the spo0A gene. In one embodiment, the composition is encapsulated by a pharmaceutical grade capsule in a dry powdered form.

In another aspect, a method for producing a pharmaceutical composition, the method comprising: exposing a bacterium to an antimicrobial agent, wherein the bacterium is genetically engineered to express a nematicidal protein. In certain embodiments the inactivated bacterium is genetically engineered to have a genetic mutation that results in a defect in sporulation. In another embodiment, the method further comprises lyophilizing the bacterium. In another embodiment, the method further comprises encapsulating the bacterium in a pharmaceutical-grade capsule. In one embodiment, wherein the antimicrobial agent is selected from the group consisting of: an antimicrobial compound; and gamma irradiation. In one embodiment, the antimicrobial compound is a food-grade antibiotic. In another embodiment, the antimicrobial compound is a beta-lactam antibiotic. In another embodiment, the antimicrobial compound is a terpene. In another embodiment, the terpene is selected from the group consisting of thymol, eugenol, geraniol, carvacrol, and citral, or a combination thereof. In another embodiment, the terpene is carvacrol. In another embodiment, the nematicidal protein is under control of a promoter that is actively and/or highly expressed prior to the sporulation phase of a bacterium, e.g., during the stationary phase. In certain embodiments, the promoter is heterologous. In one embodiment, the promoter is a Cry3A, GerA, GNAT, or TadA promoter.

In one embodiment, the nematicidal protein is a cytoplasmic crystal protein. In another embodiment, the cytoplasmic crystal protein is selected from the group consisting of Cry5B, Cry5C, Cry5D, Cry6A, Cry13A, Cry14A, Cry21A, Cry21B, and Cry55A. In another embodiment, wherein the inactivated bacterium is *Bacillus* sp. In another embodiment, the inactivated bacterium is *Bacillus thuringiensis* (Bt). In another embodiment, the genetic mutation resulting in a defect of sporulation is the deletion or inactivation of one or more genes selected from the group consisting of: kinA, kinB, spo0A, spo0B, spo0E, spo0F, spo0J, spo0M spoIIB, spoIID, spoIIE, spoIIF, spoIIG, spoIIL, spoIIM, spoIIIA, spoIIIB, spoIIIE, spoIVA, spoIVC, spoIVD, spoVG, spoVK, spoVL, spoVM, spoVN, spoVP, spoVQ, spoVID, σH, σF, σE, σG, and σK. In another embodiment, the genetic mutation resulting in a defect of sporulation is the deletion or inactivation of the spo0A gene.

In another aspect, the disclosure provides a method of treating a parasitic worm infection in a subject comprising: administering to the subject a therapeutically effective amount of a composition comprising a killed or inactivated bacterium that is genetically engineered to express a nematicidal protein. In certain embodiments, the inactivated bacterium is genetically engineered to have a genetic mutation that results in a defect in sporulation. In one embodiment, the nematicidal protein is under control of a promoter that is actively and/or highly expressed prior to the sporulation phase of a bacterium, e.g., during the stationary phase. In certain embodiments, the promoter is heterologous. In one embodiment, the promoter is a Cry3A, GerA, GNAT, or TadA promoter.

In another embodiment, the nematicidal protein is a cytoplasmic crystal protein. In another embodiment, wherein the cytoplasmic crystal protein is selected from the group consisting of Cry5B, Cry5C, Cry5D, Cry6A, Cry13A, Cry14A, Cry21A, Cry21B, and Cry55A. In another embodiment, the inactivated bacterium is *Bacillus* sp. In another embodiment, the inactivated bacterium is *Bacillus thuringiensis* (Bt). In another embodiment, the genetic mutation resulting in a defect of sporulation is the deletion or inactivation of one or more genes selected from the group consisting of: kinA, kinB, spo0A, spo0B, spo0E, spo0F, spo0J, spo0M spoIIB, spoIID, spoIIE, spoIIF, spoIIG, spoIIL, spoIIM, spoIIIA, spoIIIB, spoIIIE, spoIVA, spoIVC, spoIVD, spoVG, spoVK, spoVL, spoVM, spoVN, spoVP, spoVQ, spoVID, σH, σF, σE, σG, and σK. In another embodiment, the genetic mutation resulting in a defect of sporulation is the deletion or inactivation of the spo0A gene. In another embodiment, the composition is encapsulated by a pharmaceutical grade capsule.

The parasitic worm or helminth infection can be an infection caused by a parasitic worm or helminth selected from the group consisting of roundworm, whipworm, hookworm, *Ascaris*, pinworm, *Strongyloides, Schistosome*, and trematodes. The parasitic worm or helminth can be selected from the group consisting of hookworm *Ancylostoma duodenale*, hookworm *Ancylostoma ceylanicum*, hookworm *Necator americanus*, whipworm, *Trichuris trichiura*, roundworm *Ascaris lumbricoides*, threadworm *Strongyloides stercoralis*, and pinworm *Enterobius vermiculari*.

In the method, the subject can be a mammal, such as a feline, rodent, canine, bovine, equine, swine, caprine, ovine, and primate; for example, the mammal can be a human.

The crystal protein can be selected from the group consisting of Cry5B, Cry5C, Cry5D, Cry6A, Cry13A, Cry14A, Cry21A, Cry21B, and Cry55A. The crystal protein can be truncated; it can also be a variant. When truncated, the crystal protein can be truncated after a conserved amino acid sequence of block 5. The truncated crystal protein can be missing the last 10 amino acids of the C-terminus; in some cases the truncated crystal protein is truncated between the end of conserved block 5 and the C-terminus of the full length protein. When referring to block 5, the conserved amino acid sequence can be DRIEF (SEQ ID NO:23) or DRLEF (SEQ ID NO:24). The truncated crystal protein can have toxic activity that is at least 10% or more of the toxic activity of a corresponding full-length protein. The truncated crystal protein can be truncated at the N-terminus, such as when the truncated crystal protein does not contain the first 5 amino acids of the N-terminus. Such a truncated crystal protein can be truncated at the C-terminus. The crystal protein can be selected from the group consisting of:

a. Cry5B and wherein the Cry5B includes at least amino acids 30 through about 693 of SEQ ID NO:1 b. Cry6A and wherein the Cry6A comprises the amino acid sequence set forth in SEQ ID NO:2 or includes at least amino acids 30 through about 395, 415 or 435 of SEQ ID NO:6, c. Cry13A and wherein the Cry13A includes at least amino acids 30 through about 688 of SEQ ID NO:2, d. Cry14A and wherein the Cry14A includes at least amino acids 30 through about 675 of SEQ ID NO:3, e. Cry21A and wherein the Cry21A includes at least amino acids 30 through about 685 of SEQ ID NO:4, and f. Cry21A and wherein the Cry21A includes at least amino acids 30 through about 685 of SEQ ID NO:5.

In the disclosed method, the bacterium can be treated with the anti-microbial agent prior to administration of the bacterium to the subject. In some embodiments, the bacterium and the anti-microbial agent are co-administered to the subject. The anti-nematicidal activity of the nematicidal protein is preferably unaffected by the anti-microbial agent. As used herein, an "anti-microbial agent" may be a chemical or physical agent. An example of a chemical anti-microbial agent is a bacteriocidal agent, such as a beta-lactam antibiotic. An example of a physical anti-microbial agent is irradiation (e.g., gamma or U.V. irradiation) or heat treatment. In some embodiments, the anti-microbial agent is iodine or a terpene or formaldehyde. In the case of iodine, it can be Lugol's iodine. In the case of terpene, it can be one selected from the group consisting of thymol, eugenol, geraniol, carvacrol, and citral, or a combination thereof. In some embodiments, the terpene is carvacrol. In certain embodiments, the anti-microbrial agent is a food-grade antibiotic. In the disclosed method, the recombinant bacterium is killed by the anti-microbial treatment.

The disclosed method can further comprise administering an additional therapeutic agent, such as an agent selected from the group consisting of a bacterium expressing, or capable of expressing, a crystal protein, a small molecule, and a polypeptide. An example of such a therapeutic agent is a nicotinic acetylcholine receptor agonist, such as a member of the levamisole family of nicotinic acetylcholine receptor agonists; an example would be levamisole. In other embodiments, the nicotinic acetylcholine receptor agonist is pyrantel or tribendimidine.

In another aspect, disclosed herein is a method of treating hookworm infection in a subject, comprising administering to the subject a therapeutically effective amount of a composition comprising an anti-microbial agent treated recombinant *B. thuringiensis* spo0A- bacterium that is engineered to express a Cry5B crystal protein.

In another aspect, disclosed herein is a method of reducing the severity of a parasitic worm or helminth infection in a subject comprising administering to the subject a therapeutically effective amount of a composition comprising an anti-microbial agent treated recombinant bacterium that is engineered to express a crystal protein.

In another aspect, disclosed herein is a method of preventing a parasitic worm or helminth infection in a subject comprising administering to the subject a therapeutically effective amount of a composition comprising an anti-microbial agent treated recombinant bacterium that is engineered to express a crystal protein.

BRIEF DESCRIPTION OF THE DRAWINGS

FIG. 1B illustrates the positions of conserved blocks among certain Cry proteins. Schnepf, E., et al. "*Bacillus thuringiensis* and Its Pesticidal Crystal Proteins." Microbiology and Molecular Biology Reviews 62(3): 775-806, 781 (FIG. 3) (September 1998).

FIG. 2 illustrates the amino acid sequence of Cry5Ba1 [SEQ ID NO:1].

FIG. 3 illustrates the amino acid sequence of Cry13Aa1 [SEQ ID NO:2].

FIG. 4 illustrates the amino acid sequence of Cry14Aa1 [SEQ ID NO:3].

FIGS. 5A-C FIG. 5A illustrates the amino acid sequence of Cry21Aa1 [SEQ ID NO:4]. FIG. 5B illustrates the amino acid sequence of Cry21Aa2 (98% identical to Cry21Aa1) [SEQ ID NO:5]. FIG. 5C illustrates the amino acid sequence of Cry6A [SEQ ID NO:6].

FIG. 7A depicts intestinal hookworm burdens in nine hamsters following treatment with PY79-vector or PY79-Cry5B (10 mg/kg Cry5B) (error bars in all panels show standard errors). The average worm burdens were 18.6±2.6 and 1.3±0.3 for PY79-vector and PY79-Cry5B, respectively. FIG. 7B depicts fecal egg counts on day −1, day +1, and day +3 relative to the day of treatment. The actual egg counts for PY79-vector and PY79-Cry5B were 965±193 and 1,044±99, respectively, on day −1, 1,055±230 and 94±60, respectively, on day +1, and 1,055±227 and 100+42, respectively, on day +3. EPG, eggs per gram of feces. FIG. 7C depicts in vivo dose-response experiment with 12 hamsters.

The average worm burdens for PY79-vector and PY79-Cry5B at Cry5B concentrations of 0.4 mg/kg, 1.4 mg/kg, and 4 mg/kg were 27.0±3.2, 15.7±7.0, 8.3±0.9, and 5.7±0.9, respectively.

Figure 8:
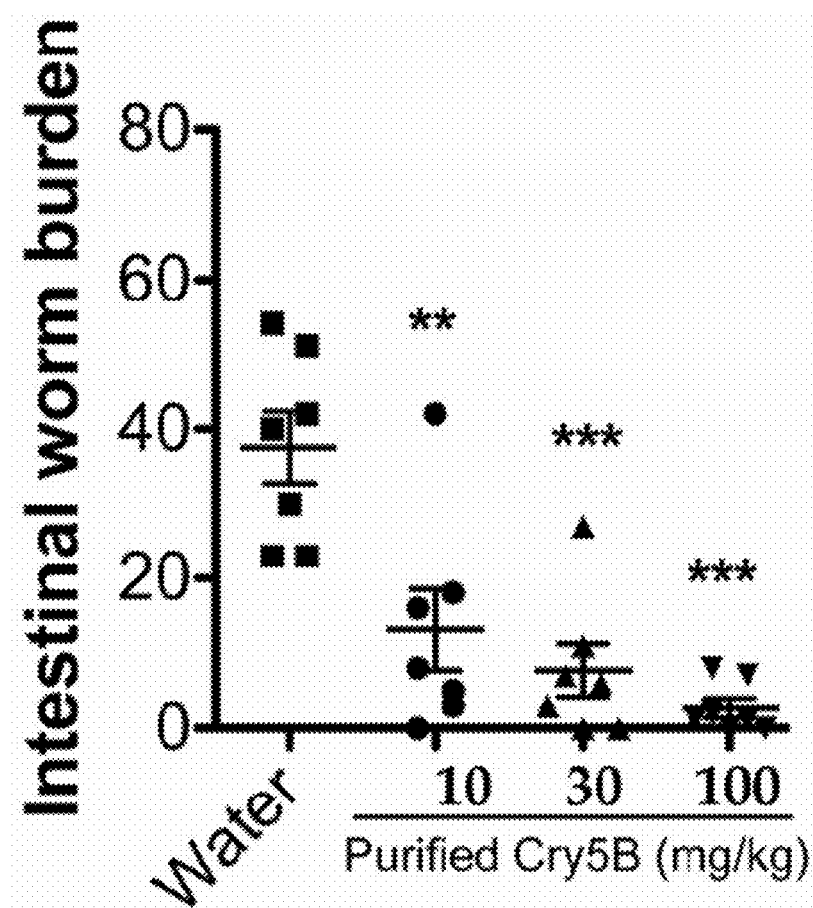
Figure 19A:
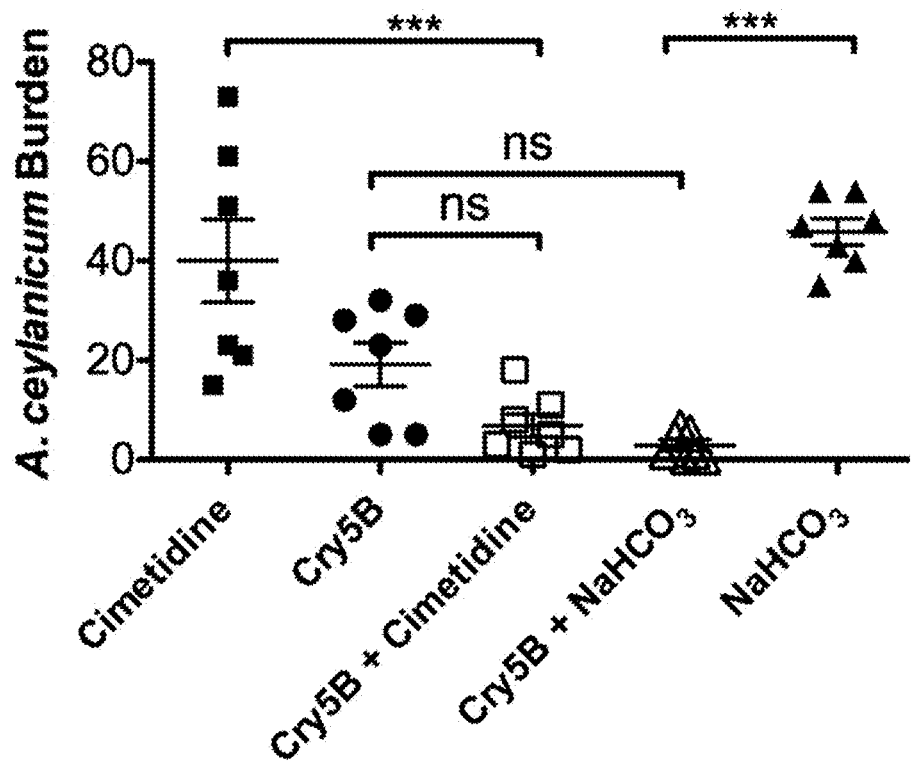
Figure 19B:
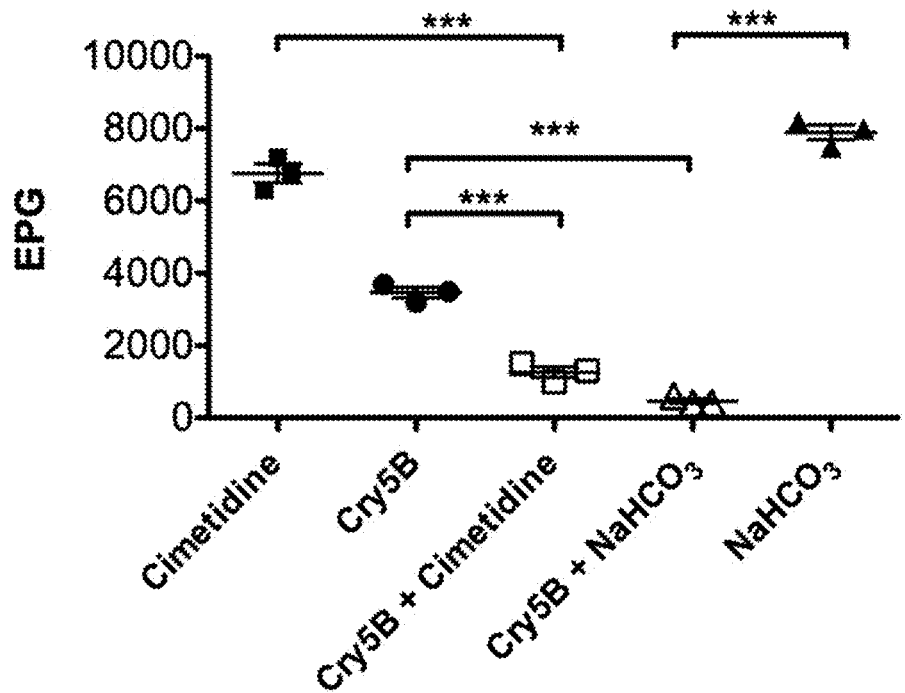
Figure 19C:
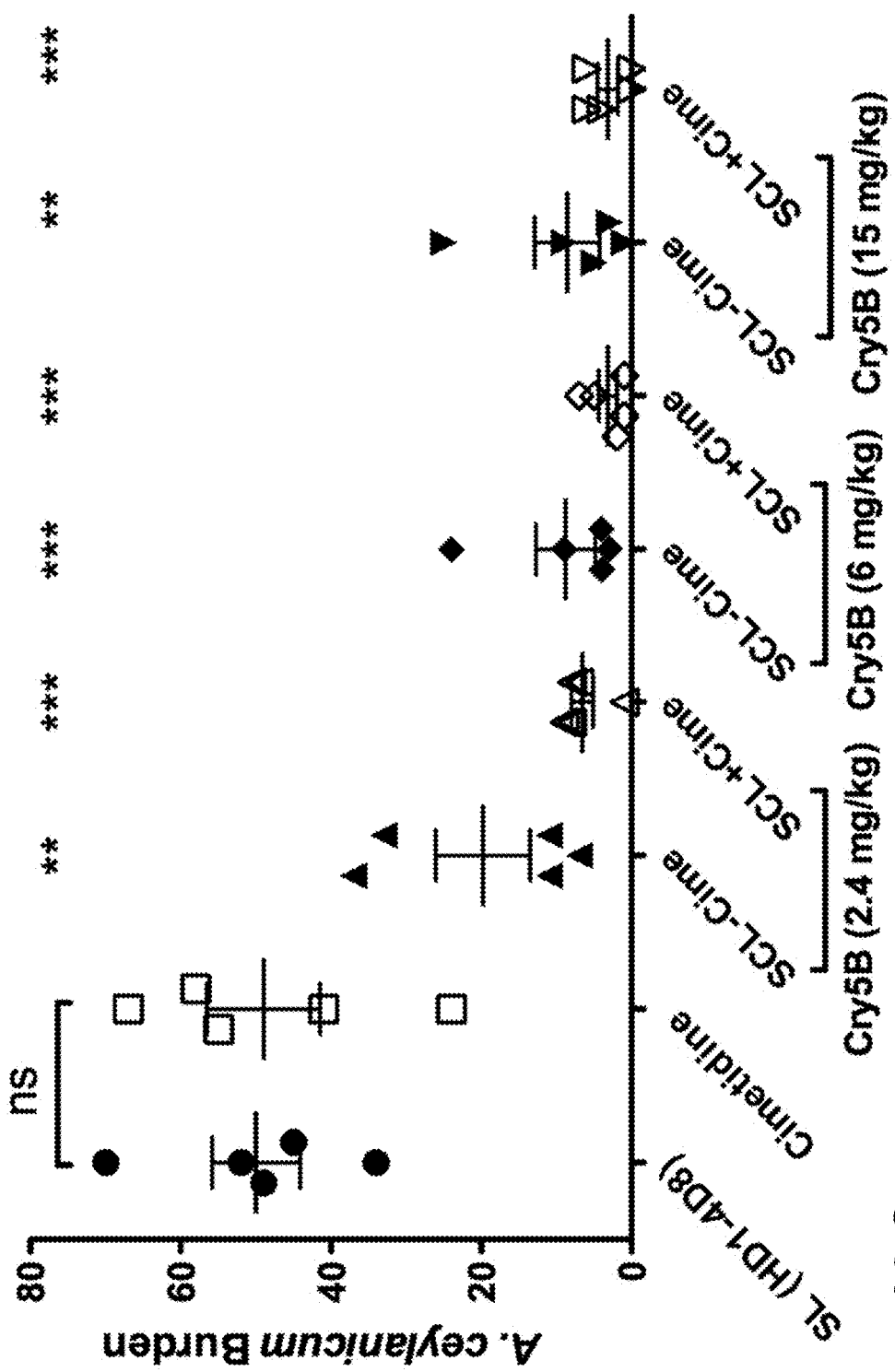
Figure 19D:
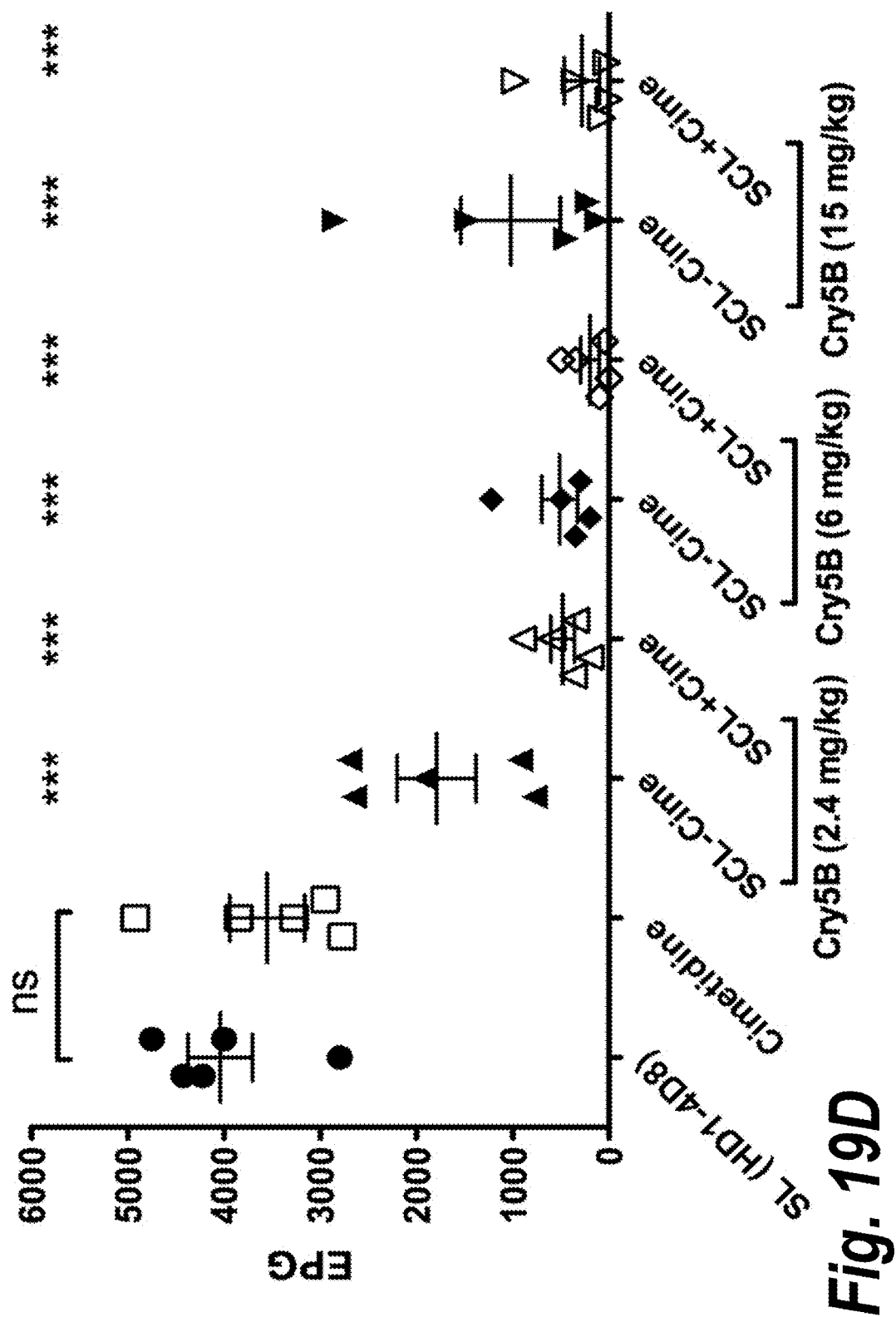
Figure 19E:
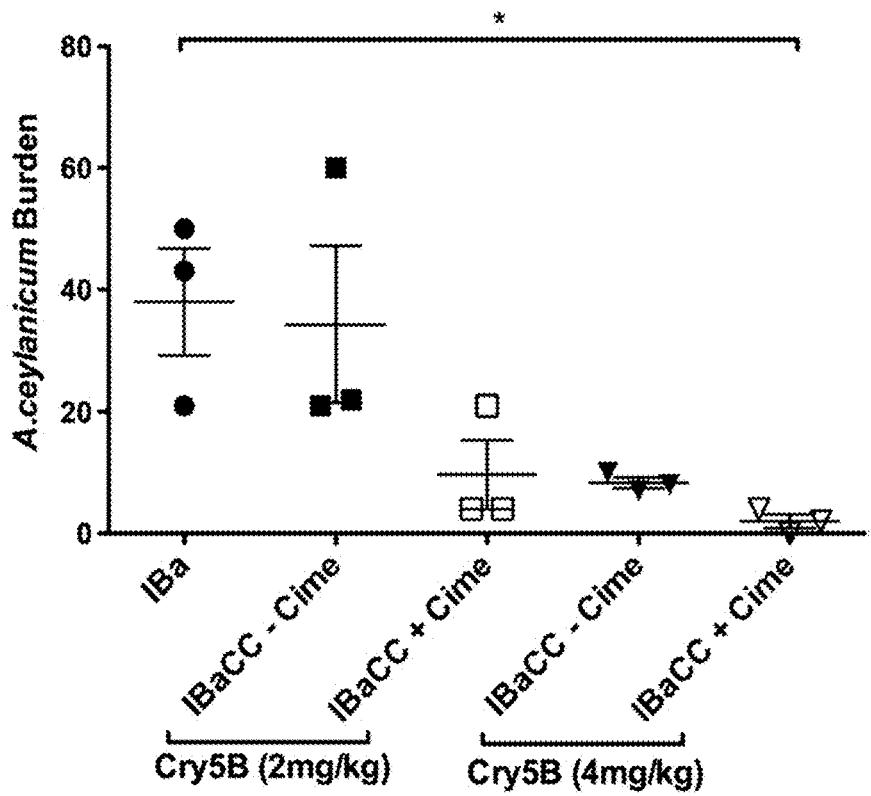
Figure 19F:
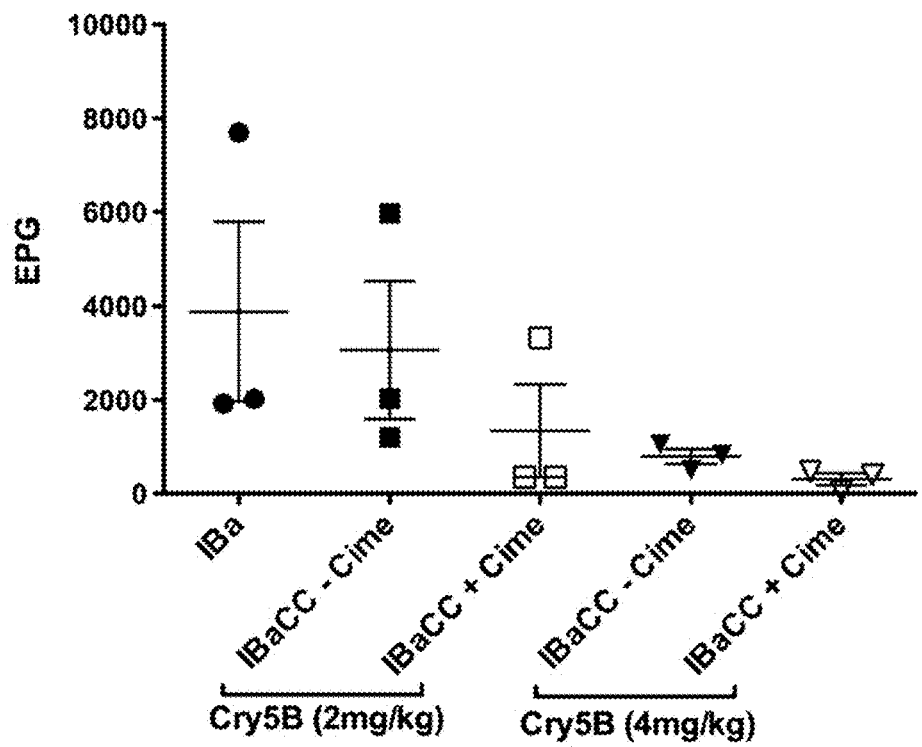

FIG. 8 shows results from an in vivo bioassay of intestinal worm burdens in golden Syrian hamsters infected with *Ancylostoma ceylanicum* hookworms as described by Hu et al. (2012 *PLoS Negl. Trop. Dis.* 6:e1900. doi:10.137/journal.pntd.0001900). The four groups (in black, n=7 per group) shown are the intestinal worm burdens from the groups of infected hamsters treated with purified full-length *B. thuringiensis* Cry5B protein (prepared according to Griffitts et al., 2001 *Science* 293:860; for sequence see FIG. 2) at a single dose of 1 mg (solid circles, 10 mg/kg), 3 mg (solid upright triangles, 30 mg/kg), or 10 mg (solid inverted triangles, 100 mg/kg) (715 nmoles/kg), or with placebo (solid squares, $ddH_2O$), respectively. The treatments were conducted on day 16 P.I. and intestinal worm burdens assessed on day 21 P.I. The worm burdens in each hamster are indicated with a separate symbol. Long horizontal bars represent mean worm burdens; smaller bars indicate SEM (standard error of the mean).

FIG. 9 shows dose-response results for indicated dosages of unfractionated Cry5B-containing spore-crystal lysates (SCL) in the in vivo bioassay of intestinal worm burdens in golden Syrian hamsters infected with *Ancylostoma ceylanicum* hookworms. The assay was performed according to Hu et al. (2012 *PLoS Negl. Trop. Dis.* 6:e1900. doi:10.137/journal.pntd.0001900) except instead of purified Cry5B protein the animals received the indicated dosages, via gavage, of Cry5B spore-crystal lysates obtained from cultured *Bacillus thuringiensis* cells that were transformed with a low copy plasmid that expressed *B. thuringiensis* Cry5B and then grown to sporulation phase, at which point the cells lysed releasing spores, crystals, and bacterial lysate (spore crystal lysate, SCL). The amounts of Cry5B gavaged were determined by taking known volumes of spore crystal lysates, resolving full length Cry5B protein by SDS PAGE, and quantitating the amount of protein in the Cry5B band relative to known amounts of bovine serum albumin (BSA) standards on the gel.

FIG. 10 shows results from the in vivo bioassay of intestinal worm burdens in golden Syrian hamsters infected with *Ancylostoma ceylanicum* hookworms (Hu et al., 2012 *PLoS Negl. Trop. Dis.* 6:e1900. doi:10.137/journal.pntd.0001900) following treatment with two different dosages of Cry5B spore-crystal lysates obtained from cultured *Bacillus thuringiensis natto* cells that were transformed with a low copy plasmid that expressed *B. thuringiensis* Cry5B and then grown to sporulation phase.

FIG. 11 shows data obtained in vitro using the *C. elegans* mortality assay described in FIG. 6 to evaluate the effects on *C. elegans* of purified Cry5B protein (prepared according to Griffitts et al., 2001 *Science* 293:860; for sequence see FIG. 2) when combined in a mixture either with sporulated *B. thuringiensis* HD1 or with sporulated *B. subtilis* PY79. For each data point, the number of spores (HD1 or PY79) was held constant and the quantity of Cry5B was titrated (x-axis).

FIG. 12 shows the effects of Cry14A on an in vivo bioassay of intestinal worm burdens in golden Syrian hamsters infected with *Ancylostoma ceylanicum* hookworms.

FIG. 13 shows a bacterial encapsulation (BENC) system. In this example, a *B. thuringiensis* sporulation mutant spo0A- (and thus trapped in stationary phase) does not contain any crystals (left panel); however, when the sequence of Cry5B is expressed under a stationary phase promoter (such as Cry3A; construct depicted in center panel) in these cells, Cry5B crystals (right panel, arrow) are made and trapped inside the bacterium (right panel).

FIG. 14 shows that *B. thuringiensis* spo0A- cells expressing Cry5B are bioactive against *C. elegans*, whether treated or not with carvacrol for 15 or 60 minutes.

FIGS. 15A-C shows the efficacy of *Bacillus thuringiensis* (Bt) spore-crystal lysate (SCL) against hookworms. FIG. 15A depicts life cycle of Bt and production of SCL. FIG. 15B depicts single dose Cry5B SCL from Bt eliminates *A. ceylanicum* hookworm adults in hamsters in vivo; FIG. 15C depicts single dose Cry5B SCL from Bt eliminates fecal egg counts from hookworm-infected hamsters in vivo.

FIGS. 16A-B shows the effects of irradiation on Bt SCL expressing Cry5B. The spores are largely, although not completely, inactivated but the Cry5B protein is no longer active. FIG. 16A depicts effects of 15 kGy of gamma irradiation on spore counts for two different Cry- Bt strains (4.D.8, 4.D.9) transformed with a Cry5B expressing plasmid or (4.D.8 only) empty vector. FIG. 16B depicts effects of 15 kGy gamma irradiation on Cry5B efficacy expressed in 4.D.8 and 4.D.9 against *C. elegans* at two doses. N F/D=not freeze-dried SCL; F/D=freeze-dried SCL; 15 kGy=freeze-dried SCL subjected to 15 kGy of irradiation.

Figure 17F:
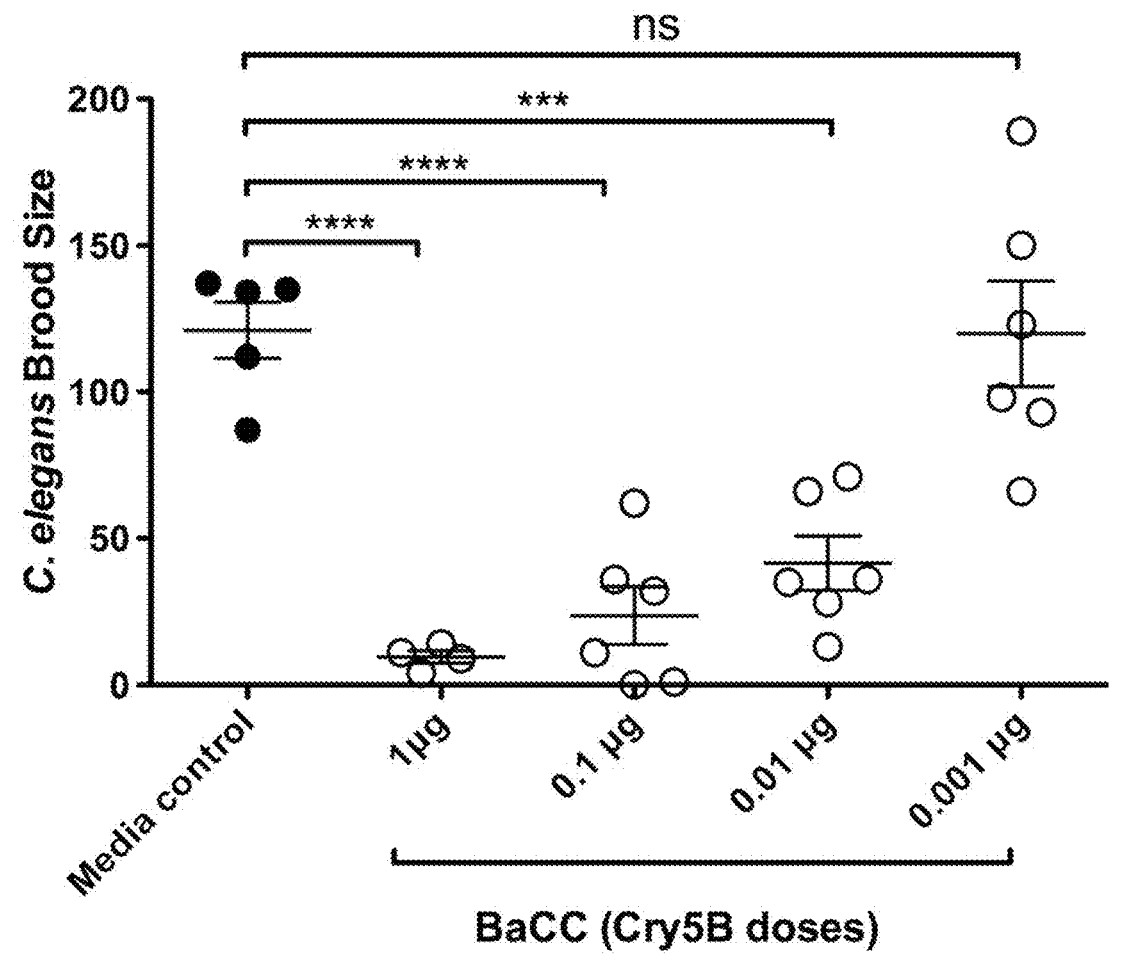

FIGS. 17A-F shows the anti-nematode efficacy of BaCC (live spo0A- Bt cells expressing cytosolic Cry5B crystals). FIG. 17A depicts dose-dependent toxicity curves with BaCC cells either fed intact or broken open prior to feeding (by bead beating). FIG. 25B depicts effects on hookworm burdens of Cry5B expressed in SCL and BaCC cells in vivo against *A. ceylanicum* infections in hamsters. Control includes spo0A- empty-vector cells (Ba), For comparison, the efficacy of SCL is shown. FIG. 17C depicts effects of the same BaCC strains on hookworm fecal egg counts. FIG. 17D depicts the sporulation-defective Bt with a crystal protein trapped in the cytosol. FIG. 17E depicts *C. elegans* intoxicated by BaCC in comparison to empty Spo0A- Bt cells. FIG. 17F depicts a dot plot showing effects of increasing concentrations of Cry5B-BaCC on *C. elegans* brood size.

FIGS. 18A-G shows that IBaCC is a potent anthelmintic in vivo. FIG. 18A depicts the IBaCC strategy. *Bacillus thuringiensis* lacking the spo0A gene cannot sporulate but rather stays in the stationary phase. FIG. 18B depicts a bar graph showing the colony forming units of Spo0A- Bt expressing Cry5B untreated and treated with carvacrol. FIG. 18C depicts a polyacrylamide gel stained with coomassie blue showing the expression of Cry5B in Spo0A- Bt untreated and treated with carvacrol. FIG. 18D depicts a scatter dot plot showing the *A. ceylanicum* burden in IBaCC treated mice. FIG. 18E depicts a scatter dot plot showing the effects of IBaCC treatment on fecal egg counts in mice. FIG. 18 depicts a scatter dot plot showing the *A. ceylanicum* burden in mice treated with a placebo, BaCC-Cry5B or IBaCC-Cry5B. FIG. 18G depicts a plot showing fecal egg counts in mice treated with a placebo, BaCC-Cry5B, or IBaCC-Cry5B. Note, for both SCL (see FIG. 17), BaCC (FIGS. 17, 18), and IBaCC (see FIG. 18), efficacy of the total bacterial product is superior to that of purified protein (FIG. 8, FIG. 19A, B) against the same hookworm infections in hamsters. Thus IBaCC preserves the efficacy and advantages of expressing Cry5B in Bt, which is superior to purified Cry5B protein in efficacy, while IBaCC also preserves the advantage and complete safety of purified protein by killing the bacterium.

FIGS. 19A-F shows that pre-neutralization of stomach acid with enhances the efficacy of Cry5B treatment in vivo.

FIG. 19A depicts a scatter dot plot showing *A. ceylanicum* burden in hamsters treated with Cry5B purified protein at a dose of 8 mg/kg with or without pre-treatment with stomach acid neutralizing agents, cimetidine and $NaHCO_3$. FIG. 19B depicts a scatter dot plot showing fecal egg counts in hamsters treated with Cry5B purified protein at a dose of 8 mg/kg with or without pre-treatment with stomach acid neutralizing agents, cimetidine and $NaHCO_3$. FIG. 19C depicts a scatter dot plot showing *A. ceylanicum* burden in hamsters treated with increasing concentrations of SCL-Cry5B with or without pre-treatment with the stomach acid neutralizing agent cimetidine. FIG. 19D depicts a scatter dot plot showing fecal egg counts in hamsters treated with increasing concentrations of SCL-Cry5B with or without pre-treatment with the stomach acid neutralizing agent cimetidine. FIG. 19E depicts a scatter dot plot showing *A. ceylanicum* burden in hamsters treated with increasing concentrations of IBaCC-Cry5B with or without pre-treatment with the stomach acid neutralizing agent cimetidine. FIG. 19F depicts a scatter dot plot showing fecal egg counts in hamsters treated with increasing concentrations of IBaCC-Cry5B with or without pre-treatment with the stomach acid neutralizing agent cimetidine.

Figure 20:
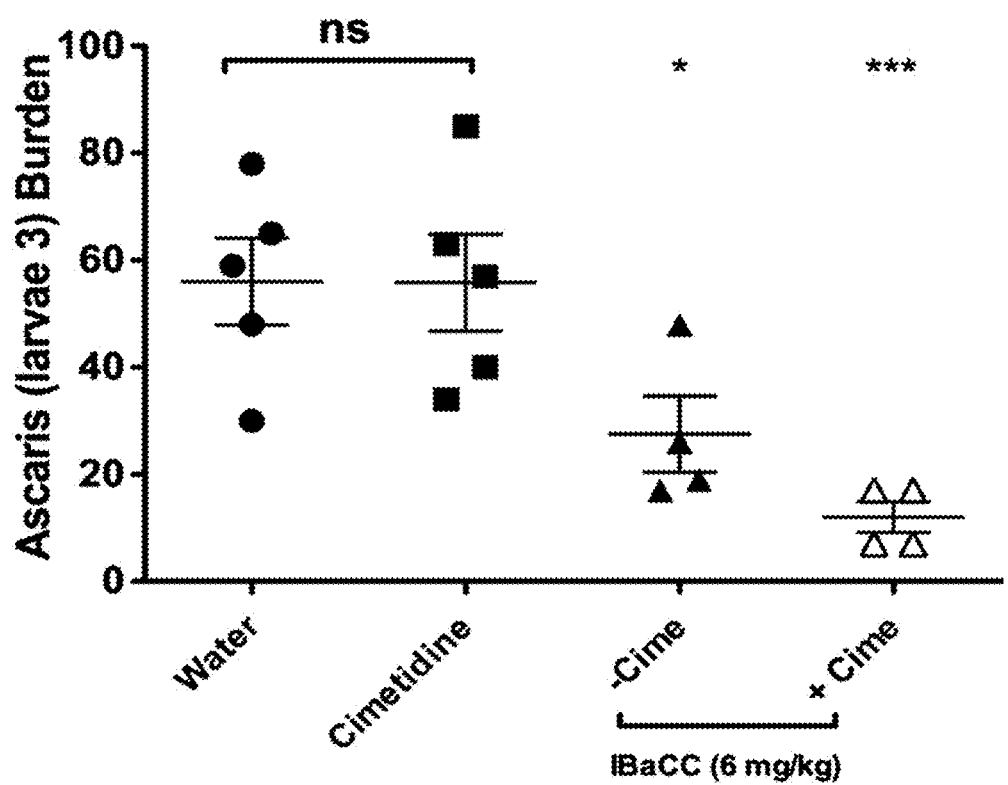

FIG. 20 shows that IBaCC-Cry5B is effective against L3 intestinal *Ascaris suum* in STAT6-/-mice. A scatter dot plot shows *A. suum* burden in mice treated with Cry5B-IBaCC with or without pre-treatment with cimetidine.

Figure 21A:
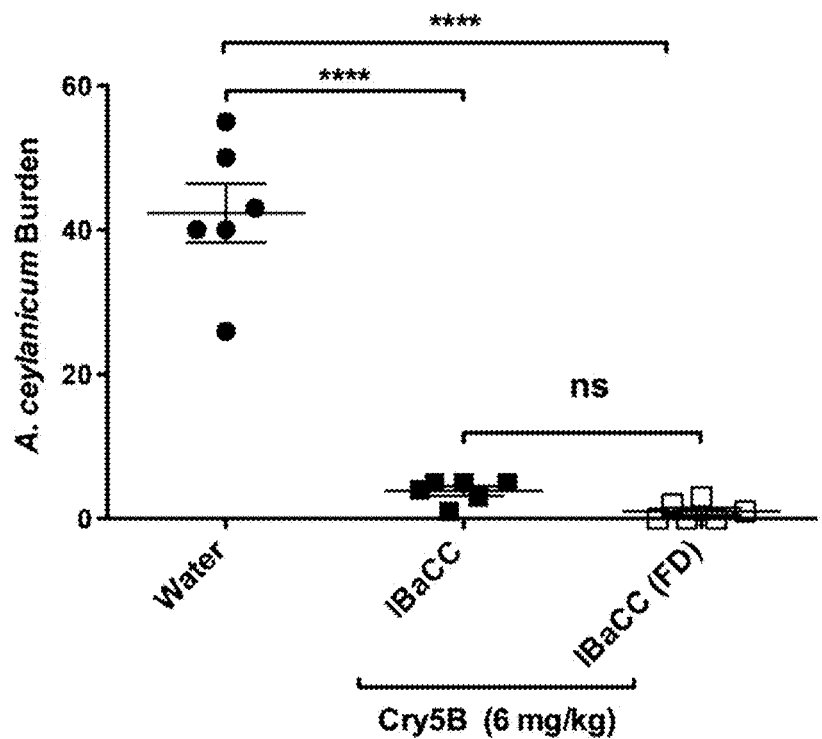
Figure 21B:
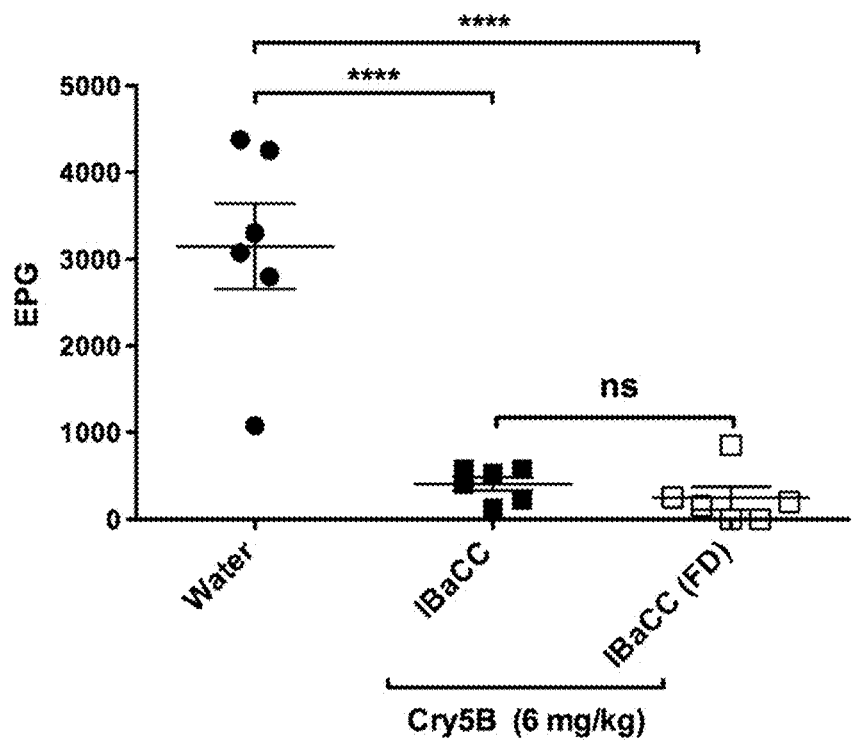

FIGS. 21A-B shows that freeze-dried Cry5B-IBaCC retains full bioactivity against hookworm infections in vivo. FIG. 21A depicts a scatter dot plot showing *A. ceylanicum* burden in hamsters treated with a water control, Cry5B-IBaCC, or Cry5B-IBaCC freeze-dried (FD). FIG. 21B depicts a scatter dot plot showing fecal egg counts in hamsters treated with a water control, Cry5B-IBaCC, or Cry5B-IBaCC freeze-dried (FD).

Figure 22A:
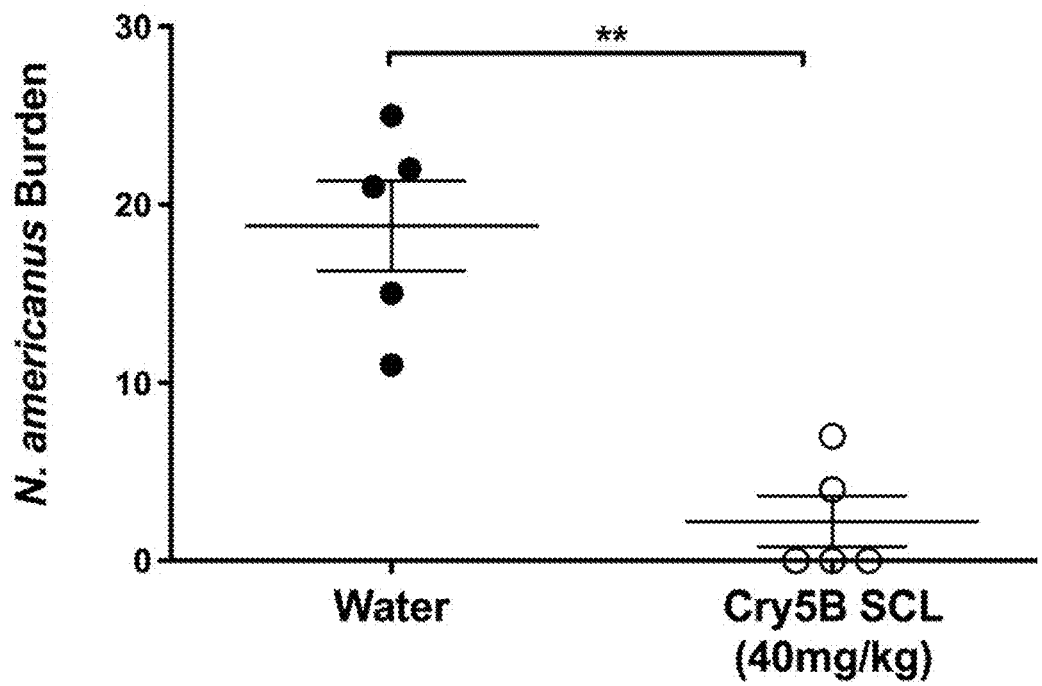
Figure 22B:
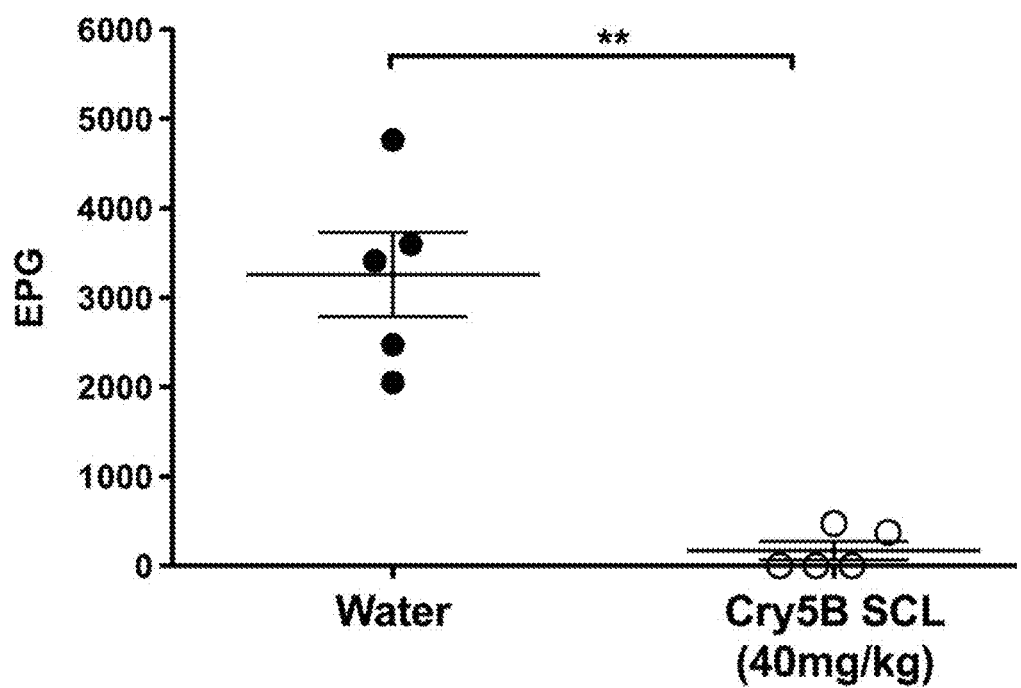
Figure 22C:
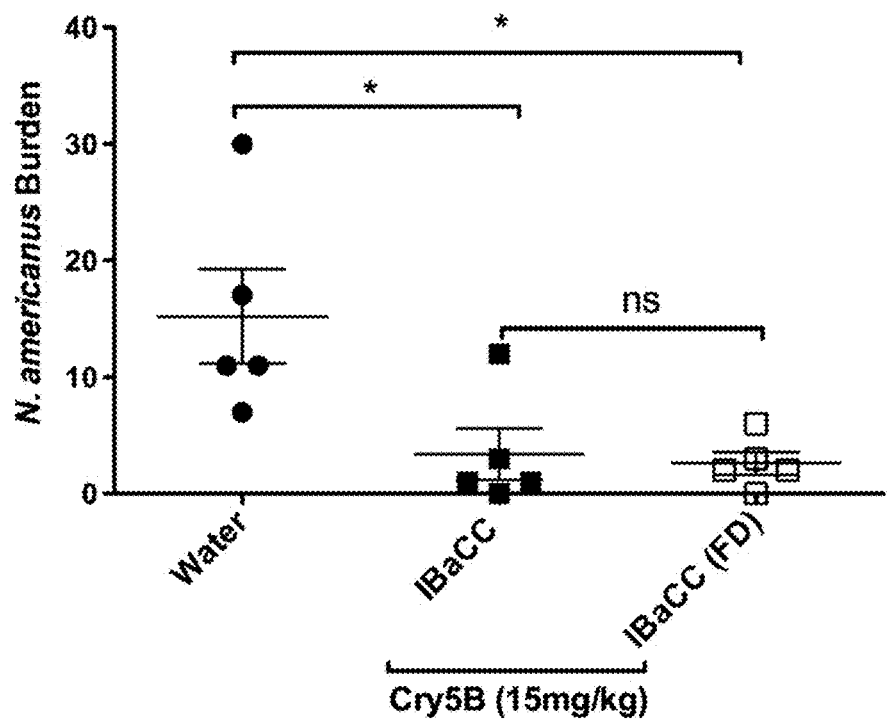
Figure 22D:
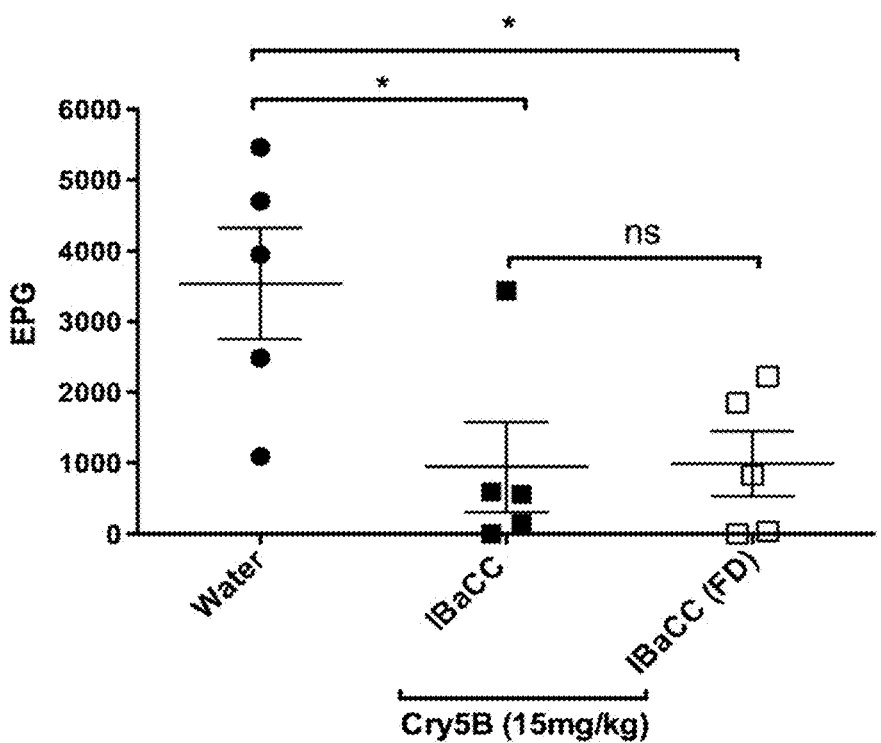

FIGS. 22A-D shows that Cry5B-IBaCC is effective against *Necator americanus*. FIG. 22A depicts a scatter dot plot showing *N. americanus* burden in hamsters treated with Cry5B-SCL or a water control. FIG. 22B depicts a scatter dot plot showing fecal egg counts in hamsters treated with Cry5B-SCL or a water control FIG. 22C depicts a scatter dot plot showing *N. americanus* burden in hamsters treated with Cry5B-IBaCC, freeze-dried (FD) Cry5B-IBaCC, or a water control. FIG. 22D depicts a scatter dot plot showing fecal egg counts in hamsters treated with Cry5B-IBaCC, freeze-dried (FD) Cry5B-IBaCC, or a water control. Since hamsters infected with *Necator* are heavily immunosuppressed with daily dexamethasone treatment, the data also show an intact immune system is not needed for Cry5B activity.

Figure 23A:
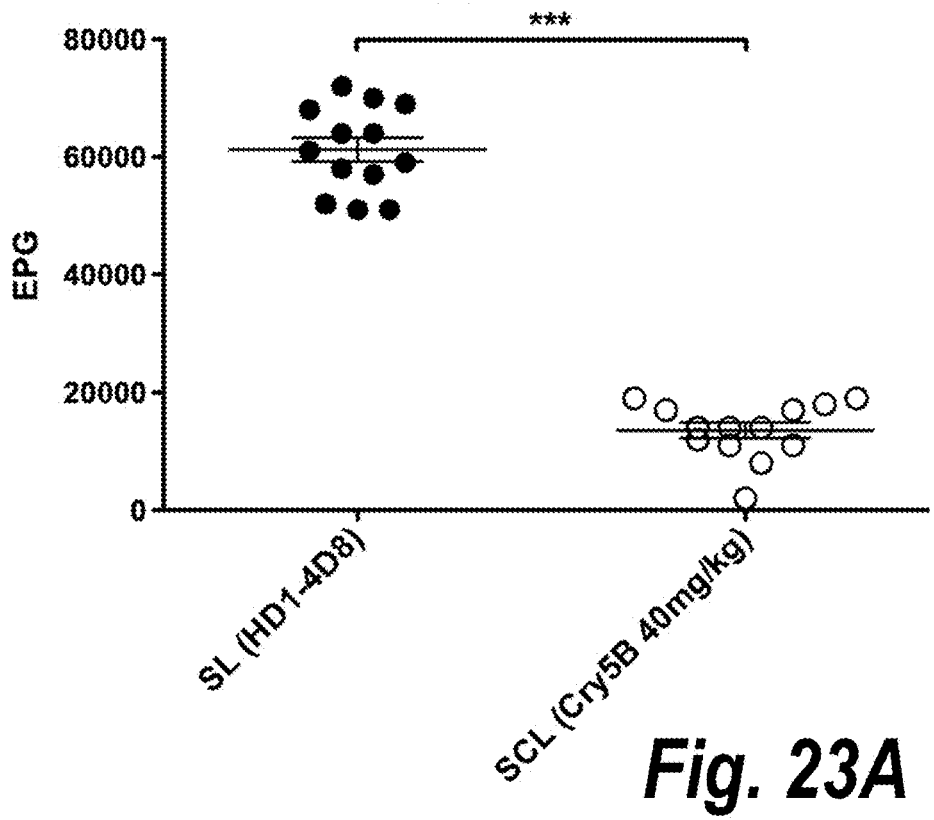
Figure 23B:
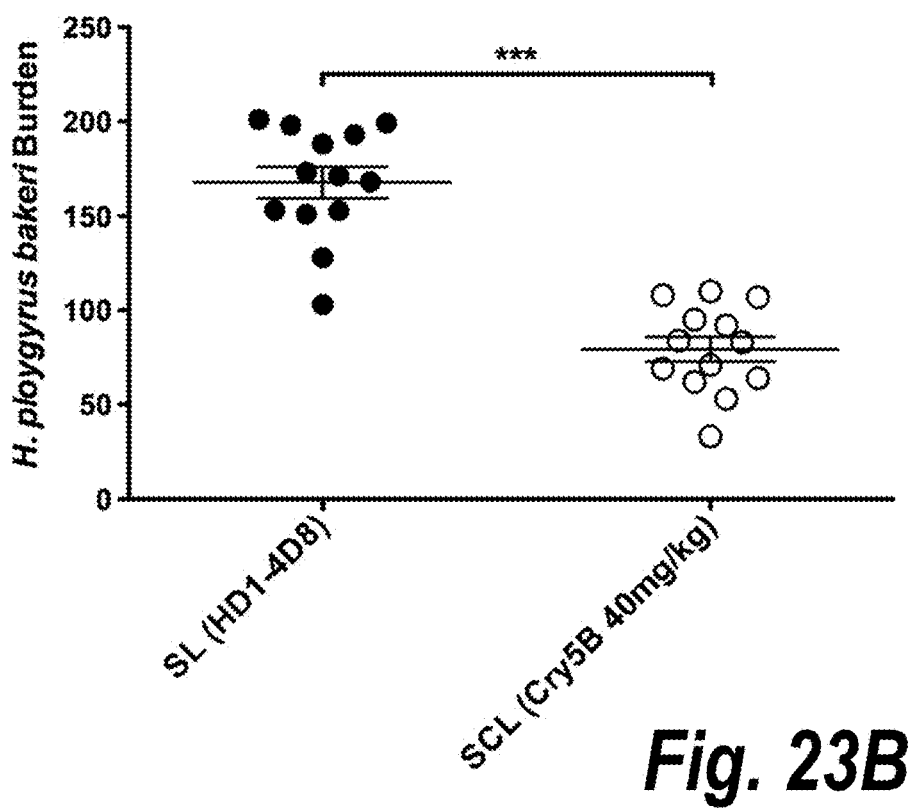

FIGS. 23A-B shows that the immune system is not required for Cry5B efficacy in vivo. FIG. 23A depicts a scatter dot plot showing fecal egg counts in immunosuppressed mice treated with Cry5B-SCL. FIG. 23B depicts a scatter dot plot showing *H. polygyrus* burden in immunosuppressed mice treated with Cry5B-SCL.

Figure 24A:
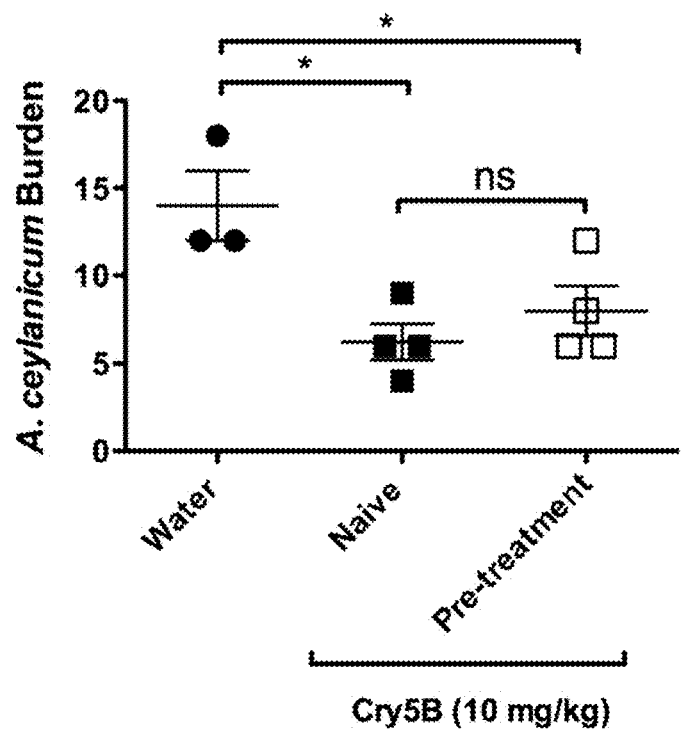
Figure 24B:
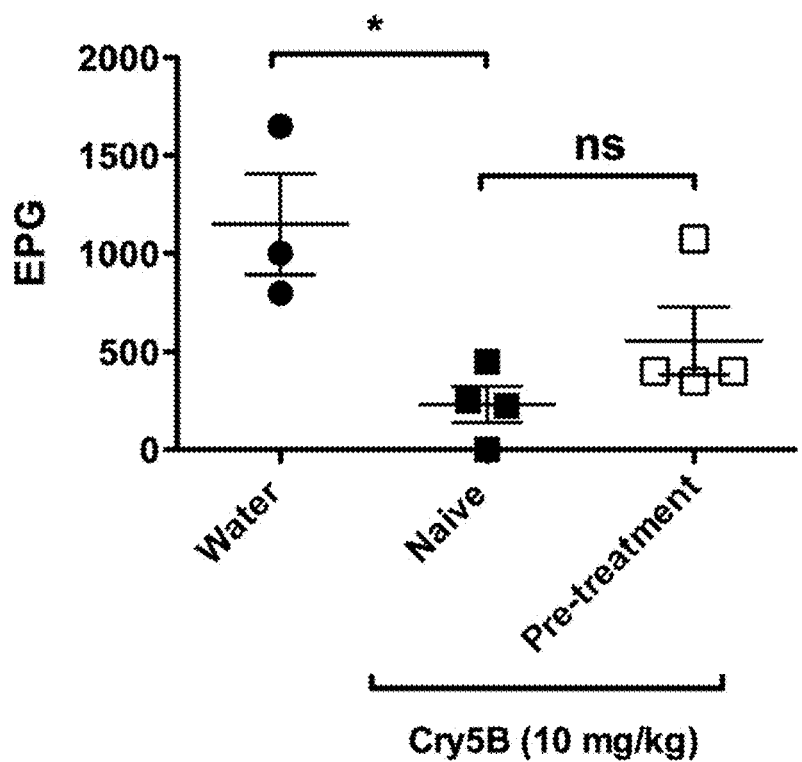
Figure 24C:
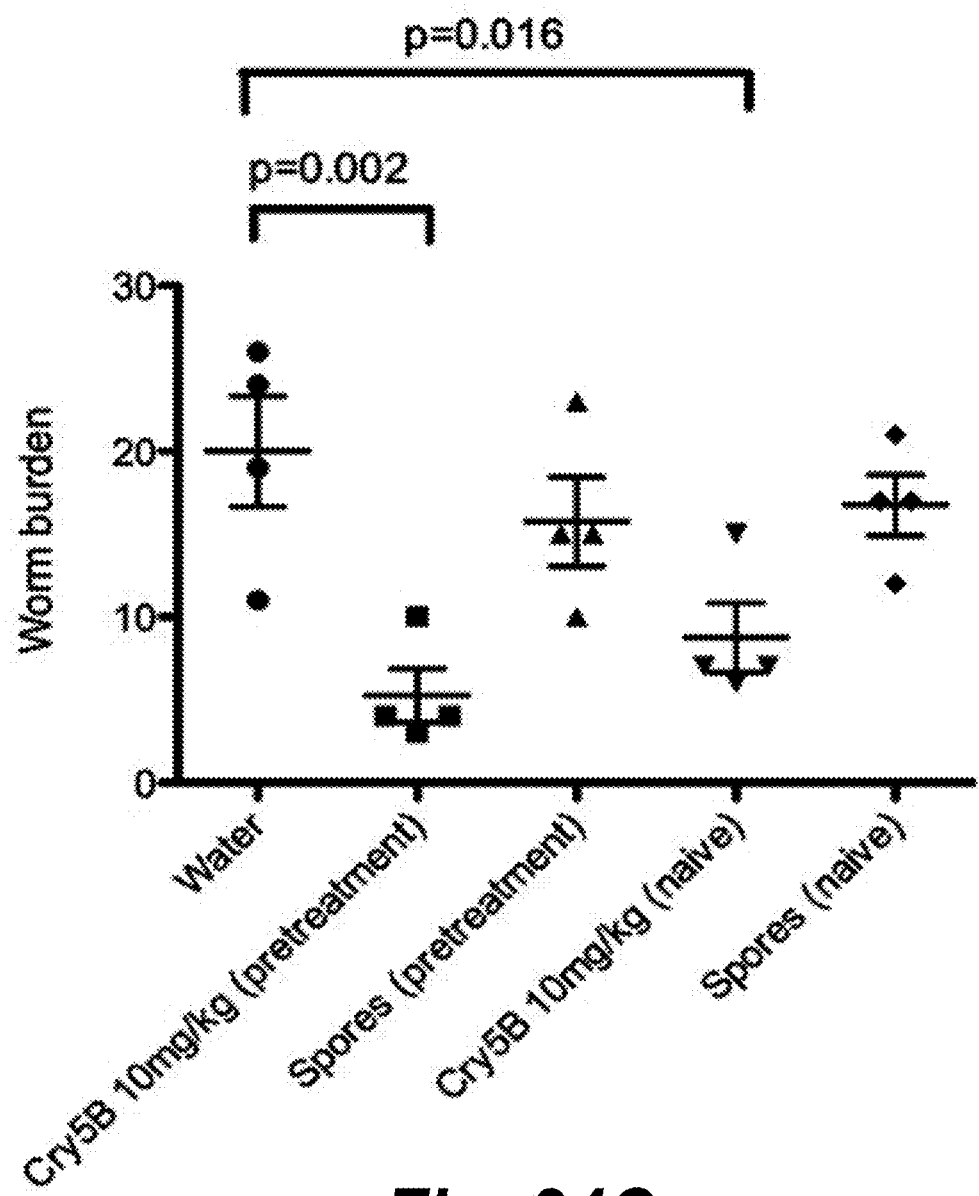

FIGS. 24A-C shows that Cry5B treatment will remain effective with repeated doses. FIG. 24A depicts a scatter dot plot showing *A. ceylanicum* burden in hamsters treated with a water control or purified Cry5B with or without pre-treatment with Cry5B. FIG. 24B depicts a scatter dot plot showing fecal egg counts in hamsters treated with a water control or purified Cry5B with or without pre-treatment with Cry5B FIG. 32C depicts a scatter dot plot showing *A. ceylanicum* burden in hamsters treated with a water control, purified Cry5B or Cry5B-SCL with or without pre-treatment with Cry5B-SCL, and with or without pretreatment with spores.

Figure 25A:
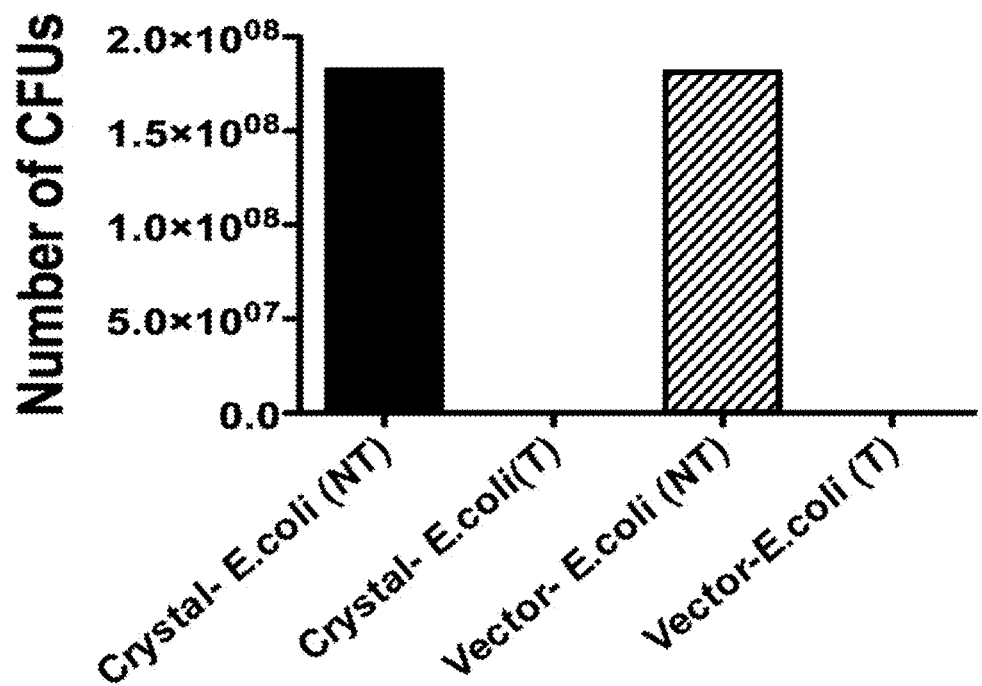
Figure 25B:
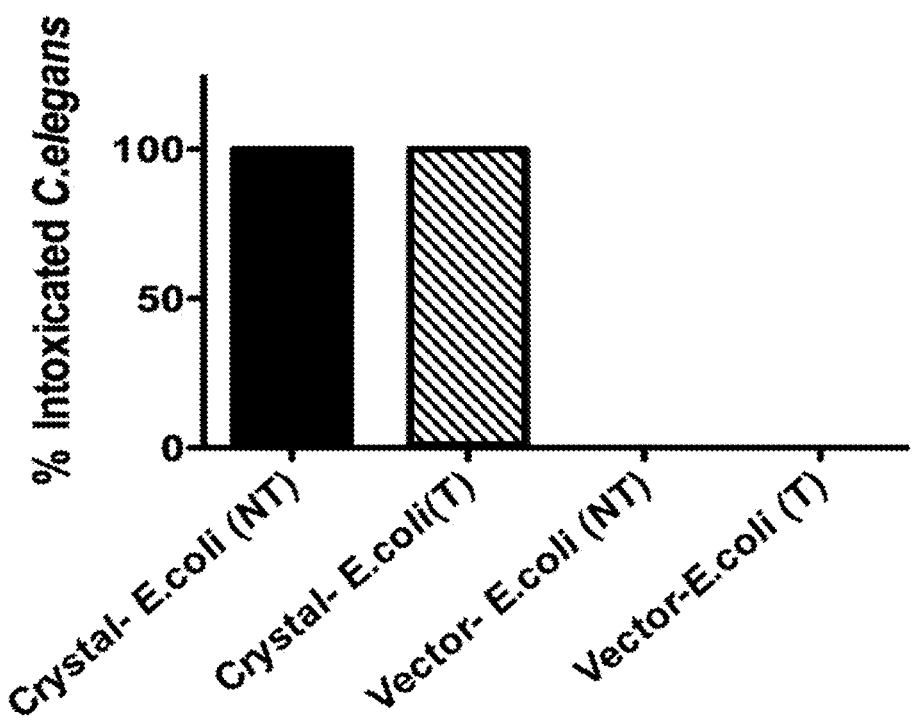

FIGS. 25A-B shows bioactivity of carvacrol-treated Crystal-*E. coli* on *C. elegans*. FIG. 25A depicts a bar graph measuring colony-forming units (CFUs) of carvacrol (1 mg/mL) treated *E. coli* cells harboring nematicidal Crystal protein gene or empty vector control. FIG. 25B depicts a bar graph measuring the bioactivity of *E. coli* cells harboring nematicidal Crystal protein (Crystal- *E. coli*) gene or empty vector (Vector- *E. coli*) on the nematode *Caenorhabditis elegans*. The concentration of both Crystal-*E. coli* and Vector-*E. coli* is $1.8 \times 10^7$ cell/mL in the *C. elegans* assays. Worms (n=10 per condition) were incubated at 25° C. for 16 hr. NT=not treated with carvacrol; T=treated with carvacrol.

DETAILED DESCRIPTION

Disclosed are methods of treating or preventing STH infection by administering to a subject a preparation of killed or inactive bacteria recombinantly expressing a nematicidal protein (e.g., crystal protein from *Bacillus thuringiensis*) in the cytosol of the bacterium. Such recombinant bacteria are treated with an anti-microbial agent such that the bacteria are killed before or during administration. In these particular methods, because the bacteria are dead when administered, any bacterium, including non-food grade bacteria, can be administered to a subject to treat an STH infection.

Microbes

In certain embodiments, the bacteria of the invention are non-sporulating bacteria. As used herein, the term "non-sporulating bacterium" includes wild-type bacteria that are incapable of producing spores (e.g., certain Gram-negative bacteria) as well as genetic variants of spore-forming bacteria that have been engineered to be defective in sporulation (e.g., certain Gram-positive bacteria). As used herein, unless the context makes clear otherwise, "a mutation resulting in a defect in sporulation" or "a genetic mutation that results in a defect in sporulation" refers to any genetic mutation that results in a defect in a member of the sporulation pathway and/or any genetic mutation that prevents the formation of viable spores.

In some embodiments, sporulation-deficient bacteria are advantageous. An example of a sporulation deficient bacterium is a spo0A- *Bacillus thuringiensis*. Any mutation or combination of mutations that confers sporulation deficiency but that does not substantially affect viability or heterologous gene expression can be used. These mutations include but are not limited to mutations in the following genes: kinA, kinB, spo0A, spo0B, spo0E, spo0F, spo0J, spo0M spoIIB, spoIID, spoIIE, spoIIF, spoIIG, spoIIL, spoIIM, spoIIIA, spoIIIB, spoIIIE, spoIVA, spoIVC, spoIVD, spoVG, spoVK, spoVL, spoVM, spoVN, spoVP, spoVQ, spoVID, σH, σF, σE, σG, and σK. (Silvaggi, J., et al. *Unmasking novel sporulation genes in Bacillus subtillus*. J Bacteriol. 186, 8089-8095, 2004; Sandman, K., et al. *Genetic Analysis of Bacillus subtilis spo Mutations Generated by Tn*917*-Mediated Insertional Mutagenesis*. Genetics. 117, 603-617, 1987; Malvar and Baum, Tn5401 *Disruption of the spoOF Gene, Identified by Direct Chromosomal Sequencing, Results in CryIIIA Overproduction in Bacillus thuringiensis*. J Bacteriol. 176, 4750-4753, 1994)

Bacteria are particularly applicable to the control of STHs because 1) recombinant bacteria can cheaply express large amounts of Cry proteins prior to administration into the GI tract of a mammalian subject, and Cry proteins so expressed, independent of any Cry proteins that may be secreted by bacteria in the GI tract, have been shown to have a significant impact on STHs, 2) studies using purified Cry protein to treat hookworms, whipworms, and *H. bakeri*, all in infected rodents, demonstrate that STHs in the mammalian GI tract can ingest and be killed/intoxicated by Cry proteins, 3) recombinant bacteria expressing a therapeutic protein, in which the protein is not purified, are cheaper to produce since no purified protein is needed, and 4) recombinant bacteria delivering STH curing proteins (e.g., Cry5B) are more effective that purified proteins (e.g., Cry5B) at the same bio-active protein dose (e.g., total Cry5B) in curing infections.

Microbes of the disclosed compositions and methods include killed and inactivated forms of *Bacillus* sp., including *Bacillus subtilis* (e.g., *Bacillus subtilis natto*, and *Bacillus subtilis* PY79), *B. cereus*, (e.g., *B. cereus* var. *Toyoi* (*Toyocerin*), *B. cereus* var. *toyoii*), *B. toyonensis*, *B. clausii*, *B. pumilus* and *Bacillus thuringiensis*. *Bacillus subtilis* has been extensively characterized as a safely ingested food additive in humans (see Example 14, infra, references 15-27). In certain exemplary embodiments, killed and inactive forms of *Bacillus thuringiensis* are used.

Other useful bacteria include but are not limited to non-sporulating variants of *Lactococcus* sp., *Lactobacillus* sp., *Bifidobacterium* sp., *Streptococcus* sp., *Clostridium* sp., *Sporolactobacillus* sp, *Sporosarcina* sp., *Brevibacillus* sp, *Leuconostoc* sp., *Pediococcus* sp., *Enterococcus* sp. and *Escherichia* sp. *Lactococcus* sp. includes but is not limited to *L. lactis*. *Lactobacillus* sp. includes but is not limited to *L. casei*, *L. paracasei*, *L. acidophilus*, *L. bulgaricus*, *L. delbrueckii* subsp. *bulgaricus*, *L. helveticus*, *L. plantarum*, *L. salivarius*, *L. reuteri*, *L. gasseri*, and *L. animalis*. *Bifidobacterium* sp. includes but is not limited to *B. animalis*, *B. bifidum*, *B. breve*, *B. infantis*, and *B. longum*. *Streptococcus* sp. includes but is not limited to *S. thermophilus*. *Clostridium* sp. includes but is not limited to *Clostridium butyricum*. *Sporolactobacillus* sp. includes but is not limited to *Sporolactobacillus vineae*. *Sporosarcina* sp. includes but is not limited to *Sporosarcina pasteurii*. *Brevibacillus* sp. includes but is not limited to *Brevibacillus laterosporus*.

Still other useful bacteria useful in connection with the claimed invention include killed and inactivated forms of Gram-negative bacteria. In certain exemplary embodiments, the Gram-negative bacteria include *E. coli* species (e.g., NISSLE 1917) and *Pseudomonas* species (e.g., *Pseudomonas fluorescens*). Exemplary Cry-expressing Gram-negative bacteria which can be killed or inactivated by the methods of the invention include the Cry-expressing *E. coli* strain of Ge et al. ("Hyperexpression of a *Bacillus thuringiensis* delta-endotoxin-encoding gene in *Escherichia coli*: properties of the product", Gene, 93: 49-54 (1990)) and the *P. fluorescens* strain of Peng et al. ("A Delta-endotoxin encoded in *Pseudomonas flurescens* displays a high degree of insecticidal activity", App. Microbiol Biotech., (2003), 63:300-306).

Nematicial Proteins

As used herein, unless the context makes clear otherwise, "nematicidal protein" refers to any protein that has toxic activity against nematodes or helminthes. Exemplary nematicidal proteins include crystal proteins such as the anthelmintic Cry proteins (e.g., Crickmore et al., 1998 *Microbiology and Molecular Biology Reviews* 62(3): 807-813; Schnepf et al., 1998 *Microbiology and Molecular Biology Reviews* 62(3): 775-806; including but not limited to the *B. thuringiensis* Cry proteins Cry5B (e.g., SEQ ID NO:1) and its subvariants, Cry13A (e.g., SEQ ID NO:2) and its subvariants, Cry14A (e.g., SEQ ID NO:3) and its subvariants, Cry21A (e.g., SEQ ID NOS:4-5) and its subvariants, and Cry6A and its subvariants (e.g., SEQ ID NO:6)) in the bacterium for delivery into a helminth (e.g., roundworm)-infected vertebrate animal gastrointestinal tract via oral dosing (gavage, drinking, eating, pill, capsule, powder, etc.). The Cry proteins are expressed in the cytosol of the bacterium, allowing access to the anthelmintic protein after the bacterium lyses or opens up either due to digestion within the gastrointestinal tractingestion and digestion of bacteria by the parasitic helminths (e.g., roundworms such as hookworms, whipworms, *Ascaris*, *Strongyloides*, veterinary parasitic roundworms of the intestine), etc.

In certain embodiments, a bacterium as provided herein may be introduced that expresses an individual Cry protein or that simultaneously expresses multiple Cry proteins. In some embodiments, multiple bacteria may be introduced, each of which expresses either a different individual Cry protein or simultaneously expresses multiple Cry proteins. In these and related embodiments, it is contemplated that the GI tract may be seeded with bacteria that express either one Cry protein or multiple Cry proteins at the same time. For example, due to the lack of cross-resistance between Cry5B-resistant roundworms and Cry21A-resistant roundworms, simultaneous administration of Cry5B and Cry21A in the gastrointestinal tract may inhibit the development of parasite resistance to the combination therapy.

In the long run, removing antibiotic selection capability (e.g., genetic selection markers) from the plasmids that are used to introduce heterologous Cry protein-encoding sequences, as well as using bacterial strains that are unable to replicate outside the vertebrate host, may be desirable in order to environmentally contain the genetically modified bacteria. For example, LAB (Lactic Acid Bacteria) have been engineered to be autotrophic in thymidine or thymine synthesis such that they can only grow in the vertebrate intestine where thymidine or thymine is present and not in the environment where thymidine or thymine is not present. See, e.g., Steidler L, et al. "Biological containment of genetically modified *Lactococcus lactis* for intestinal delivery of human interleukin 10." Nat Biotechnol 21: 785-789 (2003).

Cry-transformed bacteria such as *Bacilli* or LAB may be cultured and expression of intracellular, membrane-anchored, or secreted Cry protein by such bacteria may be confirmed using antibodies raised against each Cry protein and standard Western blotting or ELISA techniques.

To assess the bioactivity of all constructs, recombinant expressing Cry protein (full length, truncated, or variants) may be fed to the free-living nematode, *C. elegans*. Cry protein toxicity on *C. elegans* using LC50, brood-size, developmental inhibition assays on solid media and in liquid wells may then be quantitated. *C. elegans* can access the Cry proteins either via protein secreted onto the solid media/into the liquid well or by their ability to grind, open and digest bacteria. Confirmation that the recombinant bacteria are making bioactive Cry proteins may be obtained. Furthermore, the bioactivity (e.g., $LC_{50}$ in µg/mL) may be quantified and the constructs giving the highest activity determined.

Truncations, Variants, and Sub-Variants

The crystal proteins may be truncated to enhance their effectiveness. The usefulness of Bt toxins (e.g., crystal proteins) for controlling STHs may be limited by the protein size that STHs can ingest. Some parasitic roundworms poorly ingest proteins larger than about 40 kD. Thus, the effectiveness of any particular Bt toxin may be limited by size exclusion of proteins that STHs take in and so should be small enough to be readily absorbed by the STH gut while retaining toxic activity. A truncated toxin may be easier to express in bacteria. Producing a truncated toxin also alleviates the requirement that the target STH has the proper proteases present to correctly process full length protoxin (which is inactive) to a truncated, active toxin form. Thus, a truncated toxin is immediately available for intoxication independent of whether the proper protease processing enzymes are present in the STH target. Truncated toxin may also express at a higher level in microbes because truncated toxins are soluble and less likely to form insoluble inclusions in the cell expressing them, which could be toxic to the cell or which could make the toxin fold incorrectly. Accordingly, it is desirable to produce truncated Bt toxin fragments (e.g., crystal protein fragments). Moreover, fragments of certain Bt toxins have been tested and shown to retain toxic activity and have improved biological properties. By "truncated," when referring to a Bt toxin protein (crystal protein) is meant a Bt toxin protein that is not full-length but retains at least 5%, 10%, 20%, 30%, 40%, 50%, 60%, 70%, 80%, or 90% or more of the toxic activity of a corresponding full-length Bt toxin protein.

"Variants" or "subvariants" of Cry proteins include polypeptides with one or more substitutions, e.g., no more than 20 substitutions, alternatively no more than 10 substitutions, or substitutions at 10% or fewer of the residues, relative to a corresponding wild-type polypeptide or truncated version thereof. The variant, subvariant, or truncated polypeptide has at least 5%, 10%, 20%, 30%, 40%, 50%, 60%, 70%, 80%, or 90% of the activity, e.g., toxic activity, of the corresponding wild-type polypeptide or truncated version. Conservative substitutions include substitutions within the following groups: glycine, alanine, threonine, valine, isoleucine, leucine; aspartic acid, glutamic acid, asparagine, glutamine; serine, cysteine; lysine, arginine; aspartic acid, glutamic acid; serine, threonine; asparagine, glutamine; phenylalanine, tyrosine.

The crystal proteins may be full length, truncated, variants, or subvariants. The truncated crystal protein may include any truncation of the N- and C-termini that still retains toxin activity. The truncated form is not full-length but retains at least 5%, 10%, 20%, 30%, 40%, 50%, 60%, 70%, 80%, or 90% or more of the toxic activity of a corresponding full-length Bt toxin protein. For example, the truncated portion may be truncated between the end of conserved block 5 and the C-terminus of the full length protein.

In one embodiment, the truncated crystal protein may contain the toxin domain of the crystal protein and optionally include up to 5, 10, or 20 additional amino acids. The truncated crystal protein may be truncated after a conserved amino acid sequence of block 5 and optionally include up to 5, 10, or 20 additional amino acids. The conserved amino acid sequence of block 5 may contain the motif DRIEF (SEQ ID NO: 23), DRLEF (SEQ ID NO: 24), or some other related sequence as well as surrounding amino acid residues, e.g., three amino acids upstream and two amino acids downstream of this motif. Table 1 shows the block 5 sequences for various Cry proteins. See e.g., Schnepf, E., et al., *Bacillus thuringiensis* and Its Pesticidal Crystal Proteins, *Microbiology and Molecular Biology Reviews* 62(3): 775-806, (e.g., at p. 781, FIG. 3) (September 1998); and Crickmore et al., Revision of the Nomenclature for the *Bacillus thuringiensis* Pesticidal Crystal Proteins, *Microbiology and Molecular Biology Reviews* 62(3): 807-813 (September 1998). The truncated crystal protein may also be truncated at the N-terminus. For example, the truncated crystal protein may not contain the first about 1, 2, 3, 4, 5, 6, 7, 8, 9, 10, 15, 20, 25, 30, 35, 40, 45, or 50 amino acids at the N-terminus.

Cry protein variants can exhibit at least 50, 55, 60, 65, 70, 75, 80, 85, 86, 87, 88, 89, 90, 91, 92, 93, 94, 95, 96, 97, 98, or 99 percent amino acid sequence identity to a known Cry protein sequence such as any that are disclosed in Crickmore et al., 1998 *Microbiology and Molecular Biology Reviews* 62(3): 807-813, or in Schnepf et al., 1998 *Microbiology and Molecular Biology Reviews* 62(3): 775-806, including full length Cry proteins and truncated Cry proteins, Cry protein variants or subvariants thereof. Also contemplated according to certain embodiments are polynucleotides encoding such Cry proteins and truncations and variants thereof.

TABLE 1

| Protein | Block 5 Conserved Group |
|---------|------------------------|
| Cry1A | VYIDRIEFVP (SEQ ID NO: 7) |
| Cry3A | VYIDKIEFIP (SEQ ID NO: 8) |
| Cry4A | VLIDKIEFLP (SEQ ID NO: 9) |
| Cry5A | VFLDRIEFIP (SEQ ID NO: 10) |
| Cry5B | LFLDRIEFVP (SEQ ID NO: 11) |
| Cry7A | FYVDSIEFIP (SEQ ID NO: 12) |
| Cry8A | VYIDRIEFIP (SEQ ID NO: 13) |
| Cry9A | VYVDRIEFIP (SEQ ID NO: 14) |
| Cry10A | IYIDKIEFIP (SEQ ID NO: 15) |
| Cry12A | MVLDRIEFVP (SEQ ID NO: 16) |
| Cry13A | IYLDRLEFVP (SEQ ID NO: 17) |
| Cry14A | IFIDRIEFIP (SEQ ID NO: 18) |
| Cry19A | LILDKIEFLP (SEQ ID NO: 19) |
| Cry20A | FVLDKIELIP (SEQ ID NO: 20) |
| Cry21A | LFLDRIEFIS (SEQ ID NO: 21) |
| Consensus | i-iDkIEFiP (SEQ ID NO: 22) |

In Table 1, the consensus sequence denotes the positions at which at least 75% of the aligned proteins in the group have an identical or conserved amino acid sequence. An uppercase letter in the sequence indicates that at least 75% of the residues at that position are identical. A lowercase letter indicates that at least 75% of the residues at that position are conserved. Conserved amino acids fall into the following groups: a (A, G, S, T, or P); d (D, E, N, or Q); f (F, W, or Y) l I (I, L, M, or V), and k (K or R).

The truncated crystal protein may be a truncated form of Cry5B such as *B. thuringiensis* Cry5B (FIG. 2). Truncated Cry5B may extend from about amino acid 1, 2, 3, 4, 5, 6, 7, 8, 9, 10, 15, 20, 25, 30, 35, 40, 45, or 50 to at least about amino acid 693. The truncated form of Cry5B may optionally include up to an additional 5, 10, 20, 30, 40, or 50 amino acids from the C-terminus after conserved block 5, e.g., through about 698, 703, 713, 723, 733, or 743.

The truncated crystal protein may be a truncated form of Cry13A such as *B. thuringiensis* Cry13A (FIG. 3). Truncated Cry13A may extend from about amino acid 1, 2, 3, 4, 5, 6, 7, 8, 9, 10, 15, 20, 25, 30, 35, 40, 45, or 50 to at least about amino acid 688. The truncated form of Cry13A may optionally include up to an additional 5, 10, 20, 30, 40, or 50 amino acids from the C-terminus after conserved block 5, e.g., through about 693, 698, 708, 718, 728, or 738.

The truncated crystal protein may be a truncated form of *B. thuringiensis* Cry14A (FIG. 4). Truncated Cry14A may extend from about amino acid 1, 2, 3, 4, 5, 6, 7, 8, 9, 10, 15, 20, 25, 30, 35, 40, 45, or 50 to at least about amino acid 675. The truncated form of Cry14A may optionally include up to an additional 5, 10, 20, 30, 40, or 50 amino acids from the C-terminus after conserved block 5, e.g., through about 680, 685, 695, 705, 715, or 725.

The truncated crystal protein may be a truncated form of Cry21A such as *B. thuringiensis* Cry21Aa1 (FIG. 5A) or Cry21Aa2 (FIG. 5B). Truncated Cry21A may extend from about amino acid 1, 2, 3, 4, 5, 6, 7, 8, 9, 10, 15, 20, 25, 30, 35, 40, 45, or 50 to at least about amino acid 685. The truncated form of Cry21A may optionally include up to an additional 5, 10, 20, 30, 40, or 50 amino acids from the C-terminus after conserved block 5, e.g., through about 690, 695, 705, 715, 725, or 735.

Nucleic acid molecules encoding amino acid sequence variants, truncated versions, or both, of a Cry protein are prepared by a variety of methods known in the art. These methods include, but are not limited to, isolation from a natural source (in the case of naturally occurring amino acid sequence variants) or preparation by, for example, oligonucleotide-mediated (or site-directed) mutagenesis, PCR mutagenesis, and cassette mutagenesis of an earlier prepared variant or a non-variant version of protein. Moreover, the invention includes synthetic nucleic acid molecules where nucleotides are modified to include codons preferred in a particular organism, remove codons rarely used in a particular organism, or remove sequences that may inhibit transcription or RNA processing and the like.

Cry protein truncations may at least include conserved blocks 1-5. As seen in FIGS. 1A and 1B, alignment of known Cry toxins reveals five conserved sequence blocks (blocks 1-5) that are common to a majority of the proteins and are thought to be located in the active toxin domain. See de Maagd, R. A., et al. "How *Bacillus thuringiensis* has evolved specific toxins to colonize the insect world." TRENDS IN GENETICS 17(4): 193-99 (April 2001). Comparison of the carboxy-terminal halves of the sequences have suggested the presence of three additional blocks that lie outside of the active toxic core. See Schnepf, E., et al. "*Bacillus thuringiensis* and Its Pesticidal Crystal Proteins." MICROBIOLOGY AND MOLECULAR BIOLOGY REVIEWS 62(3): 775-806 (September 1998). Thus, Cry protein truncations may be truncated after the conserved amino acid sequence of block 5 (e.g., DRIEF (SEQ ID NO: 23) or DRLEF (SEQ ID NO: 24)). Alternatively, Cry protein truncations may be truncated after the conserved amino acid sequence of block 5 (e.g., DRIEF (SEQ ID NO: 23) or DRLEF (SEQ ID NO: 24)) plus an additional about 2, 3, 4, 5, 10, 15, 20, 25, 30, 35, 40, 45, or 50 amino acids of the c-terminal domain.

The complete amino acid sequence of Cry5Ba1 is listed in FIG. 2. The conserved amino acid sequence DRIEF (SEQ ID NO: 23) in Cry5B ends at amino acid number 693. Thus, a truncated form of Cry5B may include at least amino acids 50 through about 693. A truncated form of Cry5B may extend from about amino acid 1, 2, 3, 4, 5, 6, 7, 8, 9, 10, 15, 20, 25, 30, 35, 40, 45, or 50 to at least about amino acid 693. Alternatively or in addition to, a truncated form of Cry5B may include about 5, 10, 15, 20, 25, 30, 35, or 40 additional amino acids of the c-terminal domain.

The complete amino acid sequence of Cry13Aa1 is listed in FIG. 3. The conserved amino acid sequence DRLEF (SEQ ID NO: 24) in Cry13A ends at amino acid number 688. Thus, a truncated form of Cry13A may include at least amino acids 50 through about 688. A truncated form of Cry5B may extend from about amino acid 1, 2, 3, 4, 5, 6, 7, 8, 9, 10, 15, 20, 25, 30, 35, 40, 45, or 50 to at least about amino acid 688. Alternatively or in addition to, a truncated form of Cry13A may include about 5, 10, 15, 20, 25, 30, 35, or 40 additional amino acids of the c-terminal domain.

The complete amino acid sequence of Cry14Aa1 is listed in FIG. 4. The conserved amino acid sequence DRIEF (SEQ ID NO: 23) in Cry14A ends at amino acid number 675. Thus, a truncated form of Cry14A may include at least amino acids 50 through about 675. A truncated form of Cry5B may extend from about amino acid 1, 2, 3, 4, 5, 6, 7, 8, 9, 10, 15, 20, 25, 30, 35, 40, 45, or 50 to at least about amino acid 675. Alternatively or in addition to, a truncated form of Cry14A may include about 5, 10, 15, 20, 25, 30, 35, or 40 additional amino acids of the c-terminal domain.

The complete amino acid sequence of Cry21Aa1 and Cry21Aa2 are listed in FIGS. 5A and 5B, respectively. The amino acid sequence of Cry21Aa2 is about 98% identical to the sequence of Cry21Aa1. The conserved amino acid sequence DRIEF (SEQ ID NO: 23) in Cry21A ends at amino acid number 685. Thus, a truncated form of Cry21A may include at least amino acids 50 through about 685. A truncated form of Cry5B may extend from about amino acid 1, 2, 3, 4, 5, 6, 7, 8, 9, 10, 15, 20, 25, 30, 35, 40, 45, or 50 to at least about amino acid 685. Alternatively or in addition to, a truncated form of Cry21A may include about 5, 10, 15, 20, 25, 30, 35, or 40 additional amino acids of the c-terminal domain.

Anthelmintic Experiments

Once heterologous Cry protein expression and bioactivity are confirmed in a desired bacterium, the modified bacteria may be used for curative-type and preventative-type anthelmintic experiments.

Antibody production: Antibodies against recombinant Cry proteins (e.g., Cry5B, Cry21A, Cry14A, Cry13A, and Cry6A, full length and truncated proteins) may be produced and purified according to standard methodologies (e.g., *Current Protocols in Immunology*, John Wiley & Sons, New York, N.Y. (2009).

Bioactivity tests: To assess the bioactivity of all constructs, recombinant *bacilli* or other bacteria expressing heterologous Cry proteins are fed to the free-living nematode, *C. elegans*. *C. elegans* can access the Cry proteins either via protein secreted onto the solid media/into the liquid well, by protein naturally released as bacteria break open, or by their ability to grind and digest bacteria to open the bacterial cells.

Rodent and parasite tests: Three intestinal parasitic nematodes—*H. bakeri* (small intestine nematode parasite) in mice, and *Trichuris muris* (whipworm) in mice, and *A. ceylanicum* (hookworm) in hamsters are tested. The tests address: 1) where in the GI tract do heterologous Cry-expressing bacteria reside and for how long; and 2) how do these bacteria affect the acquisition and progression of intestinal nematode parasites.

Parasite tests: Naïve (uninfected) mice are gavaged with the best heterologous Cry-protein expressing recombinant bacterial strain(s) based on expression and bioactivity.

Protect against progression test: Mice are infected with *H. bakeri*. Two weeks later, infected mice are treated with heterologous Cry-protein expressing or control bacteria, respectively. Intestinal worm burdens and fecal egg counts are used to determine if the recombinant bacteria provide anthelmintic therapy in mice with pre-existing nematode infections.

Exemplary Parasites

The disclosed methods relate to the control of parasitic worms, e.g., nematodes and platyhelminths, using crystal proteins from *Bacillus* and their derivatives. Parasitic worms within the scope of the invention include but are not limited to those in Class Adenophorea, e.g., Order Mononchida, Family Plectidae, and Order Stichosomida, Family Mermithidae and Tetradonematidae; Class Secernentea, e.g., Order Rhabditida, Family Carabonematidae, Cephalobidae, Chambersiellidae, Heterorhabditidae, Oxyuridae, Panagrolaimidae, Rhabditidae, Steinernematidae, Syrphonematidae, Syrphonematidae, or Thelastomatidae; Order Spirurida, Family Filariidae, Onchocercidae, Physalopteridae, Syngamidae, Spiruridae, Subuluridae, or Thelaziidae; Order Diplogasterida, Family Diplogasteridae; and Order Tylenchida, Family Allantonematidae, Aphelenchidae, Aphelenchoididae, Entaphelenchidae, Fergusobiidae, Phaenopsitylenchidae, Sphaerulariidae, Anguinidae, Dolichodoridae, Belonolaimidae, Pratylenchidae, Hoplolamidae, Heteroderidae, Criconematidae, Tylenchulidae or Tylenehidae. In one embodiment, the parasite is from Class Secernentea, Order Ascaridida, Family Ascarididae; Class Adenophorea, Order Trichurida, Family Trichuridae; Class Secernentea, Order Strongylida, Family Ancylostomatidae (ancylostomidae) or Trichostrongylidae; or Class Secernentea, Order Spirurida, Family Dracunculidae, Filariidae, or Onchocercidae.

The parasite may be a helminth. Helminths within the scope of the invention include but are not limited to those from Phylum Annelida, Class Polychaetae, Class Myzostomida, Class Clitellata, Subclass Hirudinea, Order Gnathobdellidae, Order Rhynchobdellidae; Phylum Platyhelminthes (Flatworms), Class Turbellaria, Class Monogenea, Order Monopisthocotylea, Order Polyopisthocotylea, Class Trematoda, Subclass Aspidogasrea, Subclass Digenea; Super Order Anepitheliocystida, Order Strigeatida, Family Schistosomatidae, Subfamily Schistosomatinae, Genus *Schistosoma*, Order Echinostomatida, Family Fasciolidae, Family Paramphistomatidae, Family Echinostomatidae; Super Order Epitheliocystida, Order Plagiorchiida, Family Dicrocoeliidae, Family Troglotrematidae, Order Opisthorchiida, Family Heterophyidae, Family Opisthorchiidae, Class Cestoda, Subclass Cestodaria, Subclass Eucestoda, Order Pseudophyllidea, Family Diphyllobothriidae, Order Cyclophyllidea, Family Taeniidae, Family Hymenolepididae, Family Dilepididae, Family Mesocestoididae, Order Tetraphyllidea, Order Proteocephalata, or Order Spatheobothridea. For example, Cry proteins with the scope of the invention may be employed to prevent, inhibit or treat Roundworm, Whipworm, Hookworm, Schistosome, or Trematodes.

The parasite may also be gastrointestinal tract parasitic roundworms/nematodes. The gastrointestinal tract parasitic roundworms/nematodes may include but are not limited to the following species: *Haemonochus, Cooperia, Ostertagia, Trichostrongylus, Teladorsagia, Nematodirus, Ancylostoma,* Cyathostominea/Cyathostomin/Cyathostome, *Strongylus, Parascaris, Ascaris, Trichuris,* Oesophagostomum/Oesophagustomum, *Trichiuris, Bunostomum, Oxyuris, Chabertia, Habronema, Draschia, Triodontophorus, Toxocara, Toxascaris,* and *Uncinaria*. *Haemonochus* species includes but is not limited to *Haemonchus contortus* and *Haemonchus placei, Cooperia* species includes but is not limited to *Cooperia oncophora, Cooperia pectinata,* and *Cooperia curticei. Ostertagia* species includes but is not limited to *Ostertagia ostertagi, Ostertagia (Teladorsagia) circumcincta,* and *Ostertagia trifurcate. Trichostrongylus* species includes but is not limited to *Trichostrongylus axei, Trichostrongylus colubriformis,* and *T. circumcincta. Teladorsagia* species includes but is not limited to *Teladorsagia (Ostertagia) circumcincta. Nematodirus* species includes but is not limited to *Nematodirus spathiger. Ancylostoma* species includes but is not limited to *Ancylostoma caninum, Ancylostoma braziliense,* and *Ancylostoma tubaeforme.* Cyathostominea/Cyathostomin/Cyathostome nematodes are also included. *Strongylus* species (small and large) includes but is not limited to *Strongylus vulgaris, Strongylus equinus,* and *Strongylus edentatus. Parascaris* species includes but is not limited to *Parascaris equorum. Strongyloides* species includes but is not limited to *Strongyloides westeri. Ascaris* species includes but is not limited to *Ascaris suum. Trichuris* species includes but is not limited to *Trichuris globulosa, Trichuris suis, Trichuris campanula,* and *Trichuris vulpis.* Oesophagostomum/Oesophagustomum species includes but is not limited to *Oesophagustomum dentatum, Oesophagustomum quadrispinulatum, Oesophagostomum columbianum,* and *Oesophagostomum venulosum. Trichiuris* species includes but is not limited to *Trichiuris ovis. Bunostomum* species includes but is not limited to *Bunostomum trigonocephalum. Oxyuris* species includes but is not limited to *Oxyuris equi* (pin worms). *Chabertia* species includes but is not limited to *Chabertia ovina. Habronema* species includes but is not limited to *Habronema microstoma* and *Habronema muscae. Draschia* species includes but is not limited to *Draschia megastoma. Triodontophorus* species includes but is not limted to *Triodontophorus minor* and *Triodontophorus serrates. Toxocara* species includes but is not limted to *Toxocara canis* and *Toxocara cati. Toxascaris* species includes but is not limted to *Toxascaris leonine. Uncinaria* species includes but is not limted to *Uncinaria stenocephala*. Human parasitic roundworms of the gastrointestinal tract include but are not limited to the hookworms *Ancylostoma duodenale* and *Necator americanus*, the whipworm *Trichuris trichiura*, the roundworm *Ascaris lumbricoides*, the threadworm *Strongyloides stercoralis*, and the pinworm *Enterobius vermiculari*.

Anti-Microbial Agents

In the disclosed methods, the recombinant bacteria expressing a crystal protein can be treated with an anti-microbial agents. Anti-microbial agents can be used on the recombinant bacteria before administration to a subject, or concomitant with administration to the subject. An advantage of killing the recombinant bacteria is that otherwise non-food safe bacteria can be used in the disclosed methods. Such non-food safe bacteria, such as *Bacillus thuringiensis* which is closely related to *Bacillus cereus* that can cause food poisoning, express very high levels of Cry proteins such as Cry5B and improve the efficacy of the protein when co-administered versus when the protein is administered in a pure form without the bacterium Suitable anti-microbial agents are those that (1) sufficiently kill the recombinant bacteria; and (2) do not substantially affect the activity and/or levels of the crystal protein. Examples of suitable anti-microbial agents include, but are not limited to, antibiotics (such as a beta-lactam antibiotic), bacteriocidal agents, iodine, terpenes, formaldehyde, and irradiation. Examples of terpenes include, but are not limited to, thymol, eugenol, geraniol, carvacrol, and citral, or a combination thereof. Carvacrol is especially useful.

Additional Therapeutic Agents

In certain embodiments the crystal protein-recombinant bacteria are administered in combination with at least one additional therapeutic agent. This additional agent can be, for example, a bacterium expressing or capable of expressing, a crystal protein, a small molecule, or a polypeptide (including antibodies and fragments thereof). In a further embodiment, the additional therapeutic is a nicotinic acetylcholine receptor agonist. In certain embodiments, the additional therapeutic agent is administered simultaneously with recombinant bacteria. In certain embodiments the additional therapeutic agent is administered sequentially (and in either order) with the recombinant bacterium. In certain embodiments, the nicotinic acetylcholine receptor agonist is from the levamisole family of nicotinic acetylcholine receptor agonists. In certain embodiments, the nicotinic acetylcholine receptor agonist is levamisole. In certain embodiments, the levamisole is administered in an amount of about 0.1 mg/kg to about 5.0 mg/kg. In certain embodiments the nicotinic acetylcholine receptor agonist is pyrantel or tribendimidine. In certain embodiments, the pyrantel is administered in an amount of about 1.0 mg/kg to about 15.0 mg/kg. In certain embodiments, the tribendimidine is administered in an amount of about 0.25 mg/kg to about 10 mg/kg.

Administration, Dosage Forms, Pharmaceutical Compositions

The present invention describes compositions and methods for administration of killed or inactivated bacterial cells to the gastrointestinal tract of a subject. The methods include administering the bacteria in food or as a food supplement. Oral administration is preferably in an aqueous suspension, emulsion, powder or solid. The composition may be formulated into a food or added to food by the user prior to consumption. Administration to the gastrointestinal tract may also be in the form of an anal suppository (e.g., in a gel or semi-solid formulation). All such formulations are made using standard methodologies.

The method is typically practiced on any animal where inhibiting pathogen or parasites is desired. In certain embodiment, the animal is a human. However, the animal can be any livestock or zoological specimen where such inhibition of parasites/pathogens provides economic and health benefits. Any animal can benefit by the claimed methods, including birds, reptiles, mammals such as horses, cows, sheep, goats, pigs, and the like domesticated animals, or any of a variety of animals of zoological interest. Other purposes are readily apparent to one skilled in the arts of nutrient absorption, feed utilization and bioavailability.

The present invention further contemplates a therapeutic system for treating, reducing and/or controlling parasitic infections. Typically, the system is in the form of a package containing a therapeutic composition of the present invention, or in combination with packaging material. The packaging material includes a label or instructions for use of the components of the package. The instructions indicate the contemplated use of the packaged component as described herein for the methods or compositions of the invention. By way of example, and not of limitation, a system can comprise one or more unit dosages of a therapeutic composition according to the present invention. Alternatively, the system can alternately contain bulk quantities of a therapeutic composition. The label contains instructions for using the therapeutic composition in either unit dose or in bulk forms as appropriate, and may also include information regarding storage of the composition, disease indications, dosages, routes and modes of administration and the like information.

Furthermore, depending upon the particular contemplated use, the system may optionally contain either combined or in separate packages one or more of the following components: bifidogenic oligosaccharides, flavorings, carriers, and the like components. One particularly preferred embodiment comprises unit dose packages of bacterial cells for use in combination with a conventional liquid product, together with instructions for combining the bacteria with the formula for use in a therapeutic method.

Different dosage regimens may be used in the disclosed methods. In some embodiments, a daily dosage is administered once, twice, three times, or four times a day for one, two, three, four, five, six, seven, eight, nine, or ten days. In some embodiments, a once- or twice-daily dosage is administered every other day.

Administration of the compositions containing the active ingredients effective in inhibiting parasite growth in the intestine and in feces generally consist of one to ten unit dosages of 10 mg to 10 g per dosage of the composition for one day up to one month for a human of approximately 100 kg body weight. Unit dosages are generally given once every twelve hours and up to once every four hours. Preferably two to four dosages of the composition per day, each comprising about 0.1 g to 50 g per dosage, for one to seven days are sufficient to achieve the desired result.

A preferred method involves the administration into the digestive tract of from $1\times10^2$ to $1\times10^{10}$ of bacterium per day, in some embodiments from $11\times10^3$ to $1\times10^6$, in other embodiments from $1\times10^6$ to $1\times10^9$, and more preferably about from $5\times10^8$ to $1\times10^9$ bacterium per day. Exemplary dosages range from about $1\times10^3$ to $1\times10^6$ bacterium per day, or alternatively range from about $1\times10^6$ to $1\times10^9$ bacterium per day.

In various specific embodiments, an effective dose of a composition of the present disclosure can be in a range of from 1.0 gm to 15.0 gm for an adult patient, more preferably between about 2.0 gm and about 10.0 gm of the composition. Effective doses can be administered to a subject at any suitable frequency, e.g., at least once a week, preferably once a day. Pediatric dosages may be in the range of 15% to 90% of adult dosages.

In other embodiments, a constant dosage of the composition can be administered over time, for example about 2 gm to about 4 gm per day, up to about 6 g to about 10 g per day, depending on the severity of the physiological condition. Once the infection has been effectively ameliorated, the subject can in many instances decrease the dosage to about 2 gm to about 4 gm per day for maintenance purposes. The desired dose may be presented in multiple (e.g., two, three, four, five, six, or more) sub-doses administered at appropriate intervals throughout the day.

The pharmaceutical compositions comprising the crystal protein-expressing recombinant bacteria can be administered via any of the accepted modes of administration or agents known in the art. However, oral administration is preferred because this route of delivery delivers the recombinant bacteria to the GI tract. The dosage form can be, for example, a solid, semi-solid, lyophilized powder, or liquid dosage forms, such as for example, tablets, pills, soft elastic or hard gelatin capsules, powders, solutions, suspensions, suppositories, aerosols, or the like, and can be in unit dosage forms suitable for simple administration of precise dosages. One exemplary embodiment of the dose form is a capsule containing the composition of the disclosure including the bacterial species in a dried form, blended with pharmaceutical carrier. The capsule for such dose form can be of any suitable type, e.g., a gelatin capsule of a conventional variety.

The physiologically compatible carrier medium with which the bacterial species are employed, can be of any simple type, e.g., a pharmaceutically acceptable carrier such as fructo-oligo-saccharide (FOS) medium, or other soluble fiber, sugar, nutrient or base material for the composition, with which the bacterial species can be formulated, e.g., in an orally administrable form. Other carrier media include mannitol, inulin (a polysaccharide), polydextrose, arabinogalactan, polyolslactulose, lactitol, etc. A wide variety of materials can be used as carrier material in the practice of the present disclosure, as will be apparent to those of ordinary skill in the art, based on the description herein.

The carrier medium, when present, can be blended with the bacterial species in any suitable amounts, such as an amount of from 5% to 95% by weight of carrier medium, based on the total weight of the bacterial species and the carrier medium, in various embodiments. In other embodiments, the amount of carrier medium may be in a range having a lower limit of any of 5%, 10%, 12%, 15%, 20%, 25%, 28%, 30%, 40%, 50%, 60%, 70% or 75%, and an upper limit, higher than the lower limit, of any of 20%, 22%, 25%, 28%, 30%, 40%, 50%, 60%, 70%, 75%, 80%, 85%, 90%, and 95%. The amount of carrier medium in a specific embodiment may be determined based on considerations of the specific dose form, relative amounts of the bacterial species, the total weight of the composition including the carrier medium and the bacterial species, and the physical and chemical properties of the carrier medium, and other factors, as known to those of ordinary skill in the probiotic formulation art.

In certain embodiments, the bacterial cells are formulated in a composition that protects the cells and/or Cry proteins from the acid environment of the stomach. Accordingly, the invention includes a composition containing a bacterium and a pharmaceutically-acceptable acid-resistant ("enteric") carrier. By acid-resistant is meant that the carrier or coating does not dissolve in an acidic environment. An acidic environment is characterized by a pH of less than 7. The acid-resistant carrier is resistant to acids at pH less than about 4.0. Preferably, the carrier does not dissolve in pH 2-3. Most preferably, it does not dissolve in pH of less than 2. To protect bacterial cells from stomach acids, the cells are coated or encapsulated with the acid-resistant carrier.

In certain embodiments, the coating is pH-sensitive. For example, the coating may dissolve after the pH is greater than 4.0. For example, the coating dissolves in a neutral environment as is encountered in the small intestine, and does not dissolve in an acidic environment as is encountered in the stomach. Alternatively, the enteric coating dissolves when exposed to specific metabolic event such as an encounter with a digestive enzyme that is found in the small intestine. For example, the coating is digested by a pancreatic enzyme such as trypsin, chymotrypsin, or a pancreatic lipase. The formulation is hydrated in the small intestine. Digestion or dissolution of the coating allows liberation of bacterial cells, e.g., Bacillus cells, into the intestine.

In other embodiments, bacterial cells are stabilized in a gel or paste such as an anhydrous carbohdrate paste. In alternate formulations, the cells are lyophillized and/or suspended in a gel or paste. Enteric coating materials are known in the art, e.g., malic acid-propane 1,2-diol. Cellulose derivatives, e.g., cellulose acetate phthalate or hydroxypropyl methylcellulose phthalate (HPMCP), are also useful in enteric acid-resistant coatings. Other suitable enteric coatings include cellulose acetate phthalate, polyvinyl acetate phthalate, hydroxypropylmethylcellulose phthalate and anionic polymers of methacrylic acid and methyl methacrylate. Another suitable enteric coating is a water emulsion of ethylacrylate methylacrylic acid copolymer, or hydroxypropyl methyl cellulose acetate succinate (HPMAS). (See, e.g., U.S. Pat. No. 5,591,433). An enteric coating is designed to resist solution in the stomach and to dissolve in the neutral or alkaline intestinal fluid. In certain embodiments, the bacterial cells are preferably formed into dry powders. Suitable drying methods include a natural drying, a forced-air drying, a spray drying, a freeze drying, and the like. Of those, a spray drying, drum drying or a forced-air drying are preferably used. A protective agent such as skim milk, sodium glutamate, and saccharides may be used in a time of drying. As saccharides, glucose and trehalose may be used.

Auxiliary and adjuvant agents may include, for example, preserving, wetting, suspending, sweetening, flavoring, perfuming, emulsifying, and dispensing agents. Prevention of the action of contaminating microorganisms, if desired, can be accomplished using various antibacterial and antifungal agents, such as, parabens, chlorobutanol, phenol, sorbic acid, and the like. Isotonic agents, such as sugars, sodium chloride, and the like, may also be included.

Solid dosage forms can be prepared with coatings and shells, such as enteric coatings and others well-known in the art. They can contain pacifying agents and can be of such composition that they release the active compound or compounds in a certain part of the intestinal tract in a delayed manner Examples of embedded compositions that can be used are polymeric substances and waxes. The active compounds also can be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., the active agent (such as the recombinant bacteria), and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethyl formamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Actual methods of preparing such dosage forms are known, or will be apparent, to those skilled in this art. Reference is made, for example, to Remington's Pharmaceutical Sciences, 18th ed. (Mack Publishing Company, Easton, Pa., 1990).

Methods

The methods are directed to treating a parasitic worm or helminth infection in a subject comprising administering to the subject a therapeutically effective amount of a composition comprising an anti-microbial agent treated recombinant bacterium that is engineered to express a crystal protein.

Furthmore, the methods are directed to reducing the severity of a parasitic worm or helminth infection comprising administering to the subject a therapeutically effective amount of a composition comprising an anti-microbial agent treated recombinant bacterium that is engineered to express a crystal protein.

Selected Definitions

As used herein, unless the context makes clear otherwise, "treatment," and similar words such as "treated," "treating" etc., indicates an approach for obtaining beneficial or desired results, including and preferably clinically desirable results. Treatment can involve optionally either the amelioration of symptoms of the disease or condition, or the delaying of the progression of the disease or condition.

As used herein, unless the context makes clear otherwise, "subject" means a vertebrate, such as a mammal. The mammal can be a feline, a rodent, a canine, a bovine, a equine, a swine, a caprine, an ovine, or a primate. In some embodiments, the subject is a human.

As used herein, unless the context makes clear otherwise, "reducing the likelihood of occurrence," "prevention," and similar words such as "prevented," "preventing" etc., include approaches for preventing, inhibiting, or decreasing the likelihood of the onset or recurrence of a disease or condition, in a manner that exhibits statistical significance, for example, when compared to the results obtained when the indicated method steps are omitted. Similarly, also included are preventing, inhibiting, or decreasing the likelihood of the occurrence or recurrence of the symptoms of a disease or condition, or optionally delaying the onset or recurrence of a disease or condition, or delaying the occurrence or recurrence of the symptoms of a disease or condition. As used herein, "prevention" and similar words also include reducing the intensity, effect, symptoms and/or burden of a disease or condition prior to onset or recurrence of the disease or condition. Methods according to these and related embodiments may be practiced using an effective amount or a therapeutically effective amount of an agent that substantially eradicates, reduces the severity of, or reduces the likelihood of occurrence of a soil-transmitted helminth (STH) infection. As used herein, an "effective amount" or a "therapeutically effective amount" of a composition, agent or substance is that amount sufficient to obtain a desired biological effect, such as beneficial results, including clinical results.

In certain preferred embodiments, the herein described compositions for treating or reducing the severity or likelihood of occurrence of an STH infection are formulated as pharmaceutical compositions, which will preferably be formulated for oral delivery. Pharmaceutical compositions are formulated so as to allow the agent(s) contained therein to be bioavailable upon administration of the composition to a human.

It will be appreciated that the practice of the several embodiments of the present invention will use, unless indicated specifically to the contrary, conventional methods in virology, immunology, microbiology, molecular biology and recombinant DNA techniques that are within the skill of the art, and many of which are described below for the purpose of illustration. Such techniques are explained fully in the literature. See, e.g., *Current Protocols in Molecular Biology* or *Current Protocols in Immunology*, John Wiley & Sons, New York, N.Y. (2009); Ausubel et al., *Short Protocols in Molecular Biology*, 3$^{rd}$ ed., Wiley & Sons, 1995; Sambrook and Russell, *Molecular Cloning: A Laboratory Manual* (3rd Edition, 2001); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984) and other like references.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

As used in this specification and the appended claims, the singular forms "a," "an" and "the" include plural references unless the content clearly dictates otherwise. Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers. Each embodiment in this specification is to be applied mutatis mutandis to every other embodiment unless expressly stated otherwise.

EXAMPLES

The following Examples are presented by way of illustration and not limitation.

Example 1

Expression of Cry Proteins in *Bacillus*

*Bacillus thurengiensis, Bacillus cereus* (e.g., var. *toyoi*, var. *toyoii*), *Bacillus toyonensis, Bacillus thuringiensis* (e.g., var. HD1), or *Bacillus subtilis* (e.g., var. PY79, var. *natto*) is used to express Cry proteins using either sporulation promoters (stationary phase/early sporulation Cry3A, late sporulation Cry5B) or a constitutive promoter (e.g., the mbg promoter). See, e.g., Shao X, et al. "Surface display of heterologous proteins in *Bacillus thuringiensis* using a peptidoglycan hydrolase anchor." Microb Cell Fact 8: 48 (2009). These constructs are transformed into *B. cereus, B. toyonensis, B. thuringiensis*, and *B. subtilis* strains and are tested for expression and bioactivity as described below. In addition, strong expression promoters (constitutive and inducible) have been made for *B. subtilis*, and these and other genetic elements described herein are referred to as being "operably linked" when they are present in a polynucleotide construct and situated in a manner that permits them to exert the desired function, such as promotion of specific gene transcription (See, e.g. Phan T T, et al. "Novel plasmid-based expression vectors for intra- and extracellular production of recombinant proteins in *Bacillus subtilis*." PROTEIN EXPR PURIF 46: 189-195 (2006). Secreted versions of proteins are made by addition of the signal peptide of the amyQ gene. See id. Thus, similar expression/curative experiments are carried out using *Bacillus subtilis* as the probiotic strain.

Example 2

Curative Experiment A—Protocol for Infections, Anthelmintic Treatment, and Determination of Treatment Efficacy (Small Intestine Roundworm Parasite)

Six week old female Swiss Webster mice are infected per os with a suspension of 200±10 *Heligmosomoides bakeri* infective third-stage larvae in 0.1 mL of distilled water. The outbred strain Swiss Webster is used to better "mimic" treating a genetically diverse host (like humans). Each mouse is gavaged on day 15 post-infection (PI) with 0.1 mL of buffer, 0.1 mL of high dose sporulation-defective bacterium such as spo0A-*Bacilli* (alive or dead) control (transformed with empty vector) or 0.1 mL of high dose bacteria expressing Cry protein (6-10 animals/group). Progression of the infection is determined by fecal egg counts every other day beginning 3 days before treatment. Mice are placed individually in empty plastic cages for 1 h each morning, and the fecal pellets are collected into 50 mL centrifuge tubes. The number of eggs present is counted using the modified McMaster technique. See Hu Y, et al. "*Bacillus thuringiensis* Cry5B protein is highly efficacious as a single-dose therapy against an intestinal roundworm infection in mice." PLOS NEGL TROP DIS 4: e614 (2010). At 1, 2, or 3 weeks after treatment, the animals from all three groups are euthanized and the intestinal worm burdens are counted. Using fecal egg counts and intestinal worm burdens, the ability of Cry-expressing sporulation-defective bacterium such as spo0A-*Bacilli* (alive or dead) to cure small intestinal roundworm infections are ascertained.

Example 3

Curative Experiment B—*Trichuris Muris*: Whipworm

Large Intestine Roundworm Parasite

Twenty-one (21) 6-8 week old female AKR mice are infected per os with 200 infectious-staged *T. muris* eggs. Thirty (30) days post-infection, the mice are treated per os (7/group) with a single 0.1 mL dose of buffer, 0.1 mL high dose of sporulation-defective bacterium such as spo0A-*Bacilli* (alive or dead) control (transformed with empty vector), or 0.1 mL of high dose sporulation-defective bacterium such as spo0A-*Bacilli* (alive or dead) expressing Cry protein. Fecal egg counts are taken three days before treatment and then every other day until necropsy (same protocol to collect eggs as per *H. bakeri*). The mice are euthanized either 1, 2 or 3 weeks after treatment and worm burdens in the large intestine are determined. Using fecal egg counts and intestinal worm burdens, the ability of Cry-expressing sporulation-defective bacterium such as spo0A-*Bacilli* (alive or dead) to cure large intestinal roundworm infections are ascertained.

Example 4

Curative Experiment C—*Ancylostoma Ceylanicum*: Hookworm (Blood Feeding, Small Intestinal Roundworm Parasite)

Twenty one (21) 4-week old Syrian hamsters are infected per os with 150 infectious staged L3 *A. ceylanicum* hookworm larvae. Fourteen (14) days post-infection, the hamsters are treated per os with a single 0.1 mL dose of buffer, 0.1 mL high dose of sporulation-defective bacterium such as spo0A-*Bacilli* (alive or dead) control (transformed with empty vector), or 0.1 mL of high dose sporulation-defective bacterium such as spo0A-*Bacilli* (alive or dead) expressing Cry protein. Body weight, hemoglobin levels, and fecal egg counts (beginning three days before treatment) are monitored every other day until day 21, 28, or 35, at which point the animals are euthanized and worm burdens in the small intestine are determined. Using fecal egg counts, hemoglobin levels, and intestinal worm burdens, the ability of Cry-expressing sporulation-defective bacterium such as spo0A-*Bacilli* (alive or dead) to cure blood-feeding small intestinal roundworm infections are ascertained.

Studies of *Ancylostoma ceylanicum* hookworms in Syrian hamsters were carried out as previously described (Hu, Y., et al. *PLoS One*, 8, e70702, 2013; Hu, Y., et al. *Appl Environ Microbiol*, 79, 5527-5532, 2013). Briefly, 4-6 week old male hamsters were infected with 150 infectious third staged larvae per os. On day 17 post-infection, an overnight collection of stool is taken and fecal egg counts (FECs) taken the next day. The hamsters are assigned to groups based on FEC so that there is roughly the same level of infection (same average egg per gram of feces or EPG) in all groups. On day 18 post-infection, the hamsters are weighed for dosing purposes and then gavaged with treatments as described in each experiment. On day 21 post-infection, another overnight collection of stool is taken for FECs. On day 22 post-infection, the animals were euthanized. Total hookworms in the small intestine were counted and EPGs calculated.

Studies of *Necator americanus* hookworms in Syrian hamsters were carried out similarly with the following differences. Following subcutaneous (subq) infection with 150 infectious third staged larvae, hamsters were injected daily with 200 µL of 4 mg/mL dexamethasone to suppress immunological responses that expel the parasites (Fujiwara, R., et al. *Parasite Immunol*, 28, 285-293, 2006). Treatments were conducted on day 57 post-infection and hookworm burdens/final FECs determined on day 61 post-infection.

For all experiments involving cimetidine, hamsters or mice were pre-gavaged with 200 µL of an 8.75% cimetidine solution 15 minutes prior to therapeutic treatment (Stepek, G., et al. *Parasitology*, 134, 103-112, 2007).

Example 5

Preventative-Type Experiment A

Swiss Webster mice as above (6-10 each group, three groups) received either 0.1 mL buffer, 0.1 mL high dose empty vector-transformed sporulation-defective bacterium such as spo0A-*Bacilli* (alive or dead) without Cry protein expression, or 0.1 mL high dose vector-transformed sporulation-defective bacterium such as spo0A- *Bacilli* (alive or dead) with Cry protein expression. Some (about 2-21) days later, all groups of mice are then challenged with 200 *H. bakeri* infectious larvae as described above. Two weeks later after infection challenge, fecal egg counts are determined every other day for one to two weeks, after which time the mice are euthanized to determine intestinal roundworm burdens. Fecal egg counts and intestinal roundworm burdens are used to determine if the probiotics protected the mice against a challenge with a small intestine roundworm parasite (i.e., prevented infection).

Example 6

Preventative-Type Experiment B

AKR mice as above (6-10 each group, three groups) receive either 0.1 mL buffer, 0.1 mL high dose empty vector-transformed sporulation-defective bacterium such as spo0A- *Bacilli* (alive or dead) without Cry protein expression, or 0.1 mL high dose vector-transformed sporulation-defective bacterium such as spo0A- *Bacilli* (alive or dead) with Cry protein expression. Some (about 2-21 days later, all groups of mice are then challenged with 200 *T. muris* infectious eggs as above. Thirty (30) days after infection challenge, fecal egg counts are determined every other day for one to two weeks, after which time the mice are euthanized to determine intestinal roundworm burdens. Fecal egg counts and intestinal roundworm burdens are used to determine if the probiotics protected the mice against a challenge with a large intestine roundworm parasite (i.e., prevented infection).

Example 7

Preventative-Type Experiment C

Hamsters as above (6-10 each group, three groups) receive either 0.1 mL buffer, 0.1 mL high dose empty vector-transformed LAB without Cry protein expression, or 0.1 mL high dose vector-transformed sporulation-defective bacterium such as spo0A- *Bacilli* (alive or dead) with Cry protein expression. Some (about 2-21) days later, all groups of hamsters are then challenged with 150 *A. ceylanicum* infectious larvae as above. Two weeks after infection challenge, fecal egg counts are determined every other day for one to two weeks, after which time the hamsters are euthanized to determine intestinal roundworm burdens. Fecal egg counts and intestinal roundworm burdens are used to determine if the treatment protected the hamsters against a challenge with a small intestine blood-feeding roundworm parasite (i.e., prevented infection). In addition to experiments with rodents described above, similar experiments could be carried out with other mammals, e.g., felines, canines, bovines, equines, swines, caprines, ovines, and primates.

Example 8

*Bacillus Subtilis* Strain Engineered for Treatment of STHs

Construction and verification of strains and preparation of lysates. The *B. subtilis* strain PY79 was transformed with the plasmid vector pHT3101 (PY79-vector) or with a pHT3101-derived cry5B plasmid (PY79-Cry5B) (29). Natural competence was generated in PY79 by use of a standard medium shift protocol (30). To generate spore lysates and spore crystal lysates, PY79 strains were sporulated for 96 h at 37° C., spun down, washed once with prechilled 0.5M NaCl, and washed again with prechilled sterile double-distilled water. Final pellets were stored at −80° C. until use.

Transformants were screened by PCRs using the following primers on all three strains (PY79, PY79-vector, and PY79-Cry5B): Cry5B primer forward 1 (CGTTCAAAAT-CATCCGTAAATG) (SEQ ID NO: 26) with Cry5B primer reverse 1 (AAATGCATGAACCACTTCCAC) (SEQ ID NO: 27) (predicted product of 586 nucleotides [nt]), Cry5B primer forward 2 (TGGCAACAATTAATGAGT TGTATCCAG) (SEQ ID NO: 28) with Cry5B primer reverse 2 (CTGCCTTGACAAATGG CTACT) (SEQ ID NO: 29) (predicted product of 497 nt), and pHT3101 primer forward (CACCCCAGGCTTTACACTTTA) (SEQ ID NO: 30) with pHT3101 primer reverse (AGG CGAT-TAAGTTGGGTAACG) (SEQ ID NO: 31) (predicted product of 220 nt with empty vector pHT3101 and 6.5 kb with the cry5B insert). Templates were prepared as follows.

Single colonies of PY79, PY79-vector, and PY79-Cry5B were picked from plates and suspended in 50 μl of sterile double-distilled water. These bacterial solutions were boiled for 3 min and then snap-frozen in liquid nitrogen for 3 min. The procedure was repeated for a total of three cycles of boiling-freezing. Supernatants were collected and used as PCR templates. Cycles were carried out using Taq polymerase under the following conditions: 94° C. for 3 min and then 35 cycles of 94° C. for 30 s, 54° C. for 45 s, and 72° C. for 1 min, followed by 72° C. for 10 min. All amplified products were sequenced to confirm identities. To determine putative transcription factor binding sites, 1.5 kb of the region upstream of the cry5B start codon was entered into the DBTBS database and the P value was set to 0.05. Two putative sigma E binding sites were revealed, 43 and 712 bases upstream of the start codon.

The identity of the strains was further confirmed by analysis of selected proteins. Cell lysates were fractionated by 8% SDS-PAGE, and protein bands were excised from the gels. Proteins were prepared for mass spectrometric sequencing by in-gel digestion with trypsin and then analyzed by high-pressure liquid chromatography (HPLC) in combination with tandem mass spectroscopy (MS/MS) using electrospray ionization as described previously (32). The collected data were analyzed using MASCOT (Matrix Sciences) and Protein Pilot 4.0 (AB Sciex) for peptide identifications.

SEM. In preparation for scanning electron microscopy (SEM) imaging, the samples were drop-cast on a polished Si chip and dried in a vacuum. The samples were then sputter coated with iridium in an Emitech K575X sputter coater. The sputter current was 85 mA, the argon pressure was 2 Pa, and the deposition time was 7 s, resulting in a film thickness of <10 nm. The samples were imaged with an FEI XL30 ESEM FEG instrument, using a 10-kV beam energy and a spot size of 3.

*C. elegans* bioassays and *A. ceylanicum* curative experiments. *Ancylostoma ceylanicum* hookworms were maintained in golden Syrian hamsters (14). All animal experiments were carried out under protocols approved by the UCSD or UMMS Institutional Animal Care and Use Committees (IACUC). All housing and care of laboratory animals used in this study conformed to the *Guide for the Care and Use of Laboratory Animals* (33) and all requirements and regulations issued by the USDA, including regulations implementing the Animal Welfare Act (P.L. 89-544) as amended (see 18-F23). *Caenorhabditis elegans* was maintained according to standard procedures (34).

The concentration of Cry5B protein in PY79-Cry5B spore crystal lysates was determined as previously described for Bt Cry5B spore crystal lysates (13). Dose-dependent *C. elegans* mortality bioassays (three independent trials) were carried out as previously described (13), including use of tetracycline at 30 µg/ml, except that the assays were carried out for 6 days and each well contained ~25 to 30 animals (with triplicate wells per experiment and three independent experiments). The 50% lethal concentration (LC50) was calculated using PROBIT (35).

For in vivo curative experiments, male hamsters were infected per os with 150 *A. ceylanicum* infectious larvae. On day 17 postinoculation (p.i.), a fecal sample was collected from each hamster, and the number of eggs was counted using the modified McMaster technique (13). On the basis of these fecal egg counts, the hamsters were segregated to ensure that the groups (control and treatment) had roughly equivalent infection levels. On day 18 p.i., hamsters were weighed individually and given either PY79-Cry5B spore lysate or a spore dose equivalent of PY79-vector spore lysate per os through a blunt-ended gavage needle. Feces were collected on days 1 and 3 post-treatment to determine fecal egg counts (13). The hamsters were sacrificed on day 22 p.i., and intestinal parasite burdens were determined as described previously (14). The one-tailed Mann-Whitney test was performed to compare the two groups for significance in the experiment using a dose of 10 mg/kg of body weight (data were calculated and plotted using Prism 5 [GraphPad Software Inc., La Jolla, Calif.]). Fecal egg counts were compared using one-tailed Student's t test. For the dose-response experiment, results for each treatment group were compared to those for the control group by one-way analysis of variance and Dunnett's method.

Results

Cry5B was well produced in *Bacillus subtilis* PY79. A recombinant cry5B plasmid engineered for *B. thuringiensis* (29) was purified from *B. thuringiensis* and transformed into *B. subtilis* strain PY79 by standard transformation techniques. This plasmid, based upon the *E. coli-B. thuringiensis* shuttle vector pHT3101 (36), contained the endogenous Cry5B promoter and 3'-untranslated region driving expression of the wild-type cry5B gene (29). To generate an empty vector control strain, empty vector pHT3101 was also transformed into PY79. The presence of the cry5B gene in the PY79-Cry5B strain and its absence from both the parent PY79 strain and the control strain (PY79-vector) were confirmed by PCR. PCR detection of the plasmid in the PY79-vector strain and its absence from the parent PY79 strain were also confirmed. PY79 was able to maintain both the cry5B plasmid and pHT3101 under standard antibiotic selection with erythromycin, indicating that the origin of replication for *B. thuringiensis* functioned in *B. subtilis*, as demonstrated previously (37).

The PY79-Cry5B and PY79-vector strains were sporulated. Robust expression of a protein of the size of Cry5B was detected by PAGE only in the PY79-Cry5B strain. Mass spectroscopy confirmed that the protein was indeed Cry5B. On the basis of quantitation relative to bovine serum albumin (BSA) standards on polyacrylamide gels, Cry5B was expressed at 10 mg/liter culture, which was ~7.5-fold lower than the Cry5B expression level in *B. thuringiensis* (75 mg/liter) (29). Two other bands common to both PY79-vector and PY79-Cry5B were identified by mass spectroscopy as the 60-kDa chaperonin protein and an oligopeptide-binding protein from *B. subtilis* 168, the parent strain of PY79 (38). These assays confirmed that Cry5B was expressed in the PY79-Cry5B strain and that the strain was *B. subtilis* PY79.

Crystal proteins expressed during sporulation of *B. thuringiensis* assemble into crystalline inclusions in the mother cell compartment that are often bipyramidal in shape (39). This assembling is also true of Cry5B produced in *B. thuringiensis* (40). Whereas no crystals were detected by SEM upon sporulation of the PY79-vector strain, many SEM-detectable small crystalline inclusions were present upon sporulation of the PY79-Cry5B strain. Some of these crystals were bipyramidal in shape; others appeared to be truncated versions of such crystals. Thus, Cry5B not only was expressed in PY79 but also assembled into crystalline inclusions.

Figure 11:
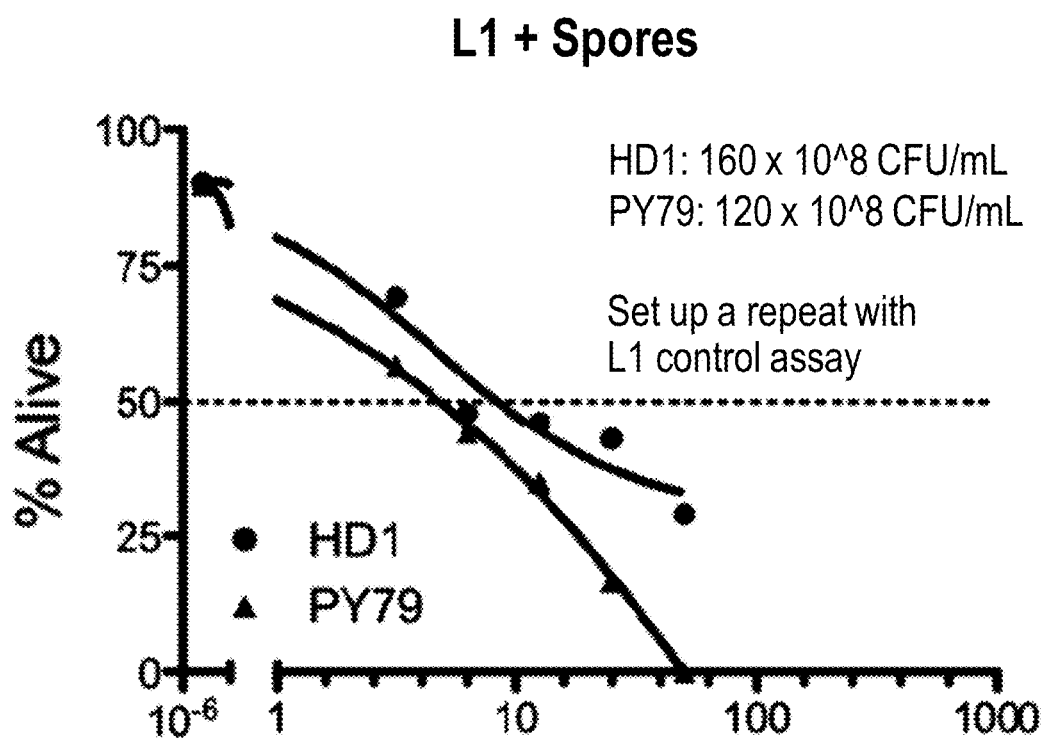

Cry5B made by PY79 was bioactive. To test whether or not Cry5B made by PY79 was bioactive, dose-dependent mortality assays were set up using the laboratory roundworm *C. elegans* in a standard 48-well format (13, 41). The Cry5B component of PY79-Cry5B spore crystal lysates was quantitated relative to BSA standards on polyacrylamide gels. Fourth-stage larvae were incubated for 6 days in wells containing PY79-Cry5B spore crystal lysates containing fixed amounts of Cry5B. Antibiotics were included to prevent infection of the roundworms by bacteria (42). Cry5B made by PY79 was found to kill *C. elegans*, with an LC50 of 4.3 µg/ml (95% confidence interval, 3.6 to 5.0 µg/ml) (FIG. 11). This LC50 was similar to the LC50 of Cry5B purified from *B. thuringiensis* (7 to 9 µg/ml) (35) under comparable conditions (25° C., 6 days). Conversely, *C. elegans* exposed to PY79-vector spore lysates (with a spore count equivalent to the highest dose used with PY79-Cry5B) was >99% viable (122/123 worms were alive). Thus, PY79 spore lysates were not lethal to *C. elegans*, and PY79 was able to produce bioactive Cry5B.

Figure 7A:
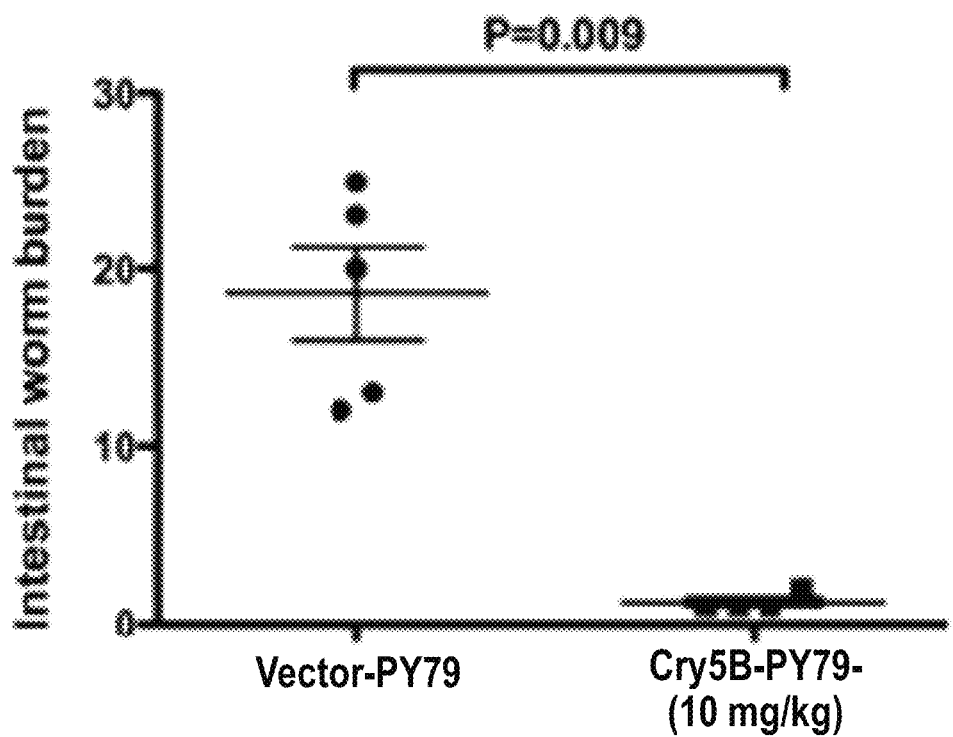
FIGS. 7A-C shows that PY79-Cry5B had a dose-dependent therapeutic effect against hookworm infection in hamsters.
Figure 7B:
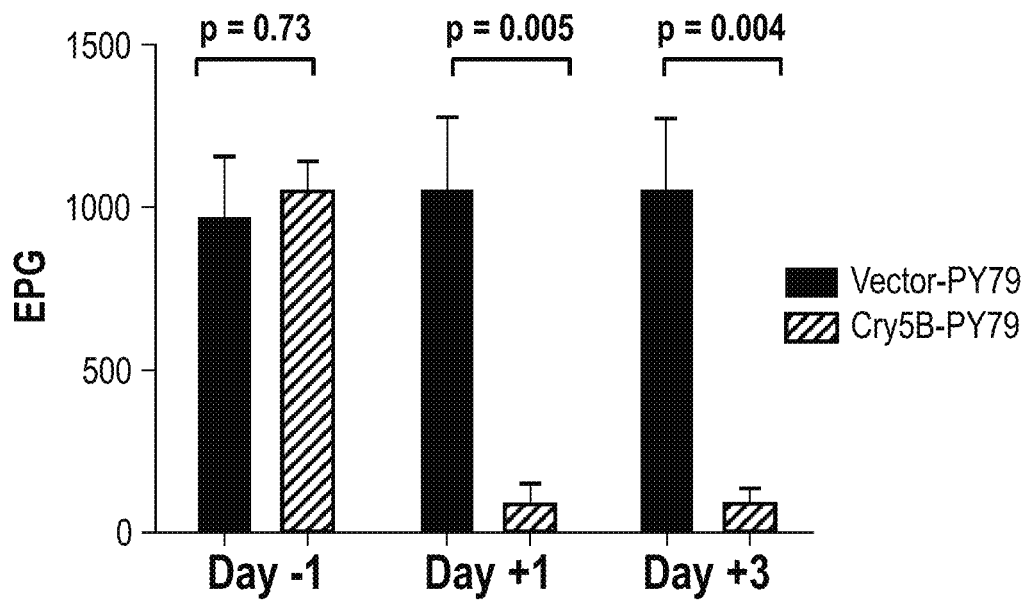
Figure 7C:
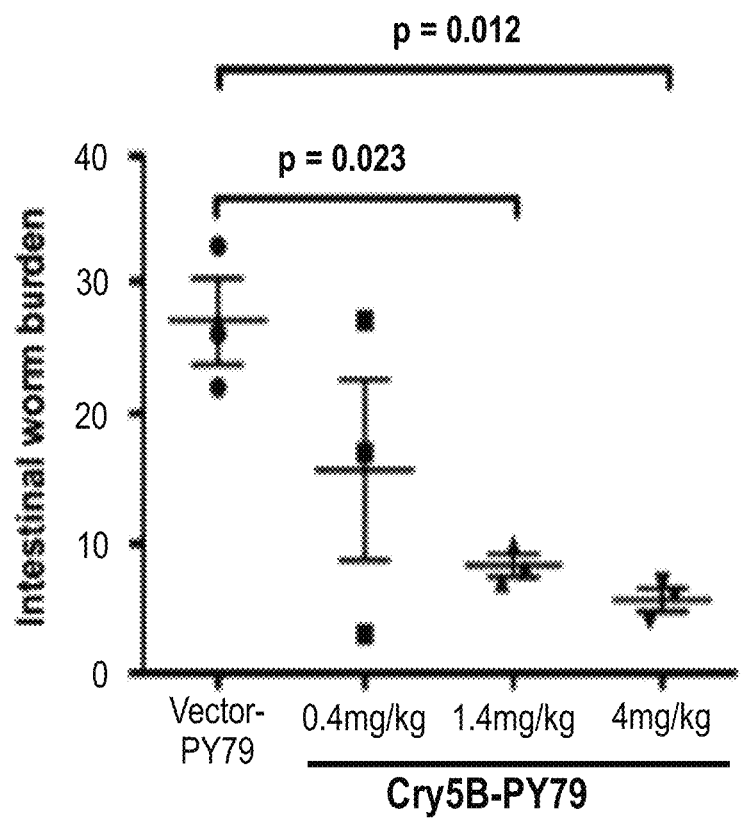

PY79-Cry5B was therapeutic against experimental hookworm infection in hamsters. Nine hamsters were infected with the hookworm parasite *A. ceylanicum*. At 18 days post-inoculation, five hamsters were treated per os with a single dose of PY9-vector spore lysate, and four were treated with a single dose of PY79-Cry5B spore crystal lysate (equivalent spore counts were used in both treatment groups; the amount of Cry5B was determined relative to BSA standards on protein gels). The single dose of Cry5B used was 10 mg/kg, chosen based on published doses of clinical anthelmintics used in the same model of hookworm disease (Table 3). Feces were collected before and after treatment in order to determine worm loading and changes to parasite egg output. At 22 days post-infection, animals were sacrificed and intestinal worm burdens determined. With a single dose, hookworm burdens were reduced 93% relative to those of the control group (P=0.009) (FIG. 7A). Strong effects could also be seen in the reduction of parasite eggs excreted into feces (91% reduction) (FIG. 7B). To determine if there was an effective dose-response relationship and if significant therapy could be provided at lower doses, another experiment was carried out with three hamsters per group and Cry5B doses of 0.4, 1.4, and 4 mg/kg. Significant clearance of parasites was seen at 1.4 and 4 mg/kg Cry5B in PY79 (69% and 79% reductions, with P values of 0.023 and 0.012, respectively) (FIG. 7C).

The experiments in this Example demonstrated for the first time that *Bacillus subtilis* can be engineered to provide a significant therapeutic effect against an existing parasitic disease. This pilot study employed PY79, a laboratory strain of *B. subtilis* that has been used as a model for the delivery of viable bacterial therapies in humans and livestock and that is closely related to a food-grade *B. subtilis* species. PY79 was made to express and correctly present the BtCry5B protein in a manner that was bioactive against the laboratory roundworm *C. elegans*. A single 10-mg/kg dose (71 nmol/kg) of Cry5B administered as a Cry5B-PY79 spore crystal lysate reduced *A. ceylanicum* hookworm burdens in hamsters by 93%, and a dose as small as 1.4 mg/kg was able to provide significant therapy. In previously published data, purified Cry5B delivered at 10 mg/kg reduced hookworm burdens by 65% (14); the data disclosed herein suggest that delivery of Cry5B via PY79 spore crystal lysates was superior to delivery via purified protein.

The expression of Cry5B in *B. subtilis* employed the endogenous Bt Cry5B promoter and may have been influenced at least partly by two putative sigma E elements upstream of the cry5B start codon. Sigma E is a sporulation-specific promoter that is active in *B. subtilis* and is also known to be involved in crystal protein production in *B. thuringiensis* (43, 44). The engineered strain used for the present study included antibiotic resistance genes associated with the cry5B plasmid. Given the genetic tools associated with *B. subtilis* (45), a Cry5B-expressing *B. subtilis* therapeutic product for humans is contemplated that includes the cry5B gene integrated into the genome and that lacks any antibiotic resistance genes The 93% elimination (P=0.0.009) of *A. ceylanicum* hookworm parasites from hamsters by use of a single 10-mg/kg (71 nmol/kg) dose compared favorably to the results of anthelmintics used clinically (Table 3). For example, a 10-mg/kg (49 µmol/kg) dose of levamisole resulted in a 60% reduction of *A. ceylanicum* burdens in hamsters, a 10-mg/kg (17 µmol/kg) dose of pyrantel resulted in an 87% reduction in *A. ceylanicum* burdens, a 10-mg/kg (22 µmol/kg) dose of tribendimidine resulted in a 75% reduction of *A. ceylanicum* burdens, and a 1.25-mg/kg (4.7 µmol/kg) dose of albendazole resulted in an 88% reduction of *A. ceylanicum* burdens (46, 47). In addition to high efficacy, Cry5B had a different mechanism of action from that of chemical anthelmintics; Cry5B has been shown to be a pore-forming protein that binds to invertebrate-specific glycolipids and attacks the plasma membrane of the nematode intestine (34, 35, 48-50).

As described herein PY79-Cry5B was comparable to many current drugs in its efficacy on a mg/kg basis, and on a molar level, it appeared to be superior (e.g., the molar dose of Cry5B used in the present experiments was 66 times lower than the molar dose of albendazole mentioned above). The present results validated the *B. subtilis*-Cry5B approach.

Also contemplated are increasing *B. subtilis*-Cry5B specific activity, e.g., by Cry5B point mutations that increase roundworm-killing activity (51) and by optimization of fermentation conditions that can also increase crystal protein specific activity (52). Given that *Bacillus* bacteria can be produced and stored cheaply and in large quantities (53), the present results demonstrated the feasibility of Cry5B delivery by food-grade *B. subtilis* for the treatment of STH diseases.

TABLE 3

Comparison of efficacies of PY79-Cry5B and clinically used anthelmintics against *A. ceylanicum* infections in hamsters

| Treatment[a] | Dose (_mol/kg) | % Parasite reduction | P value | Reference |
|---|---|---|---|---|
| Levamisole | 49 | 60 | 0.057 | 47 |
| Pyrantel | 17 | 87 | 0.057 | 47 |

TABLE 3-continued

Comparison of efficacies of PY79-Cry5B and clinically used anthelmintics against *A. ceylanicum* infections in hamsters

| Treatment[a] | Dose (_mol/kg) | % Parasite reduction | P value | Reference |
|---|---|---|---|---|
| Tribendimidine | 22 | 75 | >0.05? | 46 |
| Albendazole (1.25 mg/kg) | 4.7 | 88 | <0.001 | 47 |
| Cry5B | 0.071 | 93 | 0.009 | This Example |

[a]Treatments were administered at 10 mg/kg unless otherwise stated.

Example 9

Bioactivity of Compositions Comprising Cry5B and Bacteria

This example describes additional data that were obtained using the above-described bioassays for anthelmintic activity.

FIG. 8 shows results from an in vivo bioassay of intestinal worm burdens in golden Syrian hamsters infected with *Ancylostoma ceylanicum* hookworms as described by Hu et al. (2012 *PLoS Negl. Trop. Dis.* 6:e1900. doi:10.137/journal.pntd.0001900). The four groups (in black, n=7 per group) shown are the intestinal worm burdens from the groups of infected hamsters treated with purified full-length *B. thuringiensis* Cry5B protein (prepared according to Griffitts et al., 2001 *Science* 293:860; for sequence see FIG. 2) at a single dose of 1 mg (solid circles, 10 mg/kg), 3 mg (solid upright triangles, 30 mg/kg), or 10 mg (solid inverted triangles, 100 mg/kg) (715 nmoles/kg), or with placebo (solid squares, ddH$_2$O), respectively. The treatments were conducted on day 16 P.I. and intestinal worm burdens assessed on day 21 P.I. The worm burdens in each hamster are indicated with a separate symbol. Long horizontal bars represent mean worm burdens; smaller bars indicate SEM (standard error of the mean).

Figure 9:
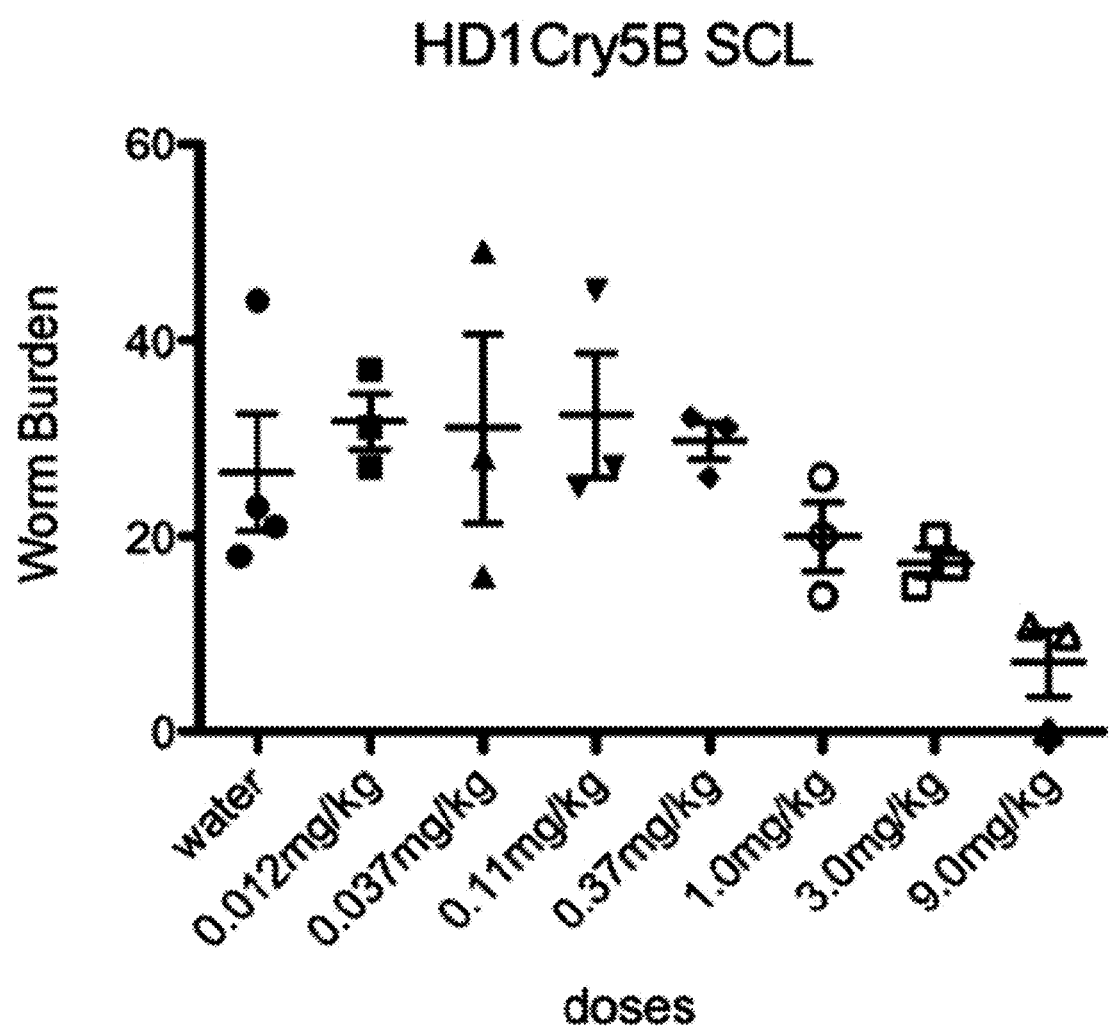

FIG. 9 shows dose-response results for indicated dosages of unfractionated Cry5B-containing spore-crystal lysates (SCL) in the in vivo bioassay of intestinal worm burdens in golden Syrian hamsters infected with *Ancylostoma ceylanicum* hookworms. The assay was performed according to Hu et al. (2012 PLoS Negl. Trop. Dis. 6:e1900. doi:10.137/journal.pntd.0001900) except instead of purified Cry5B protein the animals received the indicated dosages, via gavage, of Cry5B spore-crystal lysates obtained from cultured *Bacillus thuringiensis* cells that were transformed with a low copy plasmid that expressed *B. thuringiensis* Cry5B and then grown to sporulation phase. The amounts of Cry5B gavaged were determined by taking known volumes of spore crystal lysates, resolving full length Cry5B protein by SDS PAGE, and quantitating the amount of protein in the Cry5B band relative to known amounts of bovine serum albumin (BSA) standards on the gel.

Figure 10:
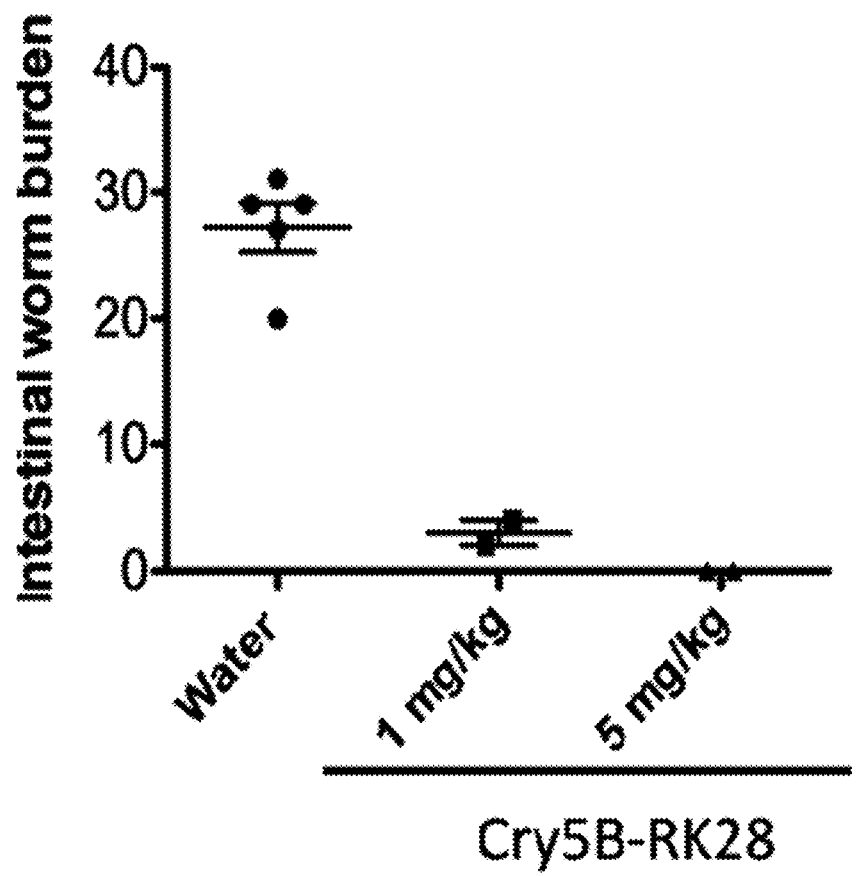

FIG. 10 shows results from the in vivo bioassay of intestinal worm burdens in golden Syrian hamsters infected with *Ancylostoma ceylanicum* hookworms (Hu et al., 2012 PLoS Negl. Trop. Dis. 6:e1900. doi:10.137/journal.pntd.0001900) following treatment with two different dosages of Cry5B spore-crystal lysates obtained from cultured *Bacillus thuringiensis natto* cells that were transformed with a low copy plasmid that expressed *B. thuringiensis* Cry5B and then grown to sporulation phase. *B. subtilis natto* was transformed with the same Cry5B expressing plasmid described in Example 14 (Hu et al. *Appl. Environ. Microbiol.* 2013, 79(18):5527). Because *B. subtilis natto* is not naturally competent, *B. subtilis natto* cells were made competent by artificially introducing the ComK competency plasmid into the *B. subtilis natto* strain via protoplast transformation (Ashikaga et al., *J Bacteriol.* 2000; 182(9):2411-5; Romero, D., et al *J Microbiol Meth.* 2006; 66(3):556-9). The resultant strain was able to take up any DNA and the ComK plasmid, being unstable, was readily lost by growing under non-selective pressure).

Figure 1A:
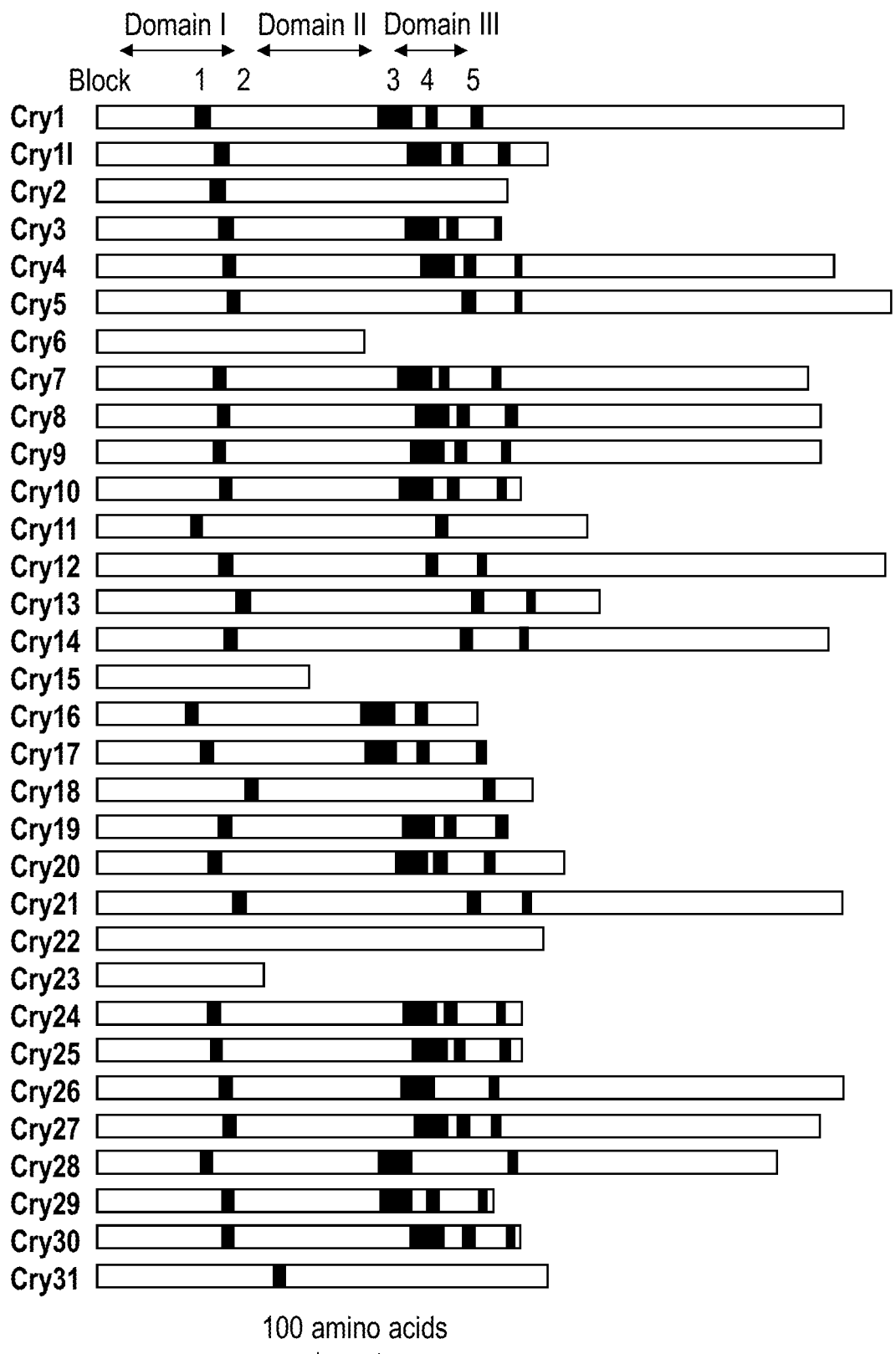
FIGS. 1A-B FIG. 1A depicts the positions of conserved blocks among certain Cry proteins. de Maagd, R. A., et al. "How *Bacillus thuringiensis* has evolved specific toxins to colonize the insect world." Trends in Genetics 17(4): 193-99, 195 (FIG. 2a) (April 2001).
Figure 1B:
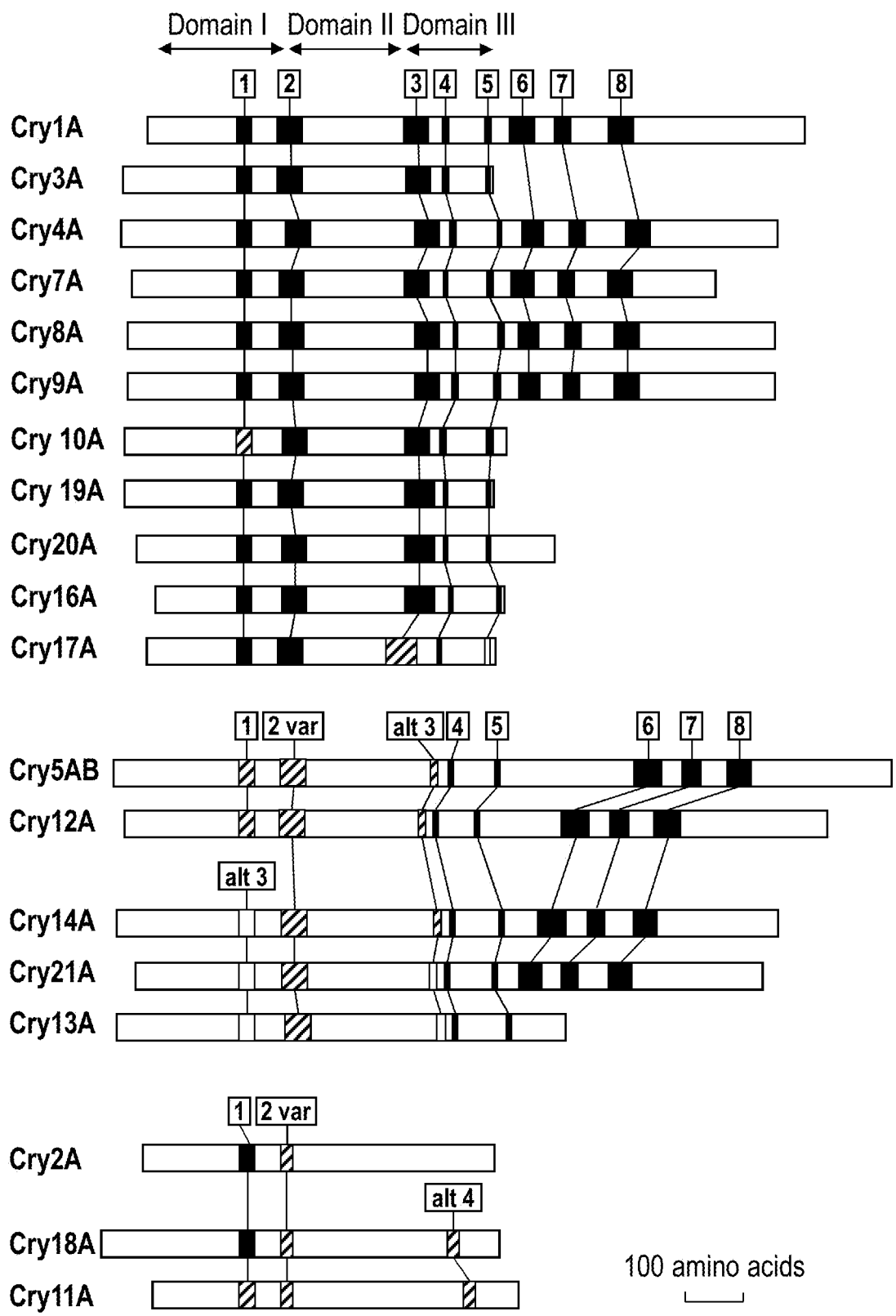
Figure 6:
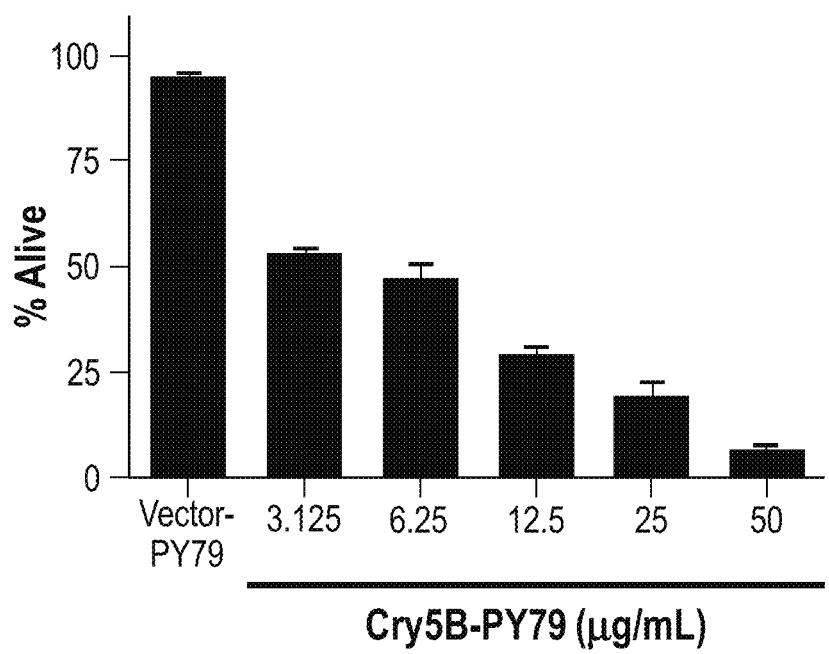
FIG. 6 depicts PY79-Cry5B bioactivity in vitro against *C. elegans*. The results shown are from dose-dependent mortality assays plotting % live *C. elegans* (y axis) versus Cry5B concentration (x axis). The PY79-vector strain (vector-PY79) lacked Cry5B (0 µg/ml). Each data point represents the average for three independent experiments with ~75 to 90 *C. elegans* organisms per experiment (~225 to 270 organisms per data point). Error bars represent standard errors.

FIG. 11 shows data obtained in vitro using the *C. elegans* mortality assay described in FIG. 6 to evaluate the effects on *C. elegans* of purified Cry5B protein (prepared according to Griffitts et al., 2001 *Science* 293:860; for sequence see FIG. 2) when combined in a mixture either with sporulated *B. thuringiensis* HD1 or with sporulated *B. subtilis* PY79. For each data point, the number of spores (HD1 or PY79) was held constant and the quantity of Cry5B was titrated (x-axis).

Figure 12:
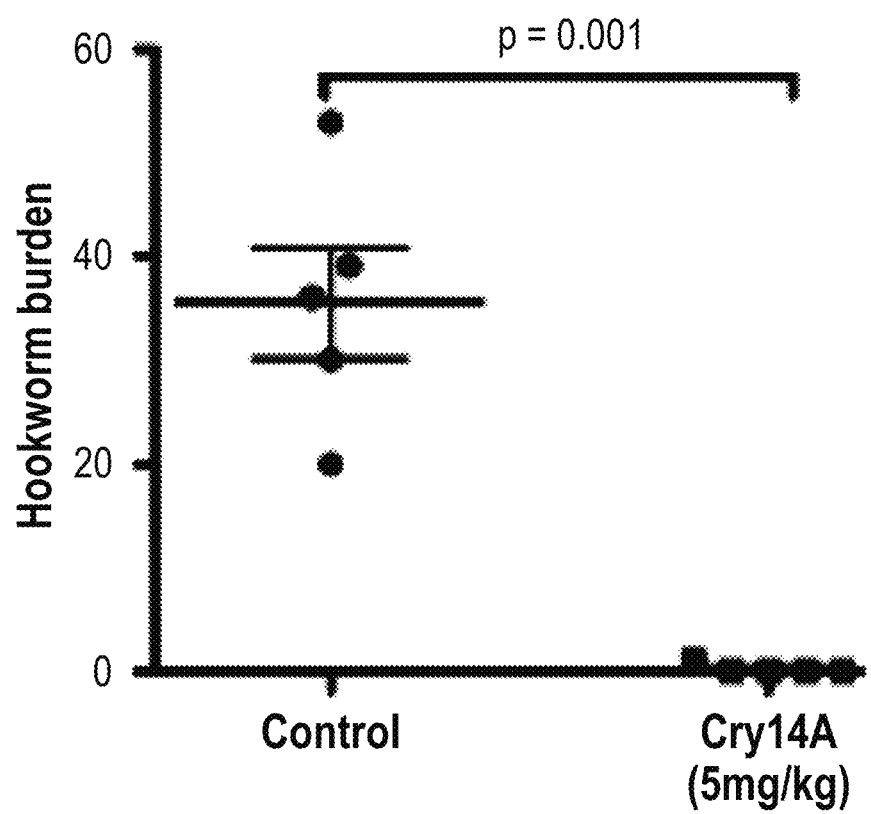
Figure 13:
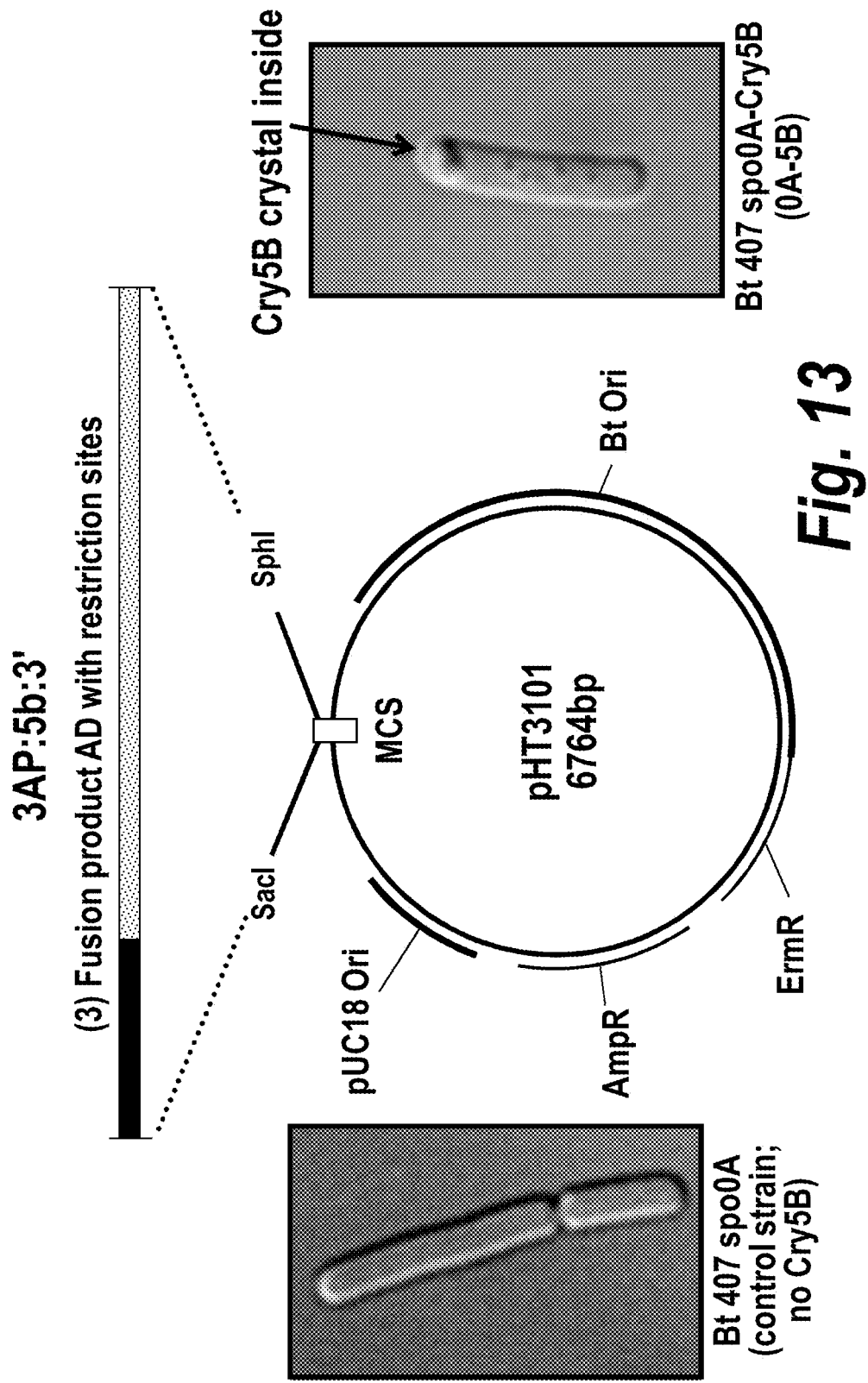
Figure 14:
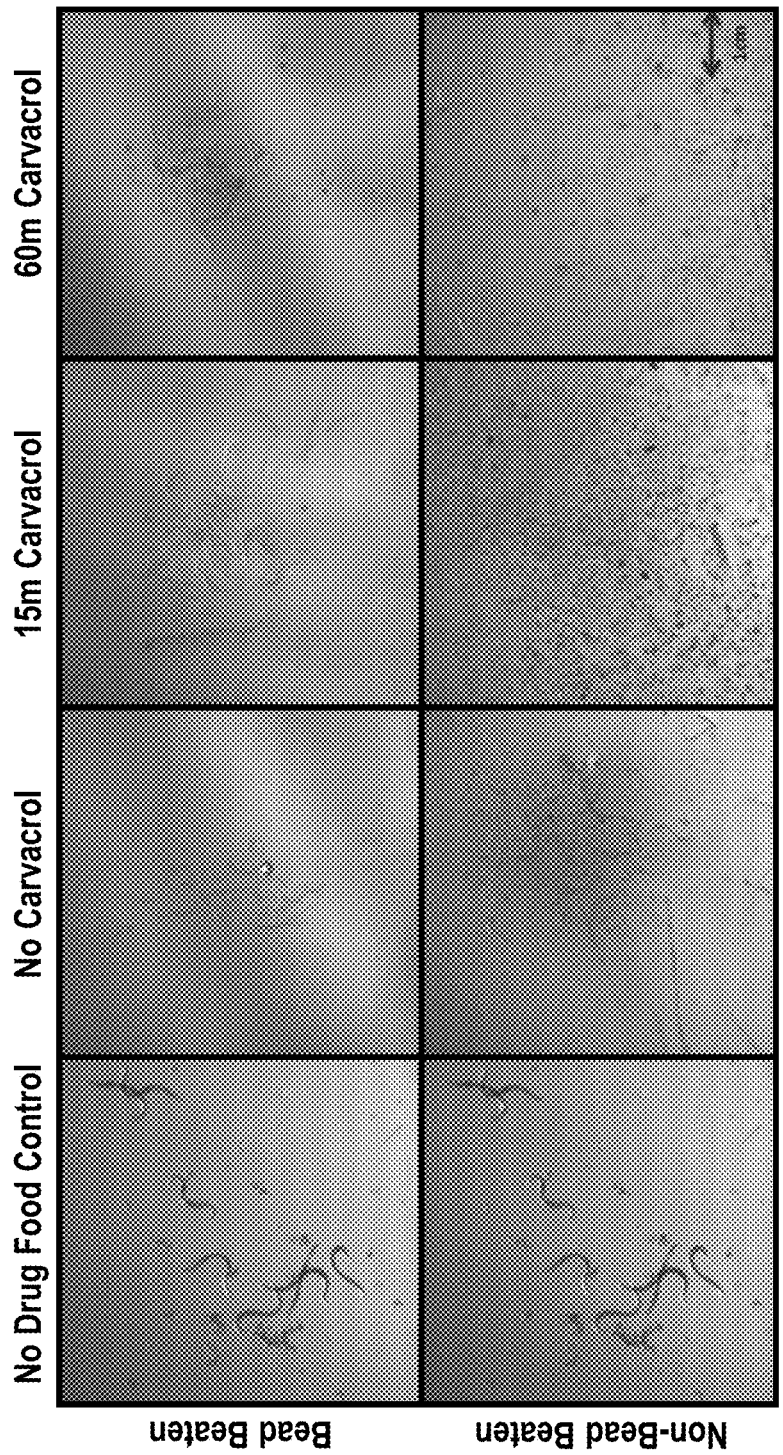

FIG. 12 shows results from the in vivo bioassay of intestinal worm burdens in golden Syrian hamsters infected with *Ancylostoma ceylanicum* hookworms (Hu et al., 2012 *PLoS Negl. Trop. Dis.* 6:e1900. doi:10.137/journal.pntd.0001900) following treatment (5 mg/kg) by gavage on day 18 P.I. with either *B. thuringiensis* strain HD1 spore lysates transformed with empty vector ("control", spore lysates from the acrystaliferous mutant *B. thuringiensis* strain HD1, which does not produce any Cry proteins) or spore crystal lysates from *B. thuringiensis* strain HD1 that has been engineered to express Cry14A (for sequence see FIG. 4) using a plasmid encoding Cry14A under the control of the operably linked Cry3A promoter. Hookworm burdens were assessed on day 20 post-infection (P.I.).

Example 10

Gene Replacement and Generation of a *Bacillus Subtilis* Auxotroph

Cry5B gene was integrated into the *B. subtilis* genome by a strategy that simultaneously deleted the chromosomal thyA gene, which encodes thymidylate synthetase. A cry5B cassette, flanked by the upstream and downstream regions of *B. subtilis* thyA, was assembled in vitro by standard PCR techniques. *B. subtilis natto* was transformed with this construct in a single step. Transformants simultaneously acquired two properties: auxotrophy for thymine nucleotides and the production of Cry5B protein. Because thymine auxotrophs in *B. subtilis* are known to be naturally resistant to trimethoprim and other antifolate compounds, selection for growth in the presence of trimethoprim plus thymine selected for the desired integration event without the introduction of an antibiotic resistance marker. The construct contained no foreign DNA at all except for the cry5B gene itself. The auxotroph permitted easy replication under laboratory conditions but the strain was environmentally dead and unable to replicate in the wild (e.g., following defecation by a human).

Example 11

Generation of a Cry5B-Expressing *B. Thuringiensis* Cell Effective in Treating Parasitic Worm/Helminth Infection Cry5B crystals are formed and trapped into a sporulation-deficient spo0A- *B. thuringiensis* cell when Cry5B is expressed under the control of a stationary phase promoter like Cry3A; such a bacterium was made using standard molecular biology techniques and used the construct depicted in the center panel of FIG. 13. The expression of the protein was good (FIG. 18C). The cells were treated with terpenes (carvacrol) for 15 or 60 minutes; the level and integrity of Cry5B crystals does not change with this treatment (FIG. 18C). Carvacrol teatment killed the recombinant cells (FIG. 18B). Based on *C. elegans* assays and in vivo hookworm curative studies in hamsters, the carvacrol treated and untreated cells were bioactive against nematodes (FIGS. 18-22).

Example 12

Production of Cry5B Spore Crystal Lysate and Purified Protein

Cry5B spore-crystal lysates (SCL) were produced by sporulation in PGSM medium as previously described (Cappello, M., et al. *Proc Nat Acad Sci.* 103, 15154-15159, 2006; Marroquin, L., et al. *Genetics.* 155, 1693-1699, 2000). The Cry5B promoter and gene were cloned into vector pHT3101 (Lereclus, D., et al. *FEMS Microbiol. Lett.* 60, 211-217, 1989) and transformed into Crystal protein minus (Cry−) *Bacillus thuringiensis* (Bt) subsp. *kurstaki* strain 4D8 (from the *Bacillus* Genetics Stock Center) using standard protocols. When required, Cry5B protein was purified from SCL using published protocols (Griffitts, J., et al. *Science.* 293, 860-864, 2001).

Example 13

Production of BaCC (*Bacillus* with Cytosolic Crystal) and IBaCC (Inactivated *Bacillus* with Cytosolic Crystal)

BaCC

For production of Cry5B in sporulation defective cells, Bt strain 407 lacking the master spo0A regulator of sporulation (Lereclus, D., et al. *Nat. Biotechnol.* 13, 67-71, 1995) was transformed using electroporation with Cry5B cloned into the pHT3101 vector under control of the Cry3A promoter (Agaisse and Lereclus, *J. Bacteriol.* 176, 4734-4741, 1994; Agaisse and Lereclus, *Mol. Microbiol.* 13, 97-107, 1994) to create the Bt-spo0A- Cry5B strain. This composition is further referred to as Cry5B-BaCC (*Bacillus* with Cytosolic Crystal).

IBaCC

*B. thuringiensis* 407 strains were propagated aerobically in 200 mL volume in 2 liter baffled flasks with shaking at 30° C. in three-fold concentrated Luria-Bertani broth (LB) supplemented with 10 μg/mL erythromycin and 200 μg/mL kanamycin for 48 hours. The *B. thuringiensis* cells were spun down at 4500 rpm for one hour at 4° C. and resuspended to ¼ of the original cell culture volume with prechilled sterile double-distilled water, and then were treated with 1 mg/mL carvacrol for 15 min with shaking at 4° C. The carvacrol treated cells were spun down and washed three times with prechilled sterile double-distilled water. Final pellets were concentrated 40 times and were stored at −80° C. until use. A diagram showing the IBaCC process is shown in FIG. 18A.

Freeze Drying

Samples were frozen at −80 C and then put into a FreeZone 1 Liter Benchtop Freeze Dry System (Labconco catalog number 7740020). The condenser was set to −60° C. and the vacuum at 22 mTor. The samples were freeze-dried overnight.

Spray-Drying

For spray-dried IBaCC, a 400 mL IBaCC sample at 10% solids w/v is spray dried using a Yamato Pulvis GB22 (or any other spray drying system) through a 100 micron atomizer nozzle at 5 mLs/min with atomizing air set at 1 Kgf/m$^2$, drying air set at 0.21 m$^3$/min, inlet/outlet temperatures set at 98° C./59° C., respectively.

Example 14

Terpene Mediated Inactivation of BaCC

Minimum Inhibitory Concentration

Three terpenes were tested against BaCC including: carvacrol, geraniol and farnesol, by using the broth microdilution method as described in Agaisse and Lereclus, *J. Bacteriol,* 176, 4734-4741, 1994 and Agaisse and Lereclus, *Mol. Microbiol.* 13, 97-107, 1994 with some modifications. Briefly, BaCC from a single colony was grown in 5 mL of LB medium supplemented with 10 μg/mL erythromycin+200 μg/mL kanamycin overnight (O.D. (600) of 4.8, 2.3×$10^7$ CFU/mL). Terpene solutions were prepared at 1 mg/mL in LB. One hundred μL of two-fold serial dilutions of each terpene in LB were prepared in 96-well microtiter plates over the range of 1000 to 3.9 μg/mL in triplicate. LB without terpenes was used as a negative control. BaCC culture was diluted 100 times, and 100 μL of BaCC culture was added to the wells. Absorbance at 600 nm was recorded before and after the incubation to monitor bacterial growth. The MICs were determined after incubation for 24 h at 30° C. without shaking. The minimum terpene concentration resulted in no absorbance increase overnight reported as minimum inhibitory concentration (MIC).

Time to Kill

In order to determine which terpene kills BaCC in the shortest amount of time, we incubated 5 mL of BaCC culture with three terpenes at 1 mg/mL at 4° C. for 1, 2, 3 and 5 hours. No terpene control and no bacteria controls were carried out simultaneously. After incubation with terpenes, samples were centrifuged and the pellets were washed with 5 mL of 1M NaCl once and 5 mL of sterile distilled water twice in order to remove the terpenes. The pellets were re-suspended in the original volume and plated on LB agar with kanamycin and erythromycin. Plates were incubated overnight at 30° C.; the next day, the number of colonies on the plates were enumerated and colony forming units (CFU)/mL calculated.

To assess terpene killing at shorter time points, BaCC culture was grown in 3×LB for 48 h as described above and 60 ml of cultures were aliquoted in sterile tubes. Carvacrol and geraniol were added to the final concentration of 1 mg/mL, and the tubes were placed on a rotator at 4° C. for 15 minutes. The negative control was prepared using sterile water instead of terpenes. At the end of the incubation period, the tubes were centrifuged at 2000×g for 10 minutes and pellets washed with 60 ml of 1 M NaCl once and washed with 60 mL of sterile distilled water twice. Pellets were re-suspended in 1.2 mL of sterile distilled water to concentrate the culture 50 times. Concentrated terpene treated and control samples were plated on LB agar plates containing kanamycin and erythromycin and incubated overnight at 30° C. The number of colonies were counted the next day and CFU/mL calculated for each time point.

All 3 terpenes had antimicrobial activity but carvacrol was the most efficient, killing the quickest and at the lowest concentration as depicted in Table 4 below.

TABLE 4

| | Terpene treatments of Bt | | | | | |
|---|---|---|---|---|---|---|
| | CFU/ml (1 mg/mL terpene treatment for time indicated) | | | | | MIC ug/mL |
| Samples | 0 | 15 min | 1 h | 3 h | 5 h | (100) |
| No Bacteria control | 0 | | 0 | 0 | 0 | |
| Bt control (no terpene) | 2.31 × $10^7$ | | 1.50 × $10^7$ | 1.00 × $10^7$ | 1.60 × $10^7$ | |
| Carvacrol | 2.31 × $10^7$ | | 0 | 0 | 0 | 125 |
| Farnesol | 2.31 × $10^7$ | | 1.00 × $10^7$ | 1.3 × $10^5$ | 0 | 500 |
| Geraniol | 2.31 × $10^7$ | | 0 | 0 | 0 | 500 |
| Bt control (no terpene; 50× conc.) | | 9.27 × $10^8$ | | | | |
| Carvacrol (50× conc.) | | 0 | | | | |
| Geraniol (50× conc.) | | 100 | | | | |

Terpene Washing Protocol

To reduce carvacrol residue in the final product, we tested different strategies. In order to reduce the carvacrol residue in the final IBaCC product, first the total amount of carvacrol was reduced by concentrating the cultures before carvacrol treatment. The cultures were centrifuged, and the pellets were re-suspended in sterile distilled water in half or one fourth of the original culture volume. Then, carvacrol was added at 1 mg/mL concentration. Second, carvacrol was removed from the culture by increasing the solubility of carvacrol in the water phase. Carvacrol is a lipophilic compound with a log P octanol/water of 3.64; therefore, it is held in the cell pellet more than the aqueous phase. As such, 5% and 15% of ethanol water was used in the washing steps following the IBaCC incubation with carvacrol. Another strategy employed was to increase the volume of distilled water during the washing steps to remove more carvacrol per wash step (for instance, only 25 mg carvacrol can be solubilized with 20 mL of water while 50 mg carvacrol can be solubilized with 40 mL of water.) Lastly, since the temperature affects carvacrol solubility, the incubation and washing steps were carried out at room temperature instead of 4° C. The positive control sample was treated with 1 mg/mL carvacrol without concentrating the culture prior to carvacrol treatment, incubated at 4° C., washed with 1M NaCl once and distilled water twice using 1:1 culture to wash volume ratio. No terpene control sample received water instead of carvacrol, but the incubation and washing steps were carried out in the same manner as the positive control. BaCC culture was grown in 3×LB for 48 hours, and 40 mL of BaCC culture was used for each condition. After washes, the culture was concentrated 20 times. Samples were plated for CFU/mL analysis as described earlier, and carvacrol residue was assessed by HPLC as follows.

IBaCC concentrates and no carvacrol control BaCC were diluted 1:10 in methanol and incubated one hour on a rotator in order to extract carvacrol. Then, the tubes were centrifuged and the supernatants were collected for HPLC analysis. Carvacrol standards ranging from 0-1000 μg/mL were prepared in 90% methanol-water. IBaCC, control and carvacrol standards were analyzed using RP-HPLC. The HPLC instrument consisting of a Beckman System Gold consisting of a 126 NMP Solvent Module, a 168 NM photodiode array detector and a 508 autosampler with Beckman System Gold 32 Karat 7.0 Data System software. Analysis was carried out using the stationary phase of a C18 column (μBondapak, Waters, 3.9 mm×300 mm, 10 μm) and the mobile phase of acetonitrile:water (70:30) in isocratic mode at 1 mL/min; the injection volume of 10 μL and the detection wavelength were set at 210 nm. The carvacrol concentration of each sample was determined from the corresponding peak area of the carvacrol standard curve.

TABLE 5

Effects of varying carvacrol wash protocols

| Condition | Number of alive bacteria in 1 ml culture | Number of alive bacteria in 1 ml 20X concentrate | Carvacrol residue in the 20X concentrate after washes (ug/ml) |
|---|---|---|---|
| Concentrated 2X = 20 ml before adding carvacrol | 0 | 0 | 78.66 |
| Concentrated 4X = 10 ml before adding carvacrol | 0 | 0 | 11.29 |
| Washes were done with 5% ethanol in water | 0 | 0 | 91.03 |
| Washes were done with 15% ethanol in water | 8 | 160 | 57.75 |
| Wash volume increased 2X (e.g., 40 ml wash for 20 ml culture) | 7 | 140 | 27.78 |
| Incubated and washed at room temperature | 0 | 0 | 16.48 |
| Control: 4C, no concentration, 1:1 culture to wash volume | 0 | 0 | 52.10 |
| no carvacrol control | $1.80 \times 10^8$ | $3.60 \times 10^9$ | 0 |

Example 15

Irradiation Mediated Inactivation of Bt

Figure 16A:
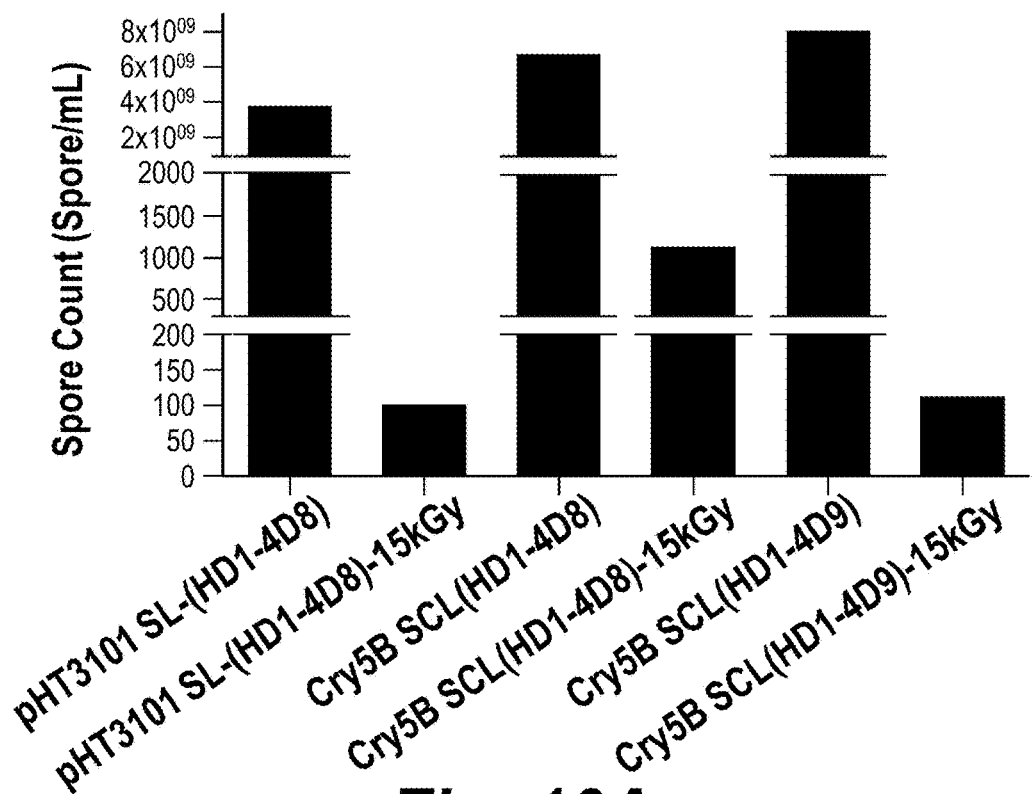
Figure 16B:
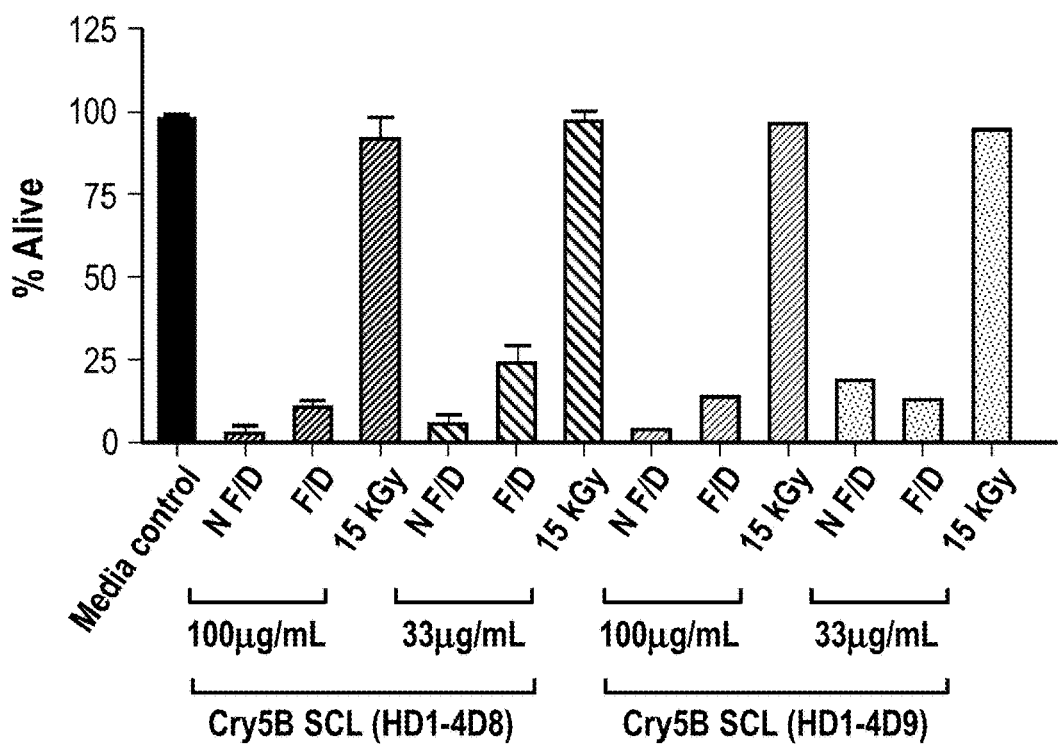

Gamma irradiation was carried out with a cobalt using freeze-dried Cry5B. A dose of 15 kGy was tested on SCLs of three different Bt strains expressing Cry5B or vector control. FIG. 16 A-B shows that this dose of gamma irradiation did not effectively completely kill the Bt strains nor did the strains retain full Cry5B bioactivity (no detectable bioactivity was seen). Further testing at doses ranging from 5-60 kGy did not significantly improve the results.

Example 16

Cry5B Spore Crystal Lysate Treatment In Vivo

Figure 15A:
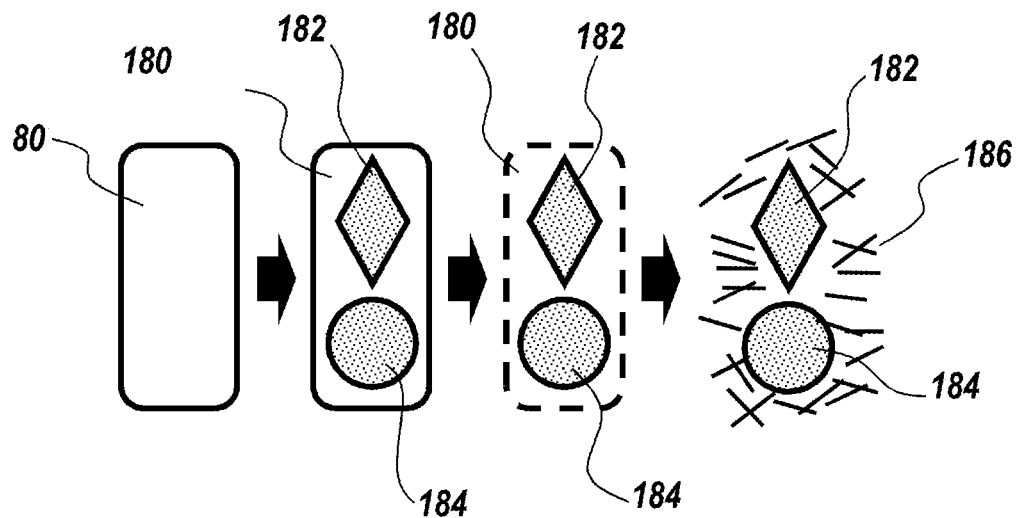

The normal life cycle of Bacillus thuringiensis (Bt) is such that when it runs out of nutrients, it enters the sporulation cycle during which time it produces insecticidal/nematicidal crystal (Cry) proteins packaged in a crystal. When the mother cell lyses upon completion of sporulation, the crystal and spore are released, along with bacterial lysate, giving rise to spore-crystal lysate (SCL), shown in FIG. 15A. A mother cell 180, enters the sporulation cycle, and produces a crystal protein 182 and a spore 184. Later during sporulation, mother cell 180 breaks down, releasing spore 184, protein crystal 182, and lysate 186.

Figure 15B:
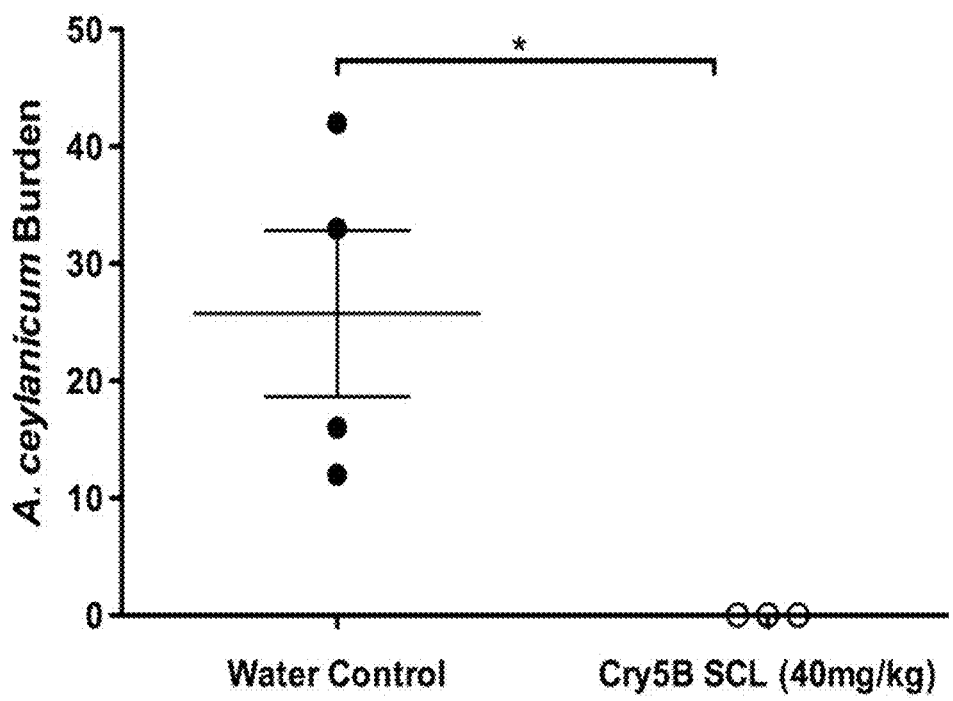
Figure 15C:
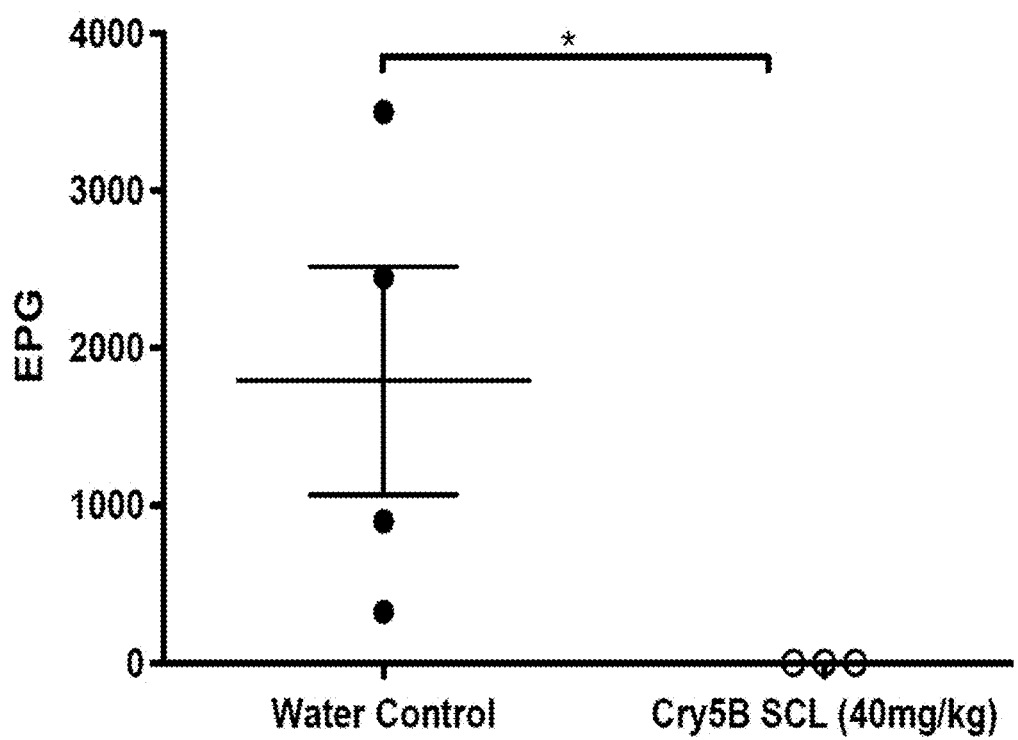

It was previously discovered that Bacillus thuringiensis (Bt) spore crystal lysates (SCLs) are highly effective against Heligmosomoides polygyrus bakeri infections in vivo (Hu, Y., et al. Proc Natl Acad Sci. 107, 5955-5960, 2010). Furthermore, a single 40 mg/kg dose cures Ancylostoma ceylanicum hookworm infections in hamsters, shown in FIGS. 15B and 15C. This activity is clearly superior to that of purified Cry5B protein (Hu, Y., et al. PLoS Negl. Trop. Dis. 6, e1900, 2012). One advantage of Bt over other bacteria that can be engineered to make Cry protein [e.g., Bacillus subtilis, (Hu, Y., et al. Appl. Environ. Microbiol. 79, 5527-5532, 2013)] is that crystal yields are much higher in Bt and batch-to-batch reproducibly is superior. This may be due to the fact that Bt is the natural host for Cry protein production and is naturally evolved to produce these proteins at high levels.

Example 17

BaCC Treatment In Vivo

Figure 17A:
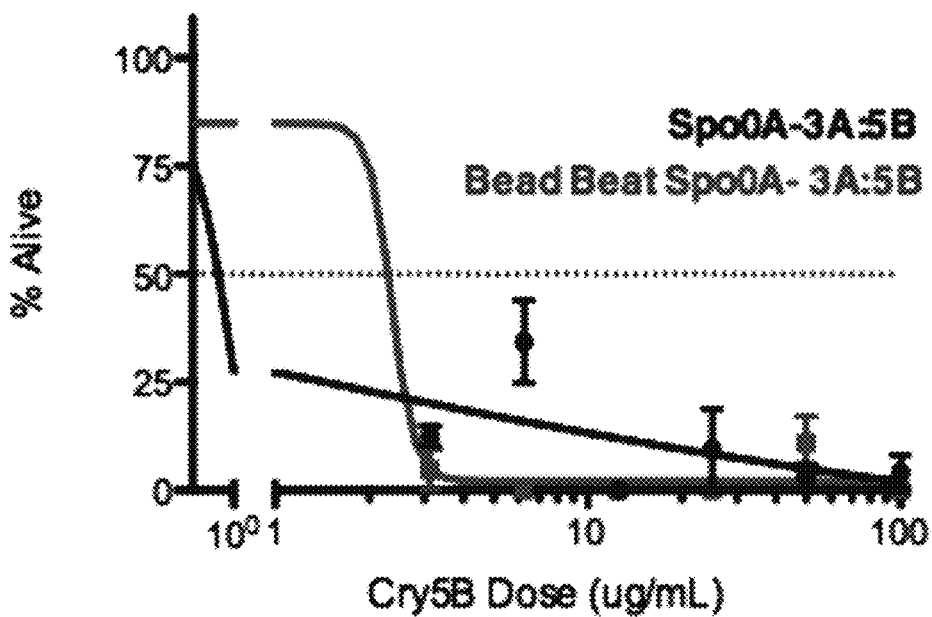
Figure 17B:
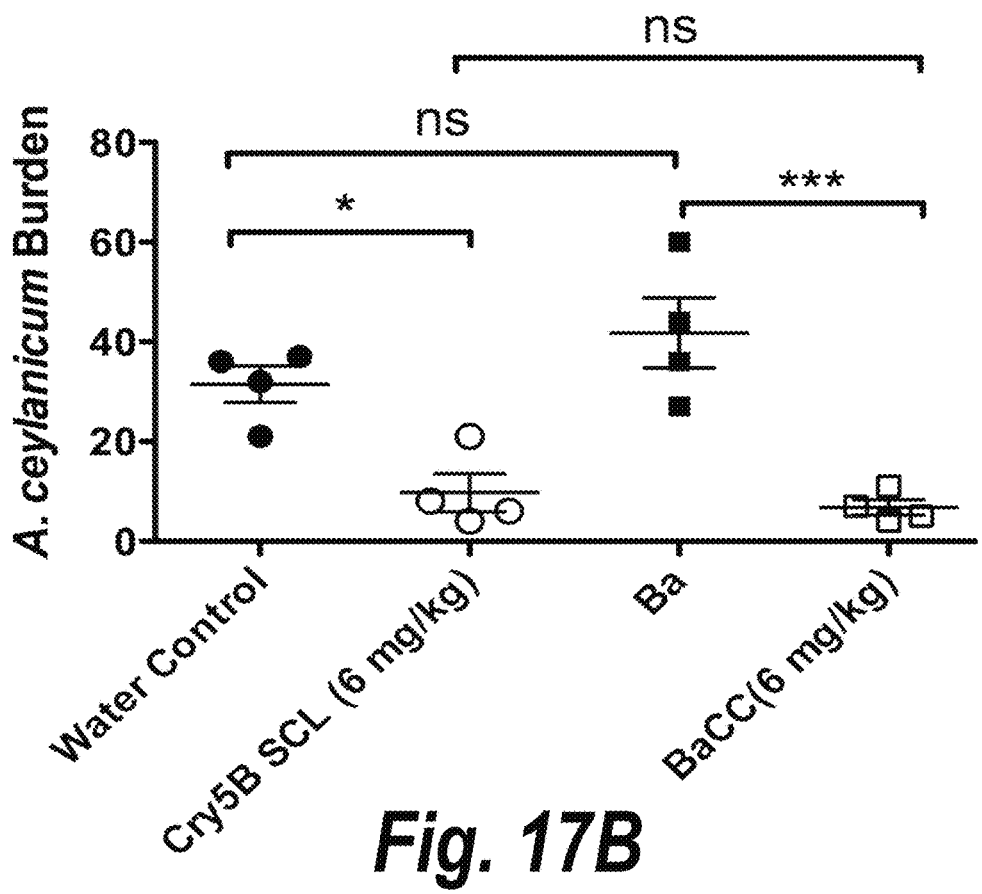
Figure 17C:
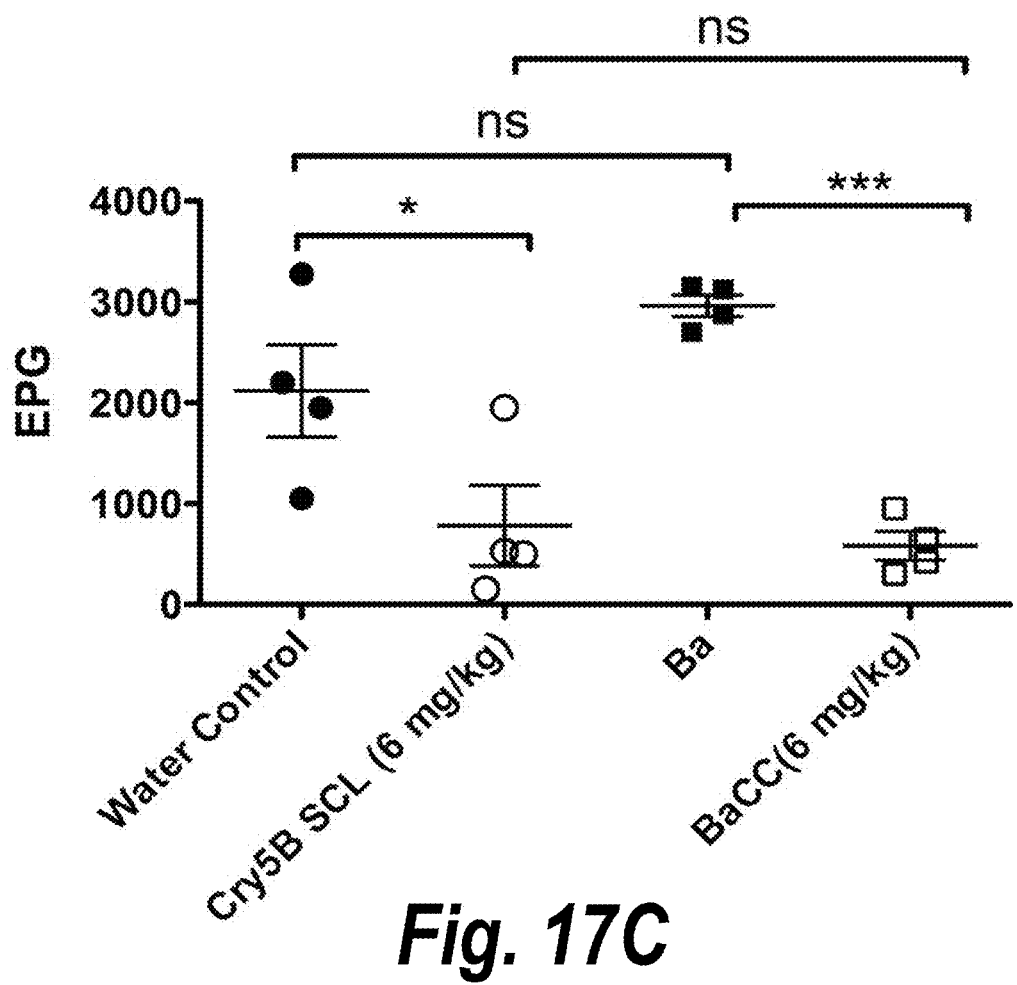
Figure 17D:
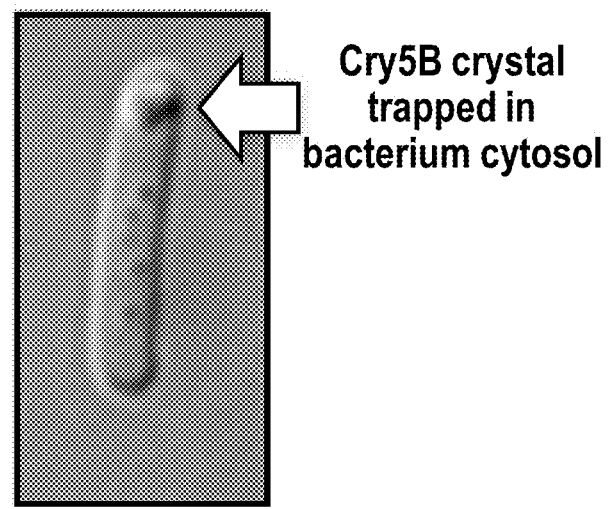

Although Bacillus spores are difficult to kill, vegetative Bacilli are relatively easy to kill. Since Bt Cry proteins can be produced in non-sporulating Bt under a stationary-phase promoter (Agaisse and Lereclus, J. Bacteriol. 176, 4734-4741, 1994; Agaisse and Lereclus, Mol. Microbiol. 13, 97-107, 1994), such Bt cells might be much easier to kill in a manner that would retain Cry5B bioactivity. Cry5B was cloned under the control of the Cry3A stationary-phase promoter and transformed the construct into sporulation-defective (spo0A-) Bt cells (Agaisse and Lereclus, J. Bacteriol. 176, 4734-4741, 1994; Agaisse and Lereclus, Mol. Microbiol. 13, 97-107, 1994). These cells, which do not sporulate, produce Cry5B crystals trapped in the cytosol. Cry5B produced in these cells is intoxicating to the laboratory nematode Caenorhabditis elegans, shown in FIG. 17A and it is bioactive against A. ceylanicum hookworm infections in vivo, shown in FIG. 17B-C. Such cells are termed BaCC for Bacillus with Cytosolic Crystal.

Example 18

IBaCC Treatment In Vivo

Figure 18A:
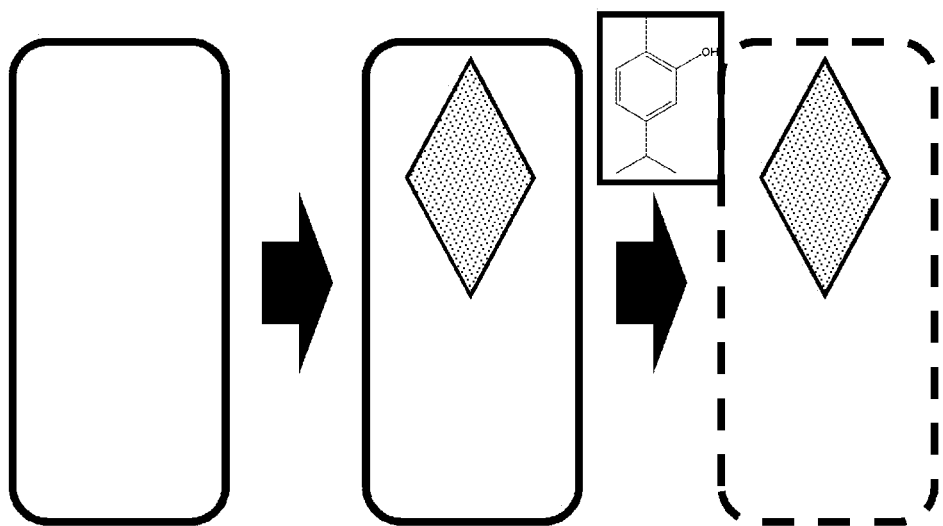
Figure 18B:
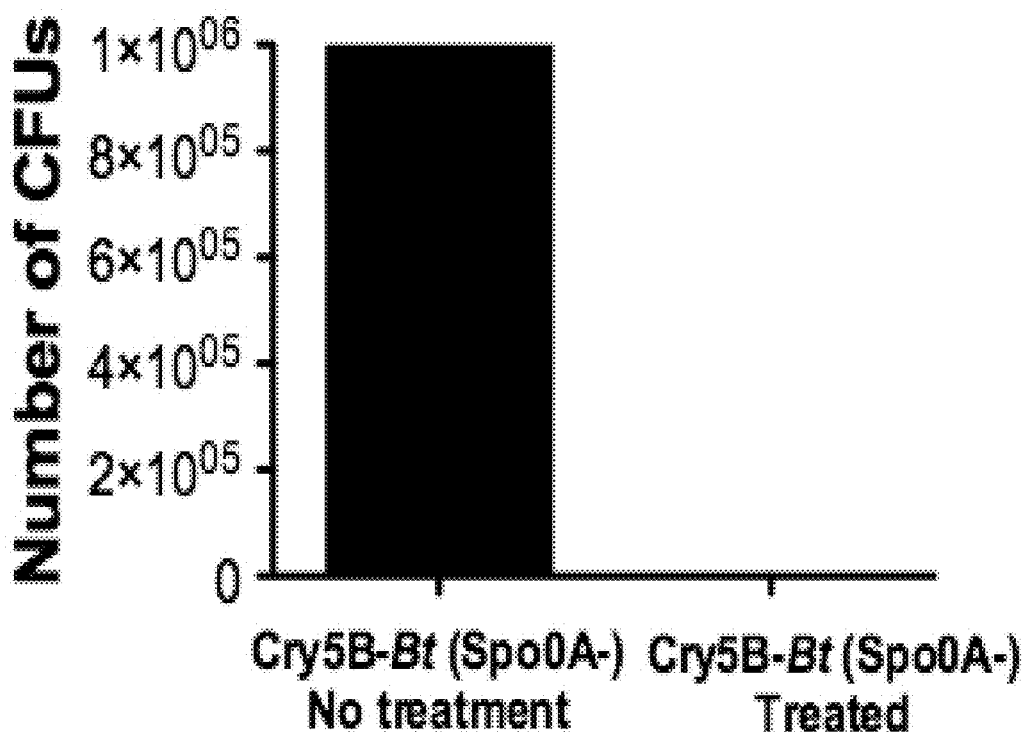
Figure 18C:
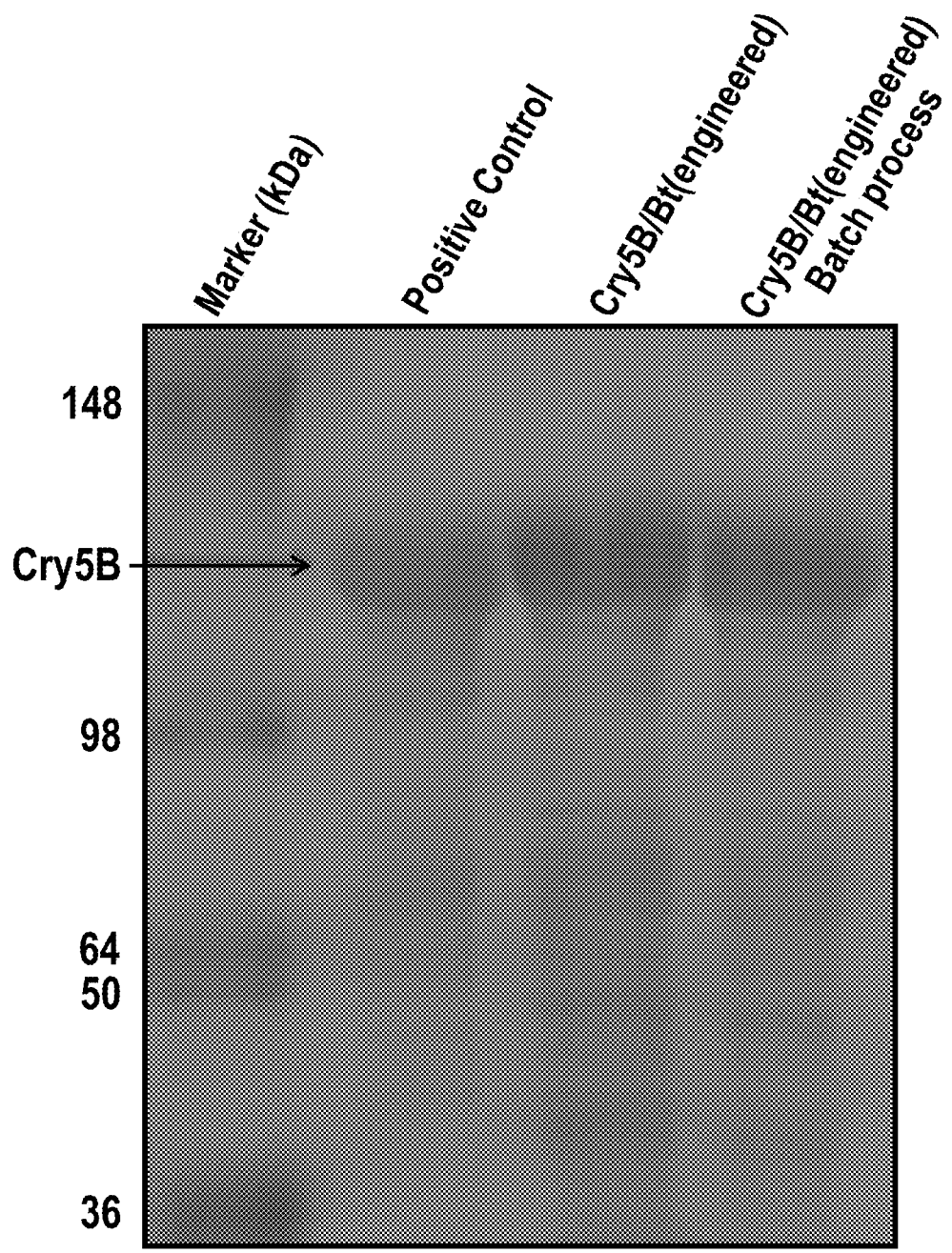
Figure 18D:
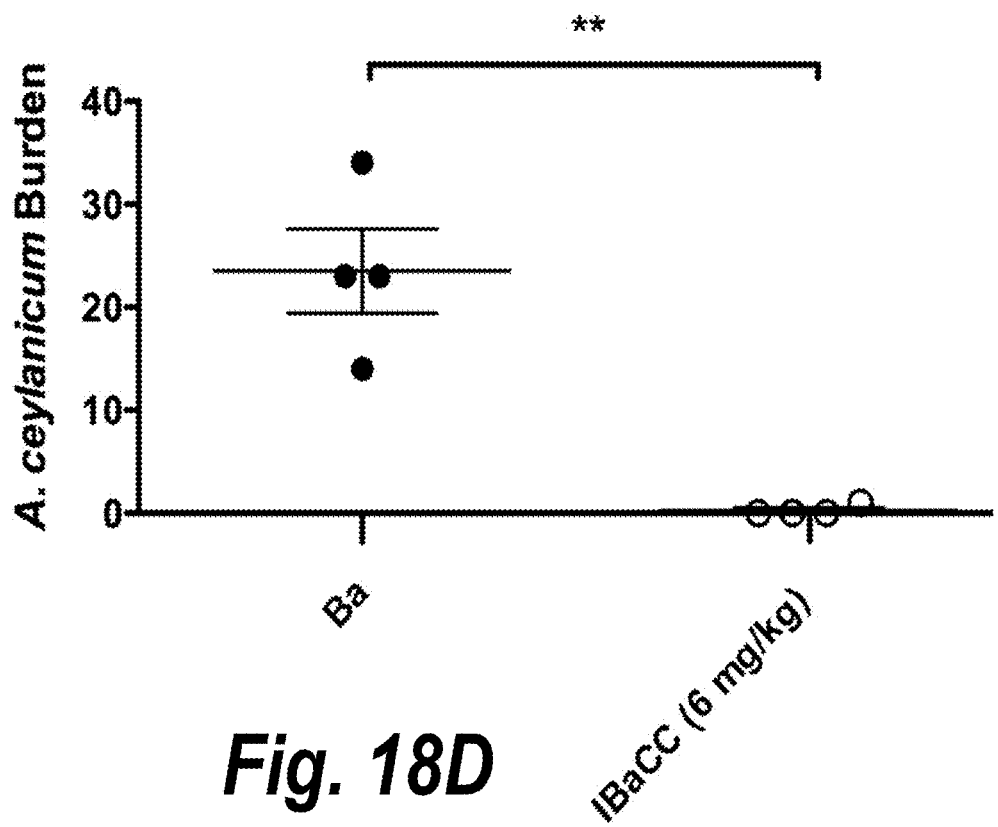
Figure 18E:
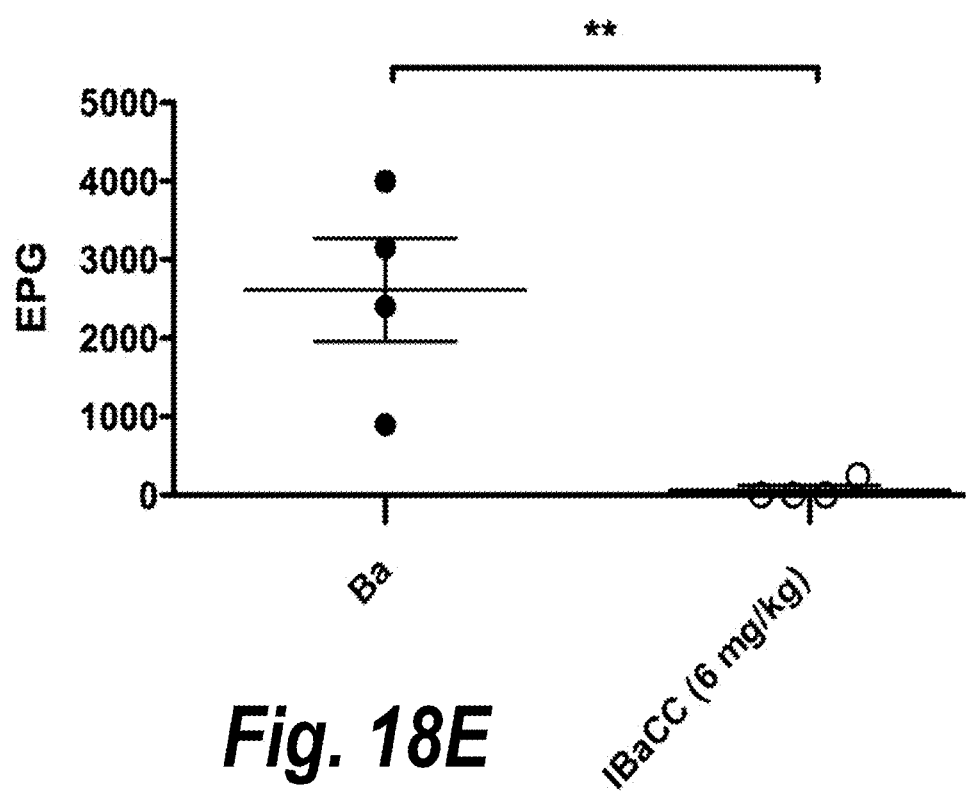
Figure 18F:
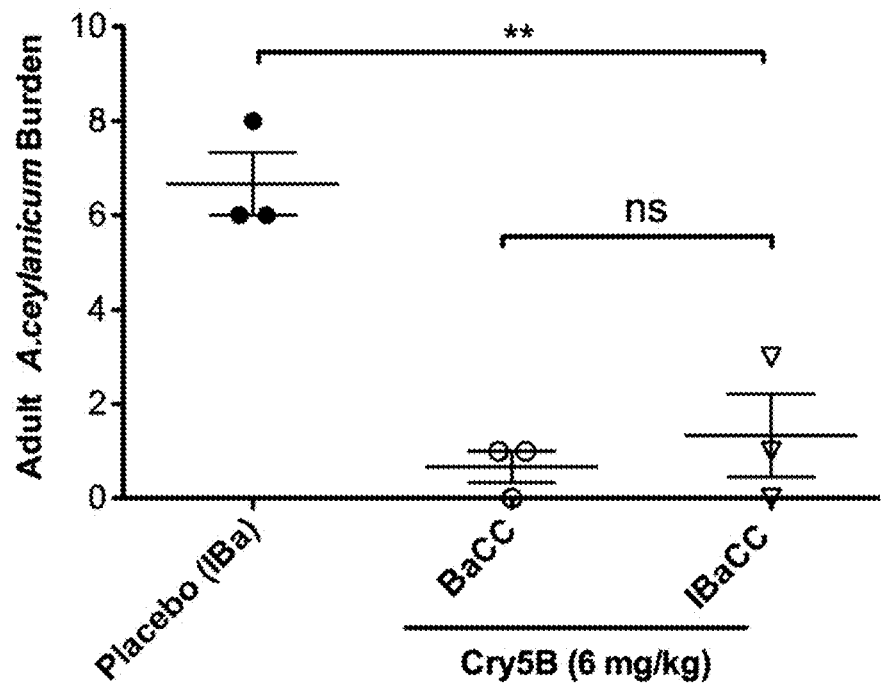
Figure 18G:
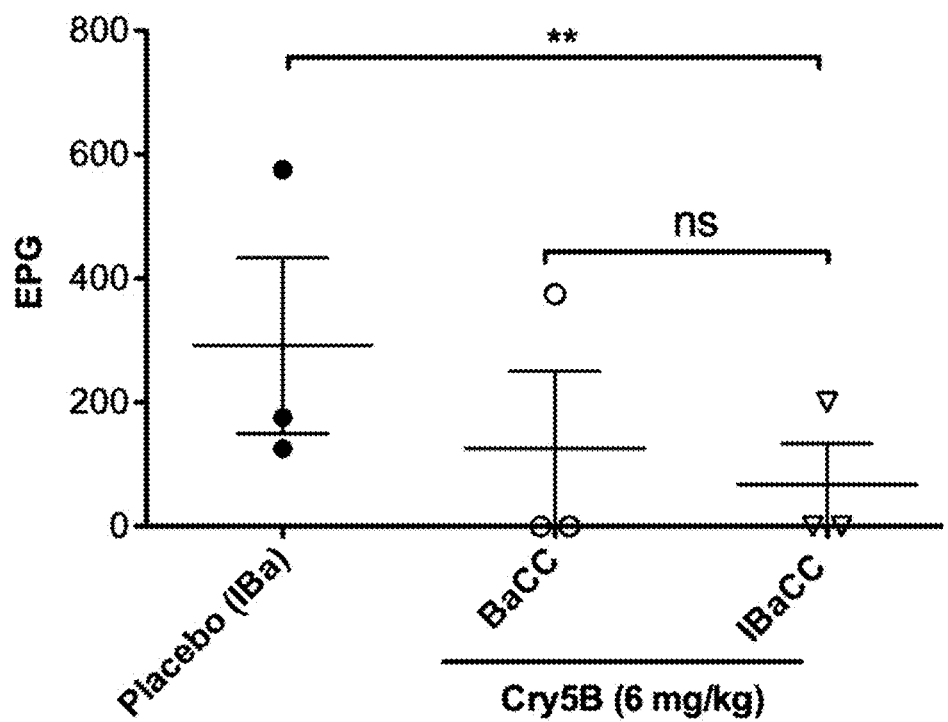

Carvacrol treatment of BaCC (spo0A- cells expressing Cry5B) cells resulted in complete killing of the Bacilli, shown in FIG. 18B while Cry5B protein as viewed on polyacrylamide gels looked normal, shown in FIG. 18C. Killed BaCC was still active against C. elegans and against A. ceylanicum hookworm infections in hamsters, shown in FIG. 18D-E. Killed BaCC was equally potent as live BaCC against hookworm infections in vivo, shown in FIGS. 18F-G. The dead BaCC containing biologically active Cry5B crystals are termed IBaCC for Inactivated Bacillus with Cytosolic Crystal.

Example 19

Neutralization of Stomach Acid Prior to BaCC or IBaCC Treatment In Vivo

Figure 17E:
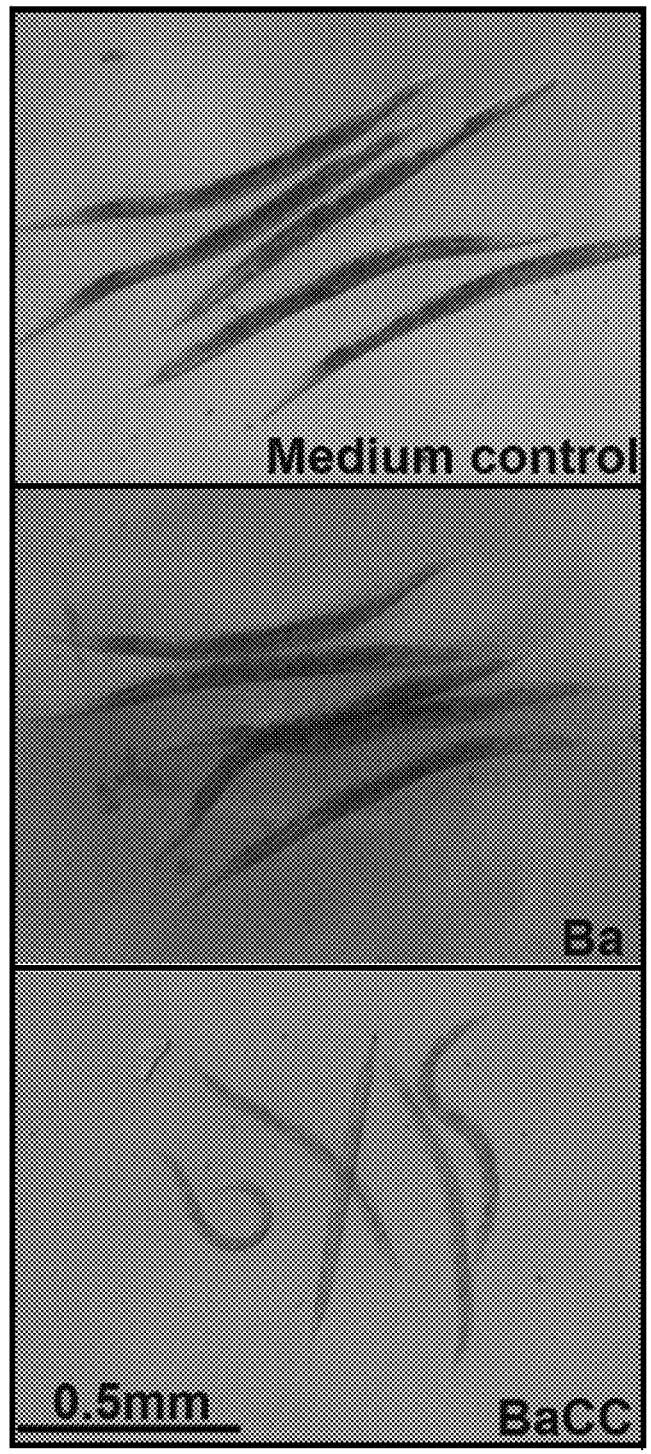

Since it was not possible to successfully encapsulate Cry5B to protect it from stomach acid for rodent delivery, neutralization of stomach acid was tested to improve Cry5B efficacy. Hamsters were infected with A. ceylanicum hookworms and either neutralized stomach acid or not by pregavaging with sodium bicarbonate (NaHCO$_3$) and cimetidine, and then treated the infected animals with Cry5B purified protein. Pre-neutralization of stomach acid improved Cry5B efficacy FIG. 19A-B. Similarly it was found that pre-neutralization of stomach acid improved the efficacy of Cry5B delivered as Bt spore-crystal lysates (SCL), shown in FIGS. 19C-D and Cry5B delivered as IBaCC, shown in FIG. 19E-F.

Example 20

Freeze-Dried or Spray-Dried IBaCC Treatment In Vivo

For future product development Cry5B would have to be stored/delivered in a dry powder form. To test that Cry5B can be dried into a power and still retain bioactivity, Cry5B IBACC powder was prepared by freeze-drying. This powder, when resuspended in water, retains full bioactivity against hookworm infections in vivo FIG. 21A-B. The near complete clearance seen with 6 mg/kg freeze-dried Cry5B IBaCC is equivalent in mass to the dose of albendazole (5 mg/kg) required to clear the same infection in hamsters. Given that Cry5B is ~500× larger molecular weight than albendazole, then these data demonstrate that Cry5B IBaCC is a highly potent nematocide on a molecule by molecule basis.

A 400 mL IBaCC sample at 10% solids w/v was also spray dried using a Yamato Pulvis GB22 through a 100 micron atomizer nozzle at 5 mLs/min with atomizing air set at 1 Kgf/$m^2$, drying air set at 0.21 $m^3$/min, inlet/outlet temperatures set at 98° C./59° C., respectively. Yield was 30.5 g of a fine, light brown powder.

Example 21

Effects of the Immune System on Cry5B Treatment

*Necator americanus* is by far the dominant hookworm species infecting humans. The sensitivity of *N. americanus* to anthelmintics is critically important for their acceptability for STH treatment. For example, the lack of efficacy of ivermectin against *Necator* (but not *Ancylostoma*) hookworms is an important reason why ivermectin is not one of the WHO approved anthelmintics for STH treatment. To test if Cry5B is active against *Necator* hookworms, we infected hamsters with a strain of *Necator americanus* recently taken from human stool specimens and adapted to immunosuppressed hamsters. To maintain the hookworms in the hamsters, hamsters were immunosuppressed daily with dexamethasone. Despite the immunosuppression, we found that both Cry5B SCL, shown in FIGS. 22A-B, and Cry5B IBaCC, shown in FIG. 22C-D, were effective at single doses against *N. americanus* hookworms. Thus, Cry5B is effective against both major hookworm genuses represented by three hookworm species in mammalian hosts.

The fact that Cry5B is effective against *N. americanus* in immunosuppressed hamsters demonstrates that Cry5B does not require the immune system to repulse the parasites. Such a result is not surprising given that Cry5B directly intoxicates STH parasites in vitro. This is not true of all anthelmintics, e.g., DEC and in some cases ivermectin, for which it appears that involvement of the immune system is important for their mechanism of action. To confirm that the immune system is not essential for Cry5B action, STAT6-/- mice were infected with *Heligmosomoides polygyrus* STH parasites. STAT6 is required for the TH2 response required for normal expulsion of STH parasites. FIG. 23A-B shows that Cry5B is effective against *H. polygyrus* even in immunosuppressed mice lacking STAT6-/-. Thus, based on the effectiveness of Cry5B in these two different immunosuppressed systems, we conclude that Cry5B acts directly on the parasites and does not require a fully intact immune system for efficacy.

Example 22

Effects of Repeated Doses of Cry5B Treatment on Animals

Although Cry5B does not require the immune system to act, the immune system might still interact with Cry5B and neutralize its activity. Whether or not repeated exposure to Cry5B might result in an adverse immunological response in the animal that would reduce its efficacy was tested. To assess this, hamsters were pre-exposed to two doses of Cry5B prior to infection with *A. ceylanicum* hookworms. A control group did not receive the pre-exposure to Cry5B but did receive the hookworm infection. Both groups were then treated therapeutically with Cry5B either as pure protein, shown in FIG. 24A-B or SCL, shown in FIG. 24C. In both cases, the efficacy of Cry5B was not altered by pre-exposure to Cry5B. These data demonstrate that Cry5B will be effective over repeated doses.

Example 23

Effects of Cry5B Treatment on Hookworm Infection in Dogs

Two beagles were inoculated per os with 1000 *Ancylostoma caninum* larvae. Forty one days post-infection, stool was collected for determination of fecal egg loads and the dog intestines were imaged using capsule endoscopy to count hookworms (Lee, A., et al. *Int. J. Parasitol.* 41, 1377-1383, 2011). One dose of Cry5B SCL (~40 mg/kg) was given by gavage on each of day 42 and 44 post-infection. On day 49 post-infection a final fecal egg count was taken and capsule endoscopy repeated for final hookworm counts. Table 6 below shows that Cry5B treatment was highly effective against *A. caninum* in dogs.

TABLE 6

*A. caninum* fecal egg count and hookworm burden reduction in dogs (n = 2) following treatment with 40 mg/kg Cry5B

| | Fecal Egg Count (EPG of Feces) | | Hookworm Burden | |
|---|---|---|---|---|
| | Pre-Treatment | Post-Treatment | Pre-Treatment | Post-Treatment |
| Dog 1 | 15750 | 1590 | 84 | 4 |
| Dog 2 | 9412 | 573 | 56 | 3 |
| Average | 12581 | 1081.5 | 70 | 3.5 |
| % Reduction | — | 91.4% | — | 95% |

Example 24

Anti-Nematode Efficacy of BaCC on *C. Elegans*

Synchronous fourth larval staged hermaphrodites were placed in wells with OP50 *Escherichia coli* as a food source plus appropriate test article (e.g., BaCC or IBaCC) and tetracycline to prevent infection by any of the bacteria. To assess the effects of Cry5B-BaCC on the laboratory nematode, *C. elegans* were incubated with 100 µg/mL Cry5B-BaCC for 24 hours at 25° C. Cry5B-BaCC was intoxicating to *C. elegans* as depicted in FIGS. 17E-F.

Example 25

Bioactivity of carvacrol-treated Crystal-*E. coli* on *C. elegans*. *Escherichia coli* cells expressing nematicidal Crystal protein or empty vector were treated for 15 minutes with 1 mg/mL carvacrol. The cells were washed in sterile water 3 times. CFUs were determined for untreated and carvacrol-treated cells by serial dilution plating on LB plates. In addition, *C. elegans* nematode L4 hermaphrodites were fed overnight $1.8 \times 10^7$ cells/mL of *E. coli* untreated or carvacrol-treated, Crystal expressing and empty vector (4 conditions) at 25° C. for 16 hr. As shown in FIG. 25B, empty vector untreated/treated had no impact on the health of *C. elegans* but both carvacrol-treated/untreated Crystal-expressing *E. coli* intoxicated *C. elegans* completely. In addition, as shown in FIG. 25A treatment of the *E. coli* with carvacrol effectively killed the *E. coli*.

REFERENCES

1. Bethony J, Brooker S, Albonico M, Geiger S M, Loukas A, Diemert D, Hotez P J. 2006. Soil-transmitted helminth infections: ascariasis, trichuriasis, and hookworm. Lancet 367:1521-1532.

2. Hall A, Hewitt G, Tuffrey V, de Silva N. 2008. A review and metaanalysis of the impact of intestinal worms on child growth and nutrition. Matern. Child Nutr. 4(Suppl 1):118-236.

3. Knopp S, Steinmann P, Keiser J, Utzinger J. 2012. Nematode infections: soil-transmitted helminths and trichinella. Infect. Dis. Clin. North Am. 26:341-358.

4. Tchuem Tchuente L A. 2011. Control of soil-transmitted helminths in sub-Saharan Africa: diagnosis, drug efficacy concerns and challenges. Acta Trop. 120(Suppl 1):S4-S11.

5. Hotez P J. 2008. Forgotten people, forgotten diseases: the neglected tropical diseases and their impact on global health and development. ASM Press, Washington, D.C.

6. Keiser J, Utzinger J. 2010. The drugs we have and the drugs we need against major helminth infections. Adv. Parasitol. 73:197-230.

7. Humphries D, Mosites E, Otchere J, Twum W A, Woo L, Jones-Sanpei H, Harrison L M, Bungiro R D, Benham-Pyle B, Bimi L, Edoh D, Bosompem K, Wilson M, Cappello M. 2011. Epidemiology of hookworm infection in Kintampo North Municipality, Ghana: patterns of malaria coinfection, anemia, and albendazole treatment failure. Am. J. Trop. Med. Hyg. 84:792-800.

8. Soukhathammavong P A, Sayasone S, Phongluxa K, Xayaseng V, Utzinger J, Vounatsou P, Hatz C, Akkhavong K, Keiser J, Odermatt P. 2012. Low efficacy of single-dose albendazole and mebendazole against hookworm and effect on concomitant helminth infection in Lao PDR. PLoS Negl. Trop. Dis. 6:e1417. doi:10.1371/journal.pntd.0001417.

9. Stothard J R, Rollinson D, Imison E, Khamis I S. 2009. A spot-check of the efficacies of albendazole or levamisole, against soil-transmitted helminthiases in young Ungujan children, reveals low frequencies of cure. Ann. Trop. Med. Parasitol. 103:357-360.

10. Geary T G, Woo K, McCarthy J S, Mackenzie C D, Horton J, Prichard R K, de Silva N R, Olliaro P L, Lazdins-Helds J K, Engels D A, Bundy D A. 2010. Unresolved issues in anthelmintic pharmacology for helminthiases of humans Int. J. Parasitol. 40:1-13.

11. Holden-Dye L, Walker R J. 2007. Anthelmintic drugs. WormBook 2007: 1-13.

12. Cappello M, Bungiro R D, Harrison L M, Bischof L J, Griffitts J S, Barrows B D, Aroian R V. 2006. A purified *Bacillus thuringiensis* crystal protein with therapeutic activity against the hookworm parasite *Ancylostoma ceylanicum*. Proc. Natl. Acad. Sci. U.S.A. 103:15154-15159.

13. Hu Y, Georghiou S B, Kelleher A J, Aroian R V. 2010. *Bacillus thuringiensis* Cry5B protein is highly efficacious as a single-dose therapy against an intestinal roundworm infection in mice. PLoS Negl. Trop. Dis. 4:e614. doi:10.1371/journal.pntd.0000614.

14. Hu Y, Zhan B, Keegan B, Yiu Y Y, Miller M M, Jones K, Aroian R V. 2012. Mechanistic and single-dose in vivo therapeutic studies of Cry5B anthelmintic action against hookworms. PLoS Negl. Trop. Dis. 6:e1900. doi:10.1371/journal.pntd.0001900.

15. Cutting S M. 2011. *Bacillus* probiotics. Food Microbiol. 28:214-220.

16. Casula G, Cutting S M. 2002. *Bacillus* probiotics: spore germination in the gastrointestinal tract. Appl. Environ. Microbiol. 68:2344-2352.

17. Duc L H, Hong H A, Barbosa T M, Henriques A O, Cutting S M. 2004. Characterization of *Bacillus* probiotics available for human use. Appl. Environ. Microbiol. 70:2161-2171.

18. Hoa N T, Baccigalupi L, Huxham A, Smertenko A, Van P H, Ammendola S, Ricca E, Cutting A S. 2000. Characterization of *Bacillus* species used for oral bacteriotherapy and bacterioprophylaxis of gastrointestinal disorders. Appl. Environ. Microbiol. 66:5241-5247.

19. Hoa T T, Duc L H, Isticato R, Baccigalupi L, Ricca E, Van P H, Cutting S M. 2001. Fate and dissemination of *Bacillus subtilis* spores in a murine model. Appl. Environ. Microbiol. 67:3819-3823.

20. Hong H A, Huang J M, Khaneja R, Hiep L V, Urdaci M C, Cutting S M. 2008. The safety of *Bacillus subtilis* and *Bacillus indicus* as food probiotics. J. Appl. Microbiol. 105:510-520.

21. D'Arienzo R, Maurano F, Mazzarella G, Luongo D, Stefanile R, Ricca E, Rossi M. 2006. *Bacillus subtilis* spores reduce susceptibility to *Citrobacter rodentium*-mediated enteropathy in a mouse model. Res. Microbiol. 157: 891-897.

22. Duc L H, Hong H A, Fairweather N, Ricca E, Cutting S M. 2003. Bacterial spores as vaccine vehicles. Infect. Immun 71:2810-2818.

23. Hoang T H, Hong H A, Clark G C, Titball R W, Cutting S M. 2008. Recombinant *Bacillus subtilis* expressing the *Clostridium perfringens* alpha toxoid is a candidate orally delivered vaccine against necrotic enteritis. Infect. Immun 76:5257-5265.

24. La Ragione R M, Casula G, Cutting S M, Woodward M J. 2001. *Bacillus subtilis* spores competitively exclude *Escherichia coli* O78:K80 in poultry. Vet. Microbiol. 79:133-142.

25. La Ragione R M, Woodward M J. 2003. Competitive exclusion by *Bacillus subtilis* spores of *Salmonella enterica* serotype *Enteritidis* and *Clostridium perfringens* in young chickens. Vet. Microbiol. 94:245-256.

26. Permpoonpattana P, Hong H A, Phetcharaburanin J, Huang J M, Cook J, Fairweather N F, Cutting S M. 2011 Immunization with *Bacillus* spores expressing toxin A pep- 27. Song M, Hong H A, Huang J M, Colenutt C, Khang D D, Nguyen T V, Park S M, Shim B S, Song H H, Cheon I S, Jang J E, Choi J A, Choi Y K, Stadler K, Cutting S M. 2012. Killed *Bacillus subtilis* spores as a mucosal adjuvant for an H5N1 vaccine. Vaccine 30:3266-3277.

28. Conlan J V, Khamlome B, Vongxay K, Elliot A, Pallant L, Sripa B, Blacksell S D, Fenwick S, Thompson R C. 2012. Soil-transmitted helminthiasis in Laos: a community-wide cross-sectional study of humans and dogs in a mass drug administration environment. Am. J. Trop. Med. Hyg. 86:624-634.

29. Marroquin L D, Elyassnia D, Griffitts J S, Feitelson J S, Aroian R V. 2000. *Bacillus thuringiensis* (Bt) toxin susceptibility and isolation of resistance mutants in the nematode *Caenorhabditis elegans*. Genetics 155:1693-1699.

30. Dubnau D, Davidoff-Abelson R. 1971. Fate of transforming DNA following uptake by competent *Bacillus subtilis*. I. Formation and properties of the donor-recipient complex. J. Mol. Biol. 56:209-221.

31. Sierro N, Makita Y, de Hoon M, Nakai K. 2008. DBTBS: a database of transcriptional regulation in *Bacillus subtilis* containing upstream intergenic conservation information. Nucleic Acids Res. 36:D93-D96.

32. Shevchenko A, Wilm M, Vorm O, Mann M. 1996. Mass spectrometric sequencing of proteins silver-stained polyacrylamide gels. Anal. Chem. 68:850-858.

33. National Research Council. 1996. Guide for the care and use of laboratory animals. National Academies Press, Washington, D.C.

34. Hu Y, Xiao S H, Aroian R V. 2009. The new anthelmintic tribendimidine is an L-type (levamisole and pyrantel) nicotinic acetylcholine receptor agonist. PLoS Negl. Trop. Dis. 3:e499. doi:10.1371/journal.pntd.0000499.

35. Hu Y, Platzer E G, Bellier A, Aroian R V. 2010. Discovery of a highly synergistic anthelmintic combination that shows mutual hypersusceptibility. Proc. Natl. Acad. Sci. U.S.A. 107:5955-5960.

36. Lereclus D, Arantes O, Chaufaux J, Lecadet M. 1989. Transformation and expression of a cloned delta-endotoxin gene in *Bacillus thuringiensis*. FEMS Microbiol. Lett. 51:211-217.

37. Yang Y, Qi Y, Huang Y. 1996. Cloning and expression of full-length delta-endotoxin cryIA(c) gene in three kinds of prokaryotic systems using shuttle vector pHT3101. Wei Sheng Wu Xue Bao 36:173-180.

38. Youngman P, Perkins J B, Losick R. 1984. Construction of a cloning site near one end of Tn917 into which foreign DNA may be inserted without affecting transposition in *Bacillus subtilis* or expression of the transposonborne erm gene. Plasmid 12:1-9.

39. Cannon R J C. 1996. *Bacillus thuringiensis* use in agriculture: a molecular perspective. Biol. Rep. 71:561-636.

40. Hu Y, Aroian R V. 2012. Promise of *Bacillus thuringiensis* crystal proteins as anthelmintics, p 267-281. In Caffrey C R (ed), Parasitic helminths: targets, screens, drugs, and vaccines. Wiley-VCH Verlag Gmh & Co, KGaA, Weinheim, Germany.

41. Bischof L J, Huffman D L, Aroian R V. 2006. Assays for toxicity studies in *C. elegans* with Bt crystal proteins. Methods Mol. Biol. 351:139-154.

42. Kho M F, Bellier A, Balasubramani V, Hu Y, Hsu W, Nielsen-LeRoux C, McGillivray S M, Nizet V, Aroian R V. 2011. The pore-forming protein Cry5B elicits the pathogenicity of *Bacillus* sp. against *Caenorhabditis elegans*. PLoS One 6:e29122. doi:10.1371/journal.pone.0029122.

43. Baum J A, Malvar T. 1995. Regulation of insecticidal crystal protein production in *Bacillus thuringiensis*. Mol. Microbiol. 18:1-12.

44. Buasri W, Panbangred W. 2012. Large crystal toxin formation in chromosomally engineered *Bacillus thuringiensis* subsp. aizawai due to sigmaE accumulation. Appl. Environ. Microbiol. 78

60. Boontawan A, Stuckey D C. 2005. *Mass transfer of terpenes through a silicone rubber membrane in a liquid-liquid contacting system*. Biotechnol. Prog.

61. Krings U, Berger R G. 1998. *Biotechnological production of Øavours and fragrances*. Appl. Microbiol. Biotechnol.

62. Chan A C, Ager D, Thompson I P. 2013. *Resolving the mechanism of bacterial inhibition by plant secondary metabolites employing a combination of whole-cell biosensor*. J. Microbiol. Methods.

63. Lereclus D, Agaisse H, Gominet M, Chaufaux J. 1995. *Overproduction of Encapsulated Insecticidal Crystal Proteins in a Bacillus thuringiensis spoOA Mutant*. Nat. Biotechnol.

64. Agaisse H, Lereclus D. 1994. *Expression in Bacillus subtilis of the Bacillus thuringiensis cryIIIA toxin gene is not dependent on a sporulation-specific sigma factor and is increased in a spo0A mutant*. J. Bacteriol.

65. Urban Jr J F, Hu Y, Miller M M, Scheib U, Yiu Y Y, Aroian R V. 2013. *Bacillus thuringiensis-derived Cry5B has potent anthelmintic activity against Ascaris suum*. PLoS Negl. Trop. Dis.

66. Roh J Y, Choi J Y, Li M S, Jin B R, Je Y H. 2007. *Bacillus thuringiensis as a specific, safe, and effective tool for insect pest control*. J. Microbiol. Biotechnol.

67. Hu Y, Miller M M, Derman A I, Ellis B L, Monnerat R G, Pogliano J, Aroian R V. 2013. *Bacillus subtilis strain engineered for treatment of soil-transmitted helminth diseases*. Appl. Environ. Microbiol.

67. Silvaggi, J., et al. *Unmasking novel sporulation genes in Bacillus subtillus*. J Bacteriol. 186, 8089-8095, 2004.

68. Sandman, K., et al. *Genetic Analysis of Bacillus subtilis spo Mutations Generated by Tn917-Mediated Insertional Mutagenesis*. Genetics. 117, 603-617, 1987.

69. Malvar and Baum, *Tn5401 Disruption of the spoOF Gene, Identified by Direct Chromosomal Sequencing, Results in CryIIIA Overproduction in Bacillus thuringiensis*. J Bacteriol. 176, 4750-4753, 1994.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

While particular steps, elements, embodiments and applications of the present invention have been shown and described herein for purposes of illustration, it will be understood, of course, that the invention is not limited thereto since modifications may be made by persons skilled in the art, particularly in light of the foregoing teachings, without deviating from the spirit and scope of the invention. Accordingly, the invention is not limited except as by the appended claims.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An orally-available pharmaceutical composition comprising a killed, non-sporulating bacterium that expresses a nematicidal protein, wherein the bacterium has a genetic mutation comprising a deletion or inactivation of one or more genes selected from the group consisting of kinA, kinB, spo0A, spo0B, spo0E, spo0F, spo0J, spo0M, spoIIB, spoIID, spoIIE, spoIIF, spoIIG, spoIIL, spoIIM, spoIIIA, spoIIIB, spoIIIE, spoIVA, spoIVC, spoIVD, spoVG, spoVK, spoVL, spoVM, spoVN, spoVP, spoVQ, spoVID, σH, σF, σE, σG, and σK that results in a defect in sporulation, wherein the nematicidal protein is a cytoplasmic crystal (Cry) protein selected from the group consisting of Cry5B, Cry5C, Cry5D, Cry6A, Cry13A, Cry14A, Cry21A, and Cry 21B, and wherein the nematicidal protein is trapped in the cytosol of the bacterium.

2. The pharmaceutical composition of claim 1, wherein a nematicidal gene encoding the nematicidal protein is under control of a non-sporulation-specific promoter.

3. The pharmaceutical composition of claim 1, wherein the bacterium is a Gram-positive bacterium.

4. The pharmaceutical composition of claim 1, wherein the composition is encapsulated by a pharmaceutical grade capsule in a dry powdered form.

5. The pharmaceutical composition of claim 1, wherein the bacterium is a species of Bacillus.

6. The pharmaceutical composition of claim 1, wherein the bacterium is Bacillus thuringiensis (Bt).

7. A method for producing the pharmaceutical composition of claim 1, the method comprising:
   (a) exposing a non-sporulating bacterium to an antimicrobial agent, thereby killing or inactivating the bacterium, wherein the bacterium is genetically engineered to express a nematicidal protein and wherein the bacterium has a genetic mutation that prevents sporulation such that the nematicidal protein is trapped in the cytosol of the bacterium; and
   (b) formulating the killed or inactivated bacterium in an orally-available dosage form.

8. The method of claim 7, wherein formulating comprises one or more of:
   (a) lyophilizing or spray drying the bacterium; or
   (b) encapsulating the bacterium in a pharmaceutical-grade capsule.

9. The method of claim 7, wherein the antimicrobial agent is selected from the group consisting of: an antimicrobial compound and gamma irradiation.

10. The method of claim 9, wherein the antimicrobial compound is:
   (a) a food-grade antibiotic;
   (b) a beta-lactam antibiotic; or
   (c) a terpene, iodine or formaldehyde.

11. The method of claim 10, wherein the terpene is selected from the group consisting of thymol, eugenol, geraniol, carvacrol, and citral, and combinations thereof.

12. A method of treating a parasitic worm infection in a subject comprising administering to the subject the pharmaceutical composition of claim 1.

* * * * *